United States Patent
Li et al.

(10) Patent No.: US 10,479,798 B2
(45) Date of Patent: Nov. 19, 2019

(54) SIX-MEMBERED RING BENZO DERIVATIVES AS DPP-4 INHIBITOR AND USE THEREOF

(71) Applicants: EAST CHINA UNIVERSITY OF SCIENCE AND TECHNOLOGY, Shanghai (CN); SHANGHAI INSTITUTE OF MATERIA MEDICA, CHINESE ACADEMY OF SCIENCES, Shanghai (CN)

(72) Inventors: Honglin Li, Shanghai (CN); Hualiang Jiang, Shanghai (CN); Yufang Xu, Shanghai (CN); Jia Li, Shanghai (CN); Zhenjiang Zhao, Shanghai (CN); Jingya Li, Shanghai (CN); Hongling Xu, Shanghai (CN); Shiliang Li, Shanghai (CN)

(73) Assignees: EAST CHINA UNIVERSITY OF SCIENCE AND TECHNOLOGY, Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 26 days.

(21) Appl. No.: 15/523,058

(22) PCT Filed: Oct. 30, 2015

(86) PCT No.: PCT/CN2015/093384
§ 371 (c)(1),
(2) Date: Apr. 28, 2017

(87) PCT Pub. No.: WO2016/066134
PCT Pub. Date: May 6, 2016

(65) Prior Publication Data
US 2017/0313715 A1     Nov. 2, 2017

(30) Foreign Application Priority Data

Oct. 31, 2014   (CN) .......................... 2014 1 0609270

(51) Int. Cl.
| | |
|---|---|
| *C07D 311/60* | (2006.01) |
| *C07D 311/92* | (2006.01) |
| *C07D 405/04* | (2006.01) |
| *C07D 493/04* | (2006.01) |
| *A61K 31/352* | (2006.01) |
| *A61K 31/5377* | (2006.01) |
| *C07D 221/10* | (2006.01) |
| *C07D 335/04* | (2006.01) |
| *C07D 417/04* | (2006.01) |

(52) U.S. Cl.
CPC .......... *C07D 493/04* (2013.01); *C07D 311/60* (2013.01); *C07D 311/92* (2013.01)

(58) Field of Classification Search
CPC combination set(s) only.
See application file for complete search history.

(56) References Cited

U.S. PATENT DOCUMENTS

2007/0232676 A1   10/2007  Biftu et al.

FOREIGN PATENT DOCUMENTS

| EA | 200870380 A1 | 2/2009 |
| WO | 2008/097976 A1 | 8/2008 |
| WO | 2014/162320 A2 | 10/2014 |
| WO | WO-2014162320 A2 * | 10/2014 ........... C07D 311/60 |

OTHER PUBLICATIONS

Varma et al. J. Heterocyclic Chem. 1987, 24, 767. (Year: 1987).*
Chemical Abstract Service STN Registry No. 1279894-53-9 [Entered STN: Apr. 14, 2011]. (Year: 2011).*
Chemical Abstract Service STN Registry No. 1228538-85-9 [Entered STN: Jun. 29, 2010]. (Year: 2010).*
Chemical Abstract Service STN Registry No. 721388-34-7 [Entered STN: Aug. 2, 2004]. (Year: 2004).*
Chemical Abstract Service STN Registry No. 81289-29-4 [Entered STN: Nov. 16, 1984]. (Year: 1984).*
English Translation of the International Search Report corresponding to PCT/CN2015/093384 dated Jan 29, 2016, 4 pages.
English Translation of the Written Opinion corresponding to PCT/CN2015/093384 dated Jan 29, 2016, 7 pages.
Arora, P. K. "Sodium Borohydride Reduction of 3-Nitro-2-substituted-phenyl-2H[I]benzopyrans," *Indian Journal of Chemistry* (Nov. 1981; accepted Apr. 29, 1981); 20B:951-954.
Das, Bhaskar C. et al., "Synthesis of function-oriented 2-phenyl-2H-chromene derivatives using L-pipecolinic acid and substituted guanidine organocatalysts," *Tetrahedron Lett.* (May 1, 2010) 51(19):2567-2570.

(Continued)

*Primary Examiner* — Amanda L Aguirre
(74) *Attorney, Agent, or Firm* — Mintz Levin Cohn Ferris Glovsky and Popeo PC

(57) ABSTRACT

The present invention relates to six-membered ring benzo derivatives as a DPP-4 inhibitor and a use thereof. In particular, the present invention relates to a compound as shown in formula I, a pharmaceutical composition containing the compound as shown in formula I and a use of the compound in the preparation of drugs for treating DPP-4 related diseases or inhibiting DPP-4.

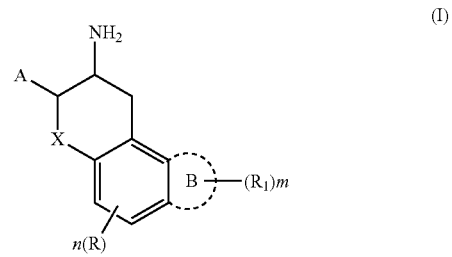

17 Claims, No Drawings

(56) References Cited

OTHER PUBLICATIONS

Pirkle, William H. et al., "Liquid and subcritical $CO_2$ separations of enantiomers on a broadly applicable polysiloxane chiral stationary phase," *Journal of Chromatography A.* (1996; accepted May 13, 1996); 753:109-119.

Varma, Rajender S. et al., "Reduction of α,β-Unsaturated Nitroalkenes with Borane and Borohydrides. A Convenient Route to 3-Nitro-, 3-Hydroxylamino-, and 3-Amino-2H-1-benzopyran Derivatives," *J. Heterocyclic Chem.* (May-Jun. 1987); 24:767-772.

Examination Report No. 1 for corresponding Application No. 2015341177 in Australia dated Dec. 19, 2017; 4 pages.

Examination Report-Office Action-Communication pursuant to Article 94(3) EPC for corresponding Application No. 15855852.8 in Europe dated Jan. 30, 2019; 6 pages.

Extended European Search Report dated Feb. 27, 2018 corresponding to European Patent Application No. 15855852.8 filed Oct. 30, 2015.

Search Report dated Apr. 16, 2018 corresponding to Application No. 2017117559 in the Russian Federation; 3 pages; See, p. 2, Item 6 for references cited (listing is in English).

First Office Action dated Apr. 18, 2018 for corresponding Application No. 2017117559 in the Russian Federation; 7 pages (English Translation).

Second Office Action dated Sep. 14, 2018 for corresponding Application No. 2017117559 in the Russian Federation; 5 pages (English Translation).

Third Office Action dated Jan. 31, 2019 for corresponding Application No. 2017117559 in the Russian Federation; 4 pages (English Translation).

\* cited by examiner

SIX-MEMBERED RING BENZO DERIVATIVES AS DPP-4 INHIBITOR AND USE THEREOF

TECHNICAL FIELD

The present invention relates to the field of pharmaceutical chemistry. In particular, the present invention relates to novel benzo six-membered ring derivatives, to synthesis methods thereof and uses in the preparation of a medicament for treating type 2 diabetes and related diseases.

BACKGROUND

Diabetes mellitus (DM) is a metabolic disease characterized in that the level of glucose (blood glucose) in blood is increased, and it is a slowly progressive disease caused by genetic factors in combination with environmental factors. With the improvement in people's living standards, the number of people with diabetes is increased rapidly. According to the International Diabetes Federation, in 2012, there are about 371 million diabetic patients, and the number of diabetes patients in China is 90 million, which is the country with the largest number of patients in the world (Wild, S.; Roglic, G.; Green, A.; Sicree, R.; King, H. Diabetes Care. 2004, 27, 1047-1053). Approximately 3.8 million people die from diabetes each year, and diabetes ranks thirdly as AIDS which is only after cancer and cardiovascular disease.

According to the pathogenesis, diabetes can be divided into type 1 and type 2. Type 1 diabetes is mainly due to the insufficiency of endogenous insulin secretion caused by autoimmune-damaged islet β cells; that is, absolute lack of insulin. And patients need to be treated with insulin. Type 2 diabetes is due to reduced insulin secretion or insulin resistance caused by dysfunctional islet β-cells, that is, relative lack of insulin resulting in abnormality in metabolism of sugar, protein and fat.

Clinically, diabetes is treated mainly by using a variety of oral hypoglycemic agents and insulin supplements to delay the progress of diabetes. However, these methods, sometimes, can not achieve desired therapeutic effects, and there are side effects of inducing hypoglycemia and cardiovascular disease etc., and no protective effects on injured islet cells. With the deep understanding of the pathogenesis of diabetes, it is a focus of research to find effective hypoglycemic drugs according to mechanisms of key targets in the pathogenesis.

Dipeptidyl peptidase-4 (DPP-4) has been demonstrated as an effective target for the treatment of type 2 diabetes mellitus, which can rapidly degrade many important Incretins, such as glucagon-like peptide 1 (GLP-1) and glucose-dependent insulinotropic peptide (GIP), resulting in inadequate insulin secretion. Therefore, DPP-4 inhibitors can improve the activity of GLP-1 and GIP, promote insulin secretion, and lower blood sugar.

Clinical trials have shown that DPP-4 inhibitors can lower blood glucose levels and increase glucose tolerance, and there is no side effect, such as weight gain and hypoglycemia. At present, clinically applied DPP-4 inhibitors are Sitagliptin, Saxagliptin, Vildagliptin, Alogliptin and Linagliptin (Havale, S. H.; Pal, M. Bioorg. Med. Chem. 2009, 17, 1783-1802; Gupta, R.; Walunj, S. S.; Tokala, R. K.; Parsa, K. V.; Singh, S. K.; Pal, M. Curr. Drug. Targets, 2009, 10, 71-87). The market for hypoglycemic drugs is already dominated by hypoglycemic drugs as DPP-4 inhibitor. For example, in 2009, the sale of Sitagliptine from Merck & Co., Inc., reached $13.1 billion, which the only hypoglycemic drug which exceeded $10 billion.

However, all of the currently marketed DPP-4 inhibitors are in patent protection period, a variety of new DPP-4 inhibitors are still in clinical research stage. Therefore, there is an urgent need in the art for the development of novel, efficient DPP-4 inhibitors with low toxicity.

SUMMARY

It is an object of the present invention to provide a compound as a novel DPP-4 inhibitor with novel structure, high efficiency, low toxicity, a pharmaceutical composition comprising said compound, a process for the preparation of said compound, and use of said compound in the preparation of a medicament for preventing or treating DPP-4 related diseases.

In a first aspect, the present invention provides a compound of general formula I, or a pharmaceutically acceptable salt or prodrug thereof, or an optically active isomer or solvate thereof:

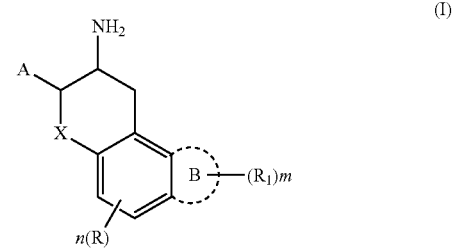

wherein

X is selected from $CH_2$, O, S and NH;

A is an unsubstituted benzene ring or a benzene ring with 1 to 5 substituents, wherein each substituent is independently selected from a halogen, a cyano, a hydroxy, a $C_{1-6}$ alkyl or a $C_{1-6}$ alkyl substituted by a halogen, preferably F, more preferably 1 to 5 F, a $C_{1-6}$ alkoxy or a $C_{1-6}$ alkoxy substituted by a halogen, preferably F, more preferably 1 to 5 F;

A may also be selected from a nitrogen-containing, or sulfur-containing five-membered or six-membered saturated or unsaturated heterocycle with 1 to 4 substituents, wherein each substituent is independently selected from a halogen, a cyano, a boronic acid group;

A heterocycle is selected from the following structures:

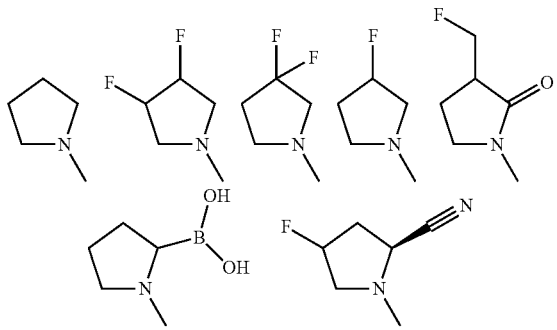

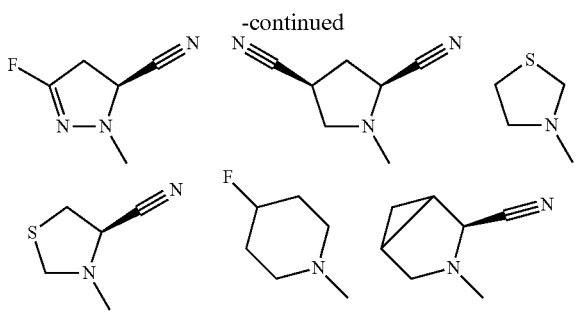

R is H, a halogen, a cyano, a hydroxy, a $C_{1-6}$ alkyl or $C_{1-6}$ alkyl with 1 to 5 F atoms, $C_{1-6}$ alkoxy or $C_{1-6}$ alkoxy with 1 to 5 F atoms, n=1-2;

Ring B is not present or is selected from an aromatic benzene ring, an aromatic heterocycle, a saturated or unsaturated 5-membered or 5-membered ring, a nitrogen-, oxygen- and sulfur-containing five- or six-membered saturated or unsaturated heterocycle, wherein the substituent $R_1$ is independently selected from the group consisting of a carbonyl, a halogen, a cyano, a hydroxy, a $C_{1-6}$ alkyl, a $C_{1-10}$ alkoxy (preferably a $C_{1-6}$ alkoxy), a $C_{2-10}$ alkoxy with alkenyl bond, alkynyl bond, an optionally substituted benzyloxy, a $C_{1-10}$ alkylcarbonyloxy, a $C_{1-3}$ alkoxymethoxy, a disubstituted $OCH_2CH_2O$ and $OCH_2O$, COOH, a $C_{1-6}$ alkoxycarbonyl, a carbamoyl, an amino, a $NR^2R^3$, a $C_{1-5}$ alkylcarboxamido, a $C_{3-5}$ alkyllactam group, a $C_{1-6}$ alkylsulfonamido, a $C_{3-5}$ alkylsultam group, a mercapto, a $C_{1-5}$ alkylmercapto, a $C_{1-5}$ alkylsulfonyl, a $C_{3-5}$ cycloalkylsulfonyl, a $C_{1-5}$ alkylsulfinyl, m=1 to 4;

$R^2$, $R^3$ are independently selected from a $C_{1-6}$ alkyl, or $R^2$ and $R^3$ together form a substituted or unsubstituted 5- or 6-membered cycloalkyl, or a substituted or unsubstituted 5- or 6-membered heterocycle group containing N, O.

In a preferred embodiment, the present invention provides a compound of general formula (II), or a pharmaceutically acceptable salt or prodrug thereof, or an optically active isomer or solvate thereof:

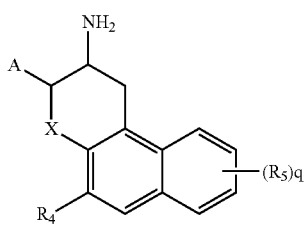

(II)

wherein
X is selected from $CH_2$, O, S and NH;

A is a benzene ring with 1 to 5 substituents, wherein each substituent is independently selected from a halogen, a cyano, a hydroxy, a $C_{1-6}$ alkyl or a $C_{1-6}$ alkyl substituted by a halogen, preferably F, more preferably 1 to 5 F, a $C_{1-6}$ alkoxy or a $C_{1-6}$ alkoxy substituted by a halogen, preferably F, more preferably 1 to 5 F;

$R^4$ is independently selected from H, a hydroxyl, F, a cyano;

$R^5$ is a halogen, a cyano, a hydroxyl, a mercapto, a $C_{1-6}$ alkyl group or a $C_{1-6}$ alkyl group containing 1 to 5 F atoms, a $C_{1-6}$ alkoxy, a hydroxyl, a $C_{1-10}$ alkylcarbonyloxy, a $C_{1-3}$ alkoxymethyloxy, COOH, a $C_{1-6}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a $C_{1-6}$ alkylthio or a $C_{1-6}$ alkylthio containing 1 to 5 F atoms, a $C_{1-6}$ alkylsulfinyl, a $C_{1-6}$ alkylsulfonyl, an amino, an acetylamino, a methanesulfonamido, a methylcarbamido, a N-propanesulfonyllactam group, a N-butanesulfonyllactam group, a 4-morpholinyl, a N-methylpiperazin-4-yl, a piperazinyl, a 3-methanesulfonylpiperazinyl, a 3,3-difluorotetrahydropyrrolyl, a 2-aminoformylpiperidyl, a 3-pyrazolylamino, q=1-4.

In a preferred embodiment, the present invention provides a compound of general formula (III), or a pharmaceutically acceptable salt or prodrug thereof, or an optically active isomer or solvate thereof:

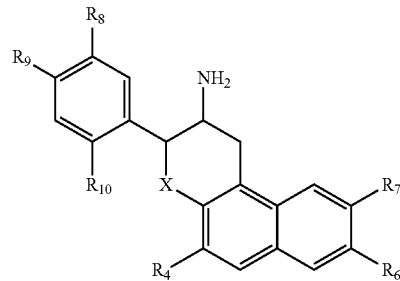

(III)

wherein
X is selected from O, S and NH;
$R^4$ is independently selected from H, a hydroxyl;
$R^6$, $R^7$ are independently selected from a hydrogen, a halogen, a cyano, a hydroxy, a mercapto, a $C_{1-2}$ alkoxy, a $C_{1-2}$ alkylcarbonyloxy, a $C_{1-3}$ alkoxymethoxy, COOH, a $C_{1-2}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a methylthio, a methylsulfinyl, a methanesulfonyl, an amino, acetamido, methanesulfonamido, a methylcarbamido, N-propanesulfonyllactam group, N-butanesulfonyllactam group, a 4-morphinyl, a N-methylpiperazin-4-yl, a piperazinyl, a 3-methanesulfonylpiperazinyl, a 3,3-difluorotetrahydropyrrolyl, a 2-aminoformylpiperidyl, a 3-pyrazolylamino;

$R^8$, $R^9$ and $R^{10}$ are independently selected from H, Cl, F, a cyano.

In another preferred embodiment, the present invention provides a compound selected from the following group, or a pharmaceutically acceptable salt or prodrug thereof:

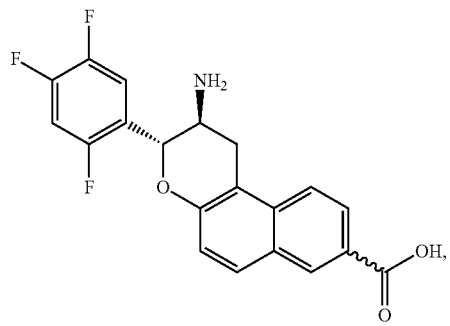

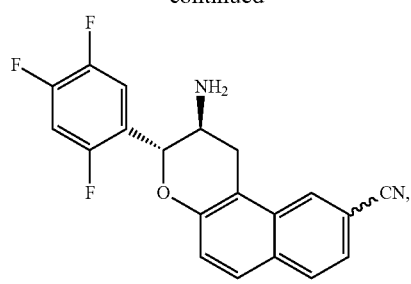
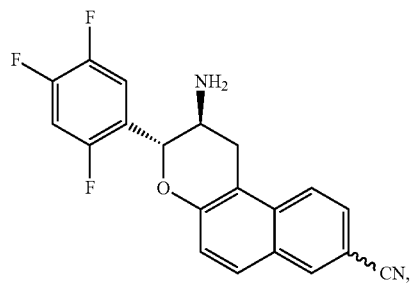
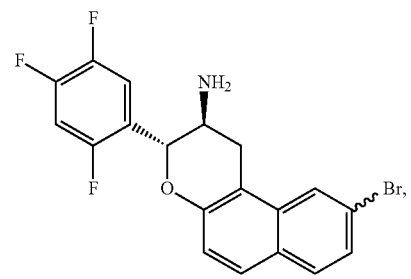
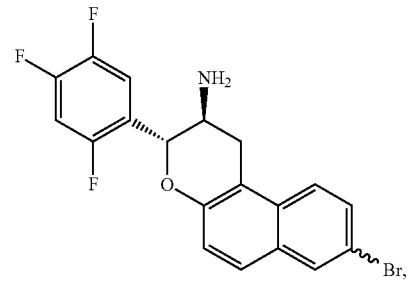
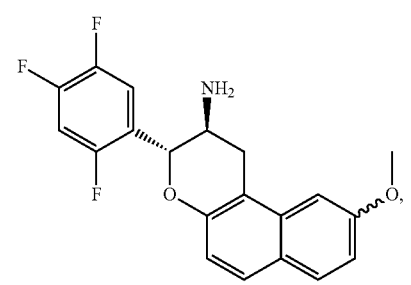
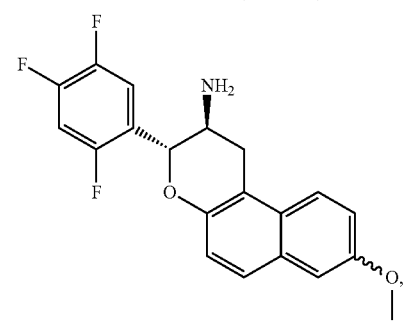
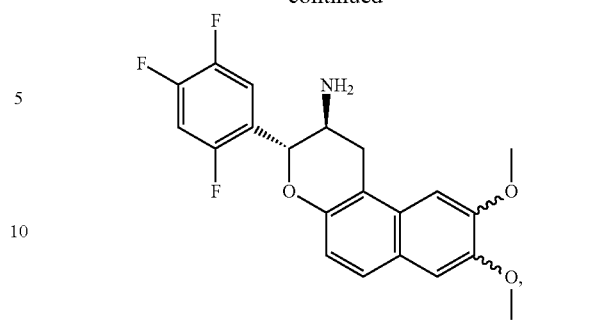
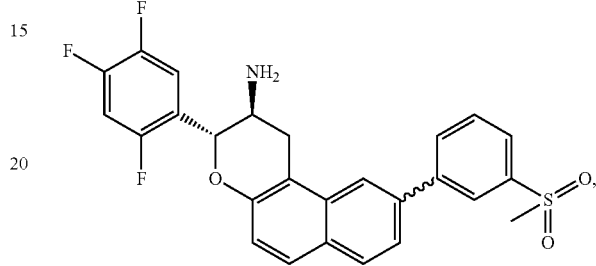
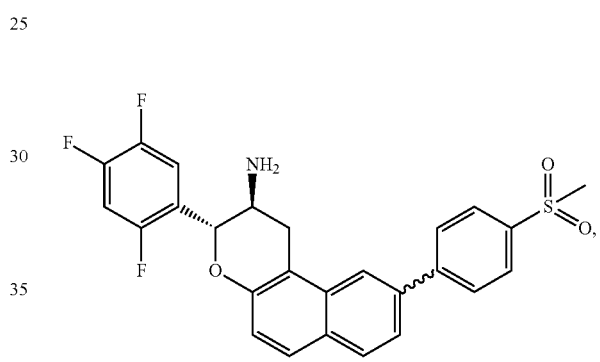
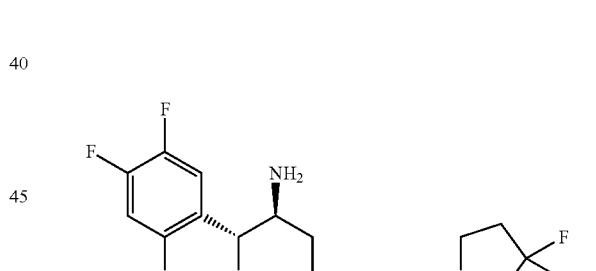
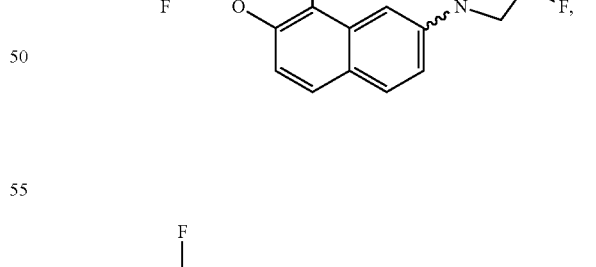
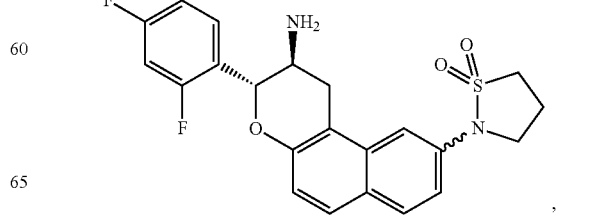

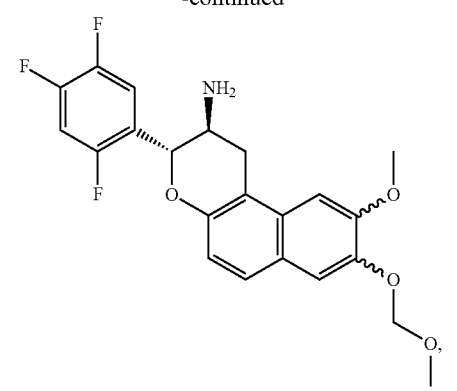
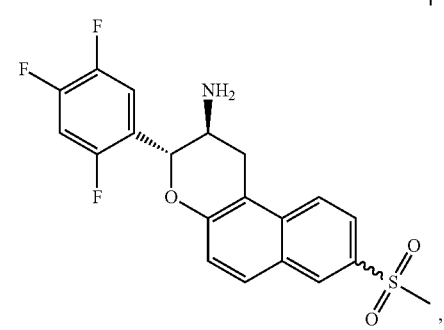
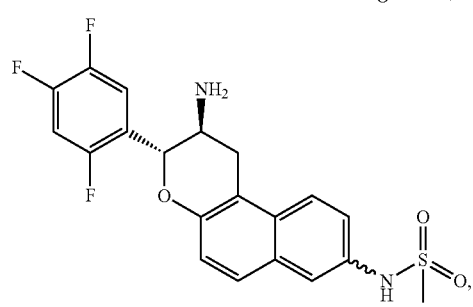
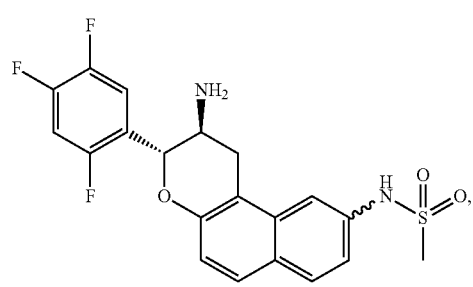
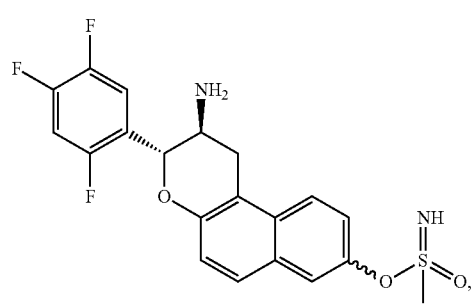
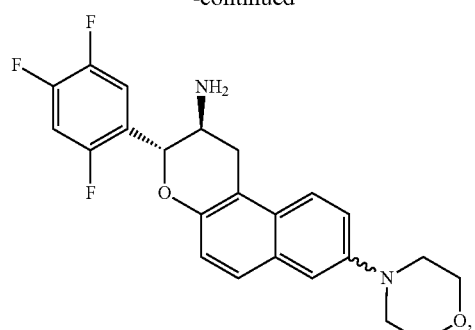
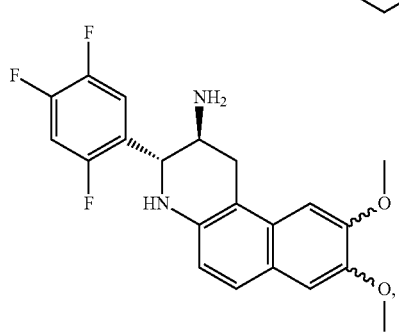
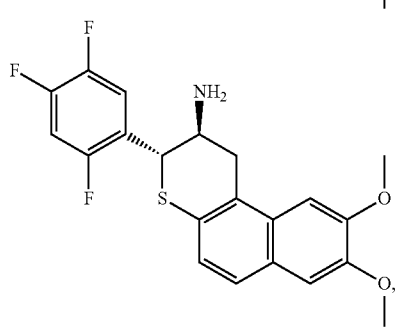
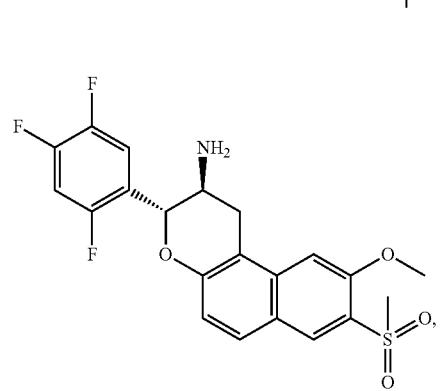
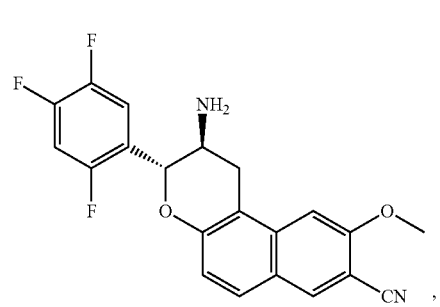

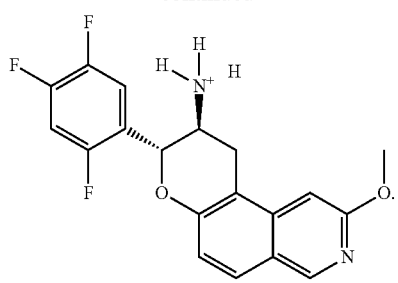
In other preferred embodiments, the present invention provides a compound selected from the following group, or a pharmaceutically acceptable salt or prodrug thereof:
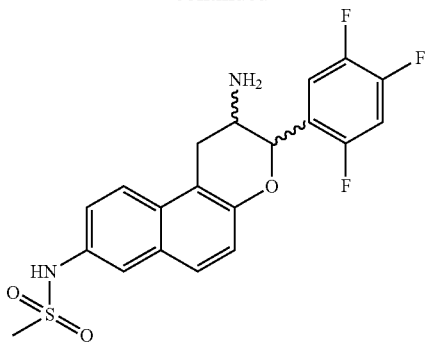
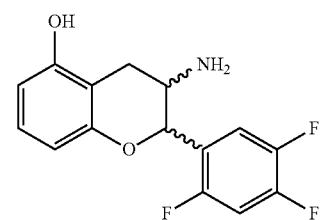
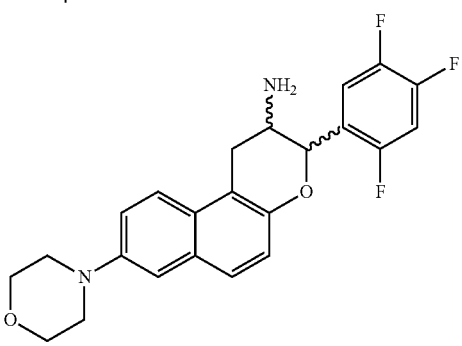
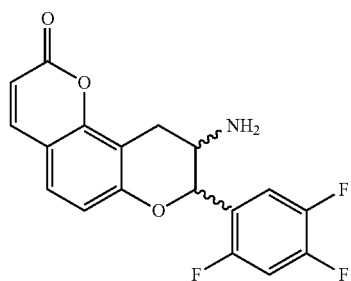
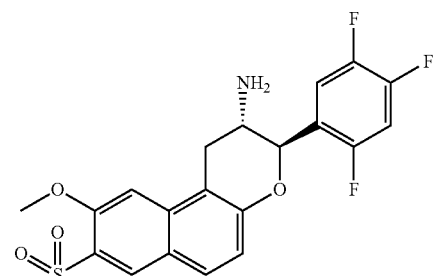
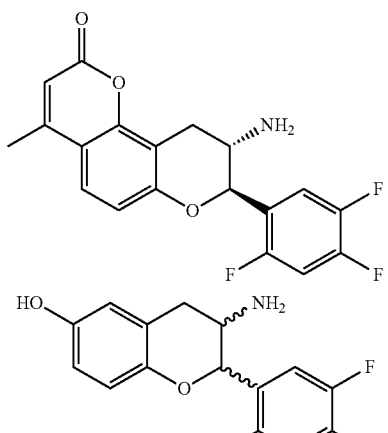
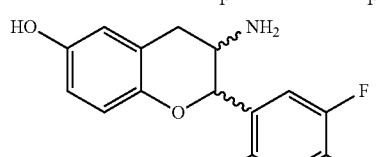
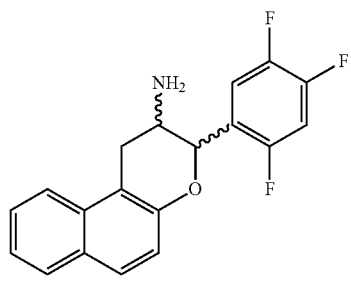
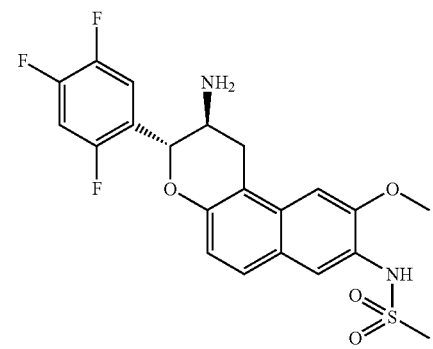

-continued

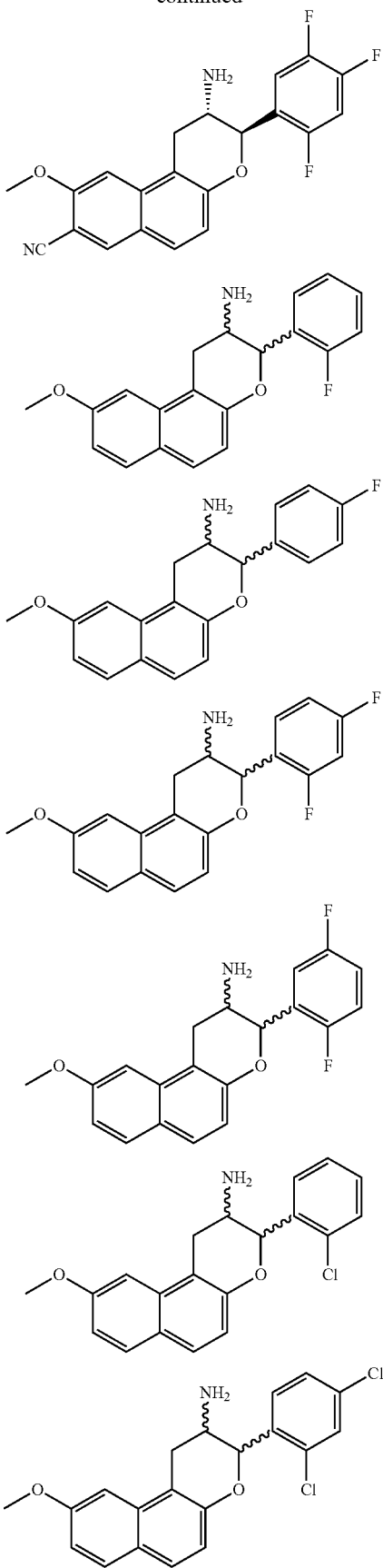

-continued

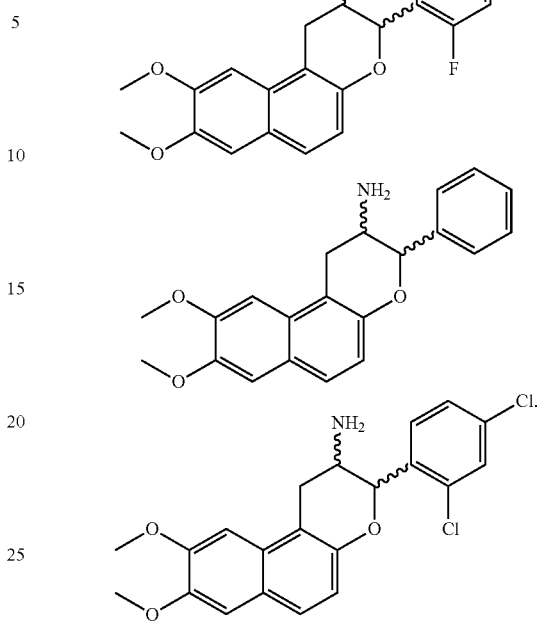

In a second aspect, the present invention provides a pharmaceutical composition comprising a compound according to the first aspect of the invention or a pharmaceutically acceptable salt or prodrug thereof, and a pharmaceutically acceptable carrier or excipient.

In a preferred embodiment, the pharmaceutical composition is in a dosage form suitable for oral administration, including but not limited to a tablet, a solution, a suspension, a capsules, a granule, a powder.

In a third aspect, the present invention provides the use of a compound according to the first aspect of the present invention or a pharmaceutically acceptable salt thereof, wherein said compound or a pharmaceutically acceptable salt thereof can be used for preparing a medicament for inhibiting DPP-4, a medicament for treating to preventing dipeptidyl peptidase-4 (DPP-4)-related diseases, or used as a diuretic or for preparing a medicament for treating and preventing inflammation.

In a preferred embodiment, the dipeptidyl peptidase-4 (DPP-4)-related diseases are diabetes, impaired glucose tolerance, intestinal disease, ulcerative colitis, Crohn's disease, obesity or metabolic syndrome.

In a further preferred embodiment, the diabetes is non-insulin dependent type 2 diabetes.

In a fourth aspect, the present invention provides a process for preparing a compound according to the first aspect of the present invention, comprising the steps of:

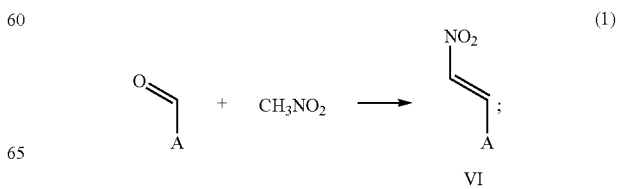

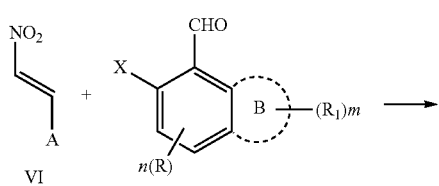

(2)

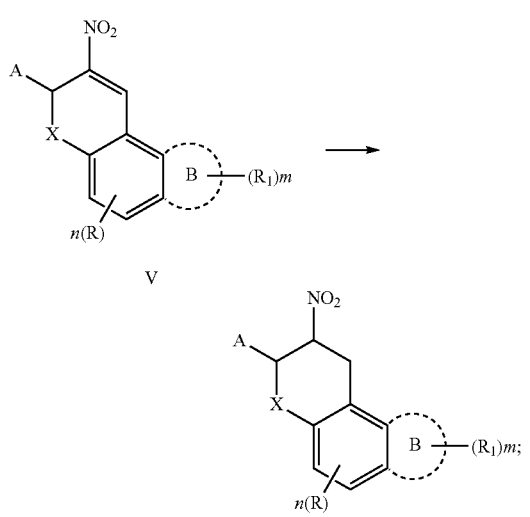

(3)

(4)

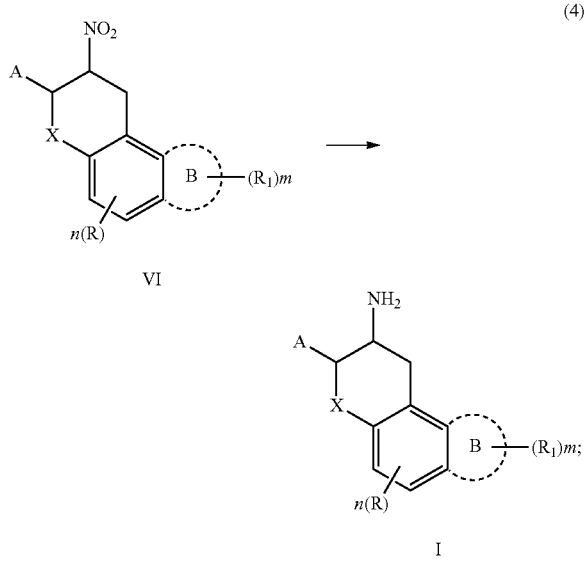

Wherein X, A, R, B, and $R_1$ are defined as above.

It should be understood that in the present invention, the technical features specifically above and below (such as the Examples) can be combined with each other, thereby constituting a new or preferred technical solution which needs not be individually described.

MODES FOR CARRYING OUT THE INVENTION

Through comprehensive and intensive research, the inventors unexpectedly found that a number of novel benzo six-membered ring derivatives with DPP-4 inhibitory activity, and upon evaluation of activity on molecular level, $IC_{50}$ values of the compounds of the present invention on DPP-4 were at nM level, thereby obtaining new DPP-4 inhibitors with novel structure and excellent activity. Upon animal experiments, it was found that the compounds of the present invention, as compared with compounds having similar activity in the prior art, can also have beneficial in vivo effects, such as excellent long-term efficacy.

Definition on Groups

The terms mentioned herein are further defined as follows:

As used herein, "alkyl" refers to a saturated straight chain or branched chain alkyl having 1 to 10 carbon atoms, and preferably alkyl includes an alkyl with 2-8 carbon atoms, 1-6 carbon atoms, 1-4 carbon atoms, 3-8 carbon atoms, 1-3 carbon atoms in length. Examples of alkyl include, but are not limited to, methyl, ethyl, n-propyl, iso-propyl, n-butyl, iso-butyl, heptyl, and the like.

Alkyl can be substituted by one or more (e.g., 2, 3, 4, or 5) substituents, for example substituted by a halogen or a haloalkyl. For example, alkyl may be an alkyl substituted by 1-4 fluorine atoms, or an alkyl substituted by fluorinated alkyl.

As used herein, "alkoxyl" refers to an oxy substituted by alkyl. A preferred alkoxyl is an alkoxyl with 1-6 carbon atoms in length, more preferably an alkoxyl with 1-4 carbon atoms in length. Examples of alkoxyl include, but are not limited to, methoxyl, ethoxyl, propoxyl and the like.

As used herein, "halogen atom" or "halogen" means fluorine, chlorine, bromine and iodine.

"Aryl" means a monocyclic, bicyclic or tricyclic aromatic group with 6 to 14 carbon atoms, and includes phenyl, naphthyl, phenanthryl, anthryl, indenyl, fluorenyl, tetralin, indanyl and the like. Aryl can be optionally substituted with 1-4 (e.g., 1, 2, 3, or 4) substituents selected from: a halogen, a $C_{1-4}$ aldehyde group, a $C_{1-6}$ alkyl, a cyano, a nitro, an amino, a hydroxyl, a hydroxymethyl, a halogen-substituted alkyl (e.g., trifluoromethyl), a carboxyl, a $C_{1-4}$ alkoxyl, a ethoxyformyl, $N(CH_3)$ and a $C_{1-4}$ acyl, a heterocyclyl or a heteroaryl, and the like.

As used herein, "aralkyl" refers to an alkyl substituted by an aryl, for example, a $C_{1-6}$ alkyl substituted by a phenyl. Examples of aralkyl include, but are not limited to, arylmethyl, arylethyl, etc., such as benzyl, phenethyl and the like.

For example, aryl can be substituted by 1-3 substituents selected from: a halogen, —OH, $C_{1-4}$ alkoxyl, $C_{1-4}$ alkyl, —$NO_2$, —$NH_2$, —$N(CH_3)_2$, a carboxyl, and ethoxyformyl and the like.

As used herein, "5- or 6-member saturated or unsaturated heterocycle" includes, but not limited to, heteroalicyclic or heteroaromatic rings containing from 1 to 3 heteroatoms selected from O, S and N, including (but not limited to) a furyl, a thienyl, a pyrrolyl, a pyrrolidinyl, a pyrazolyl, an imidazolyl, a triazolyl, an oxazolyl, a pyranyl, a pyridyl, a pyrimidinyl, a pyrazinyl, a piperidinyl, a morpholinyl and the like.

As used herein, "heteroaromatic ring" or "heteroaryl" means that the group comprises 5 to 14 ring atoms, and 6, 10, or 14 electrons are shared in the ring system. And the the contained ring atoms are carbon atoms and 1-3 heteroatoms optionally selected from O, N, S. Useful heteroaryl includes a piperazinyl, a morpholinyl, a piperidinyl, a pyrrolidinyl, a thienyl, a furyl, a pyranyl, a pyrrolyl, an imidazolyl, a pyrazolyl, a pyridyl, including, but not limited to, 2-pyridyl, 3-pyridyl and 4-pyridyl, a pyrazinyl, a pyrimidinyl and the like.

5- or 6-member heterocycle may be optionally substituted by 1-5 (e.g., 1, 2, 3, 4, or 5) substituents selected from: a halogen, a $C_{1-4}$ aldehyde group, a $C_{1-6}$ a straight chain or branched chain alkyl, a cyano, a nitro, an amino, a hydroxyl, a hydroxymethyl, a halogen-substituted alkyl (e.g., trifluoromethyl), a carboxyl, a $C_{1-4}$ alkoxyl, an ethoxyformyl, $N(CH_3)$ and a $C_{1-4}$ acyl.

As used herein, "optionally substituted" means that the group modified by the term can be optionally substituted by 1-5 (e.g., 1, 2, 3, 4, or 5) substituents selected from: a halogen, a $C_{1-4}$ aldehyde group, a $C_{1-6}$ straight chain or branched chain alkyl, a cyano, a nitro, an amino, a hydroxyl, a hydroxymethyl, a halogen-substituted alkyl (e.g., trifluoromethyl), a carboxyl, a $C_{1-4}$ alkoxyl, an ethoxyformyl, $N(CH_3)$ and a $C_{1-4}$ acyl.

The benzo six-membered ring derivative of the present invention is a compound of general formula I, or a pharmaceutically acceptable salt or prodrug thereof, or an optically active isomer or solvate thereof:

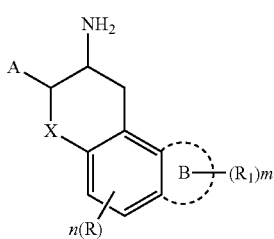

wherein

X is selected from $CH_2$, O, S and NH;

A is an unsubstituted benzene ring or a benzene ring with 1 to 5 substituents, wherein each substituent is independently selected from a halogen, a cyano, a hydroxy, a $C_{1-6}$ alkyl or a $C_{1-6}$ alkyl substituted by a halogen, preferably F, more preferably 1 to 5 F, a $C_{1-6}$ alkoxy or a $C_{1-6}$ alkoxy substituted by a halogen, preferably F, more preferably 1 to 5 F;

A may also be selected from nitrogen-containing, or sulfur-containing five-membered or six-membered saturated or unsaturated heterocycles with 1 to 4 substituents, wherein each substituent is independently selected from a halogen, a cyano, a boronic acid group;

A heterocycle is selected from the following structures:

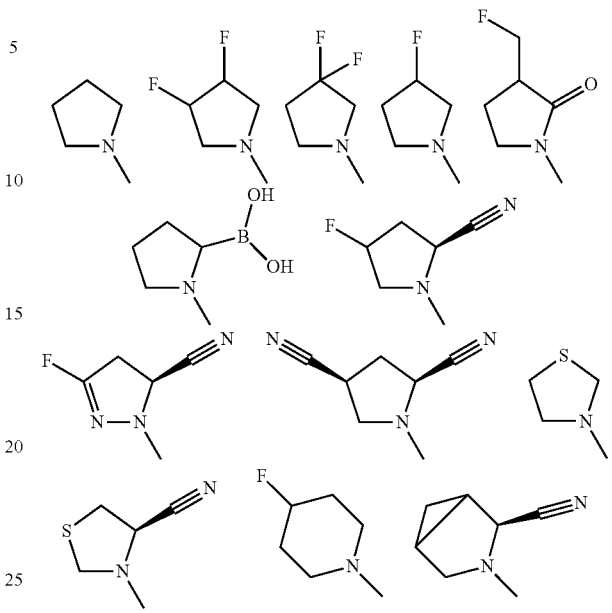

R is H, a halogen, a cyano, a hydroxy, a $C_{1-6}$ alkyl or $C_{1-6}$ alkyl with 1 to 5 F atoms, $C_{1-6}$ alkoxy or $C_{1-6}$ alkoxy with 1 to 5 F atoms, n=1-2;

Ring B is not present or is selected from an aromatic benzene ring, an aromatic heterocycle, a saturated or unsaturated 5-membered or 5-membered ring, a nitrogen-, oxygen- and sulfur-containing five- or six-membered saturated or unsaturated heterocycle, wherein the substituent $R_1$ is independently selected from the group consisting of a carbonyl, a halogen, a cyano, a hydroxy, a $C_{1-6}$ alkyl, a $C_{1-10}$ alkoxy (preferably a $C_{1-6}$ alkoxy), a $C_{2-10}$ alkoxy with alkenyl bond, alkynyl bond, an optionally substituted benzyloxy, a $C_{1-10}$ alkylcarbonyloxy, a $C_{1-3}$ alkoxymethoxy, a disubstituted $OCH_2CH_2O$ and $OCH_2O$, COOH, a $C_{1-6}$ alkoxycarbonyl, a carbamoyl, an amino, a $NR^2R^3$, a $C_{1-5}$ alkylcarboxamido, a $C_{3-5}$ alkyllactam group, a $C_{1-6}$ alkylsulfonamido, a $C_{3-5}$ alkylsultam group, a mercapto, a $C_{1-5}$ alkylmercapto, a $C_{1-5}$ alkylsulfonyl, a $C_{3-5}$ cycloalkylsulfonyl, a $C_{1-5}$ alkylsulfinyl, m=1 to 4;

$R^2$, $R^3$ are independently selected from a $C_{1-6}$ alkyl, or $R^2$ and $R^3$ together form a substituted or unsubstituted 5- or 6-membered cycloalkyl, or a substituted or unsubstituted 5- or 6-membered heterocycle group containing N, O.

In a particular embodiment, a compound of the present invention is a compound of general formula (II), or a pharmaceutically acceptable salt or prodrug thereof, or an optically active isomer or solvate thereof:

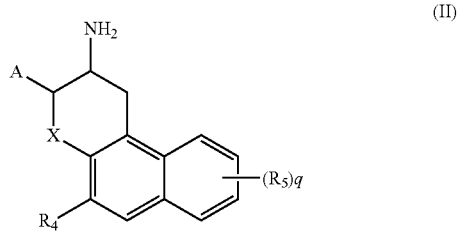

wherein

X is selected from $CH_2$, O, S and NH;

A is a benzene ring with 1 to 5 substituents, wherein each substituent is independently selected from a halogen, a cyano, a hydroxy, a $C_{1-6}$ alkyl or a $C_{1-6}$ alkyl substituted by a halogen, preferably F, more preferably 1 to 5 F, a $C_{1-6}$ alkoxy or a $C_{1-6}$ alkoxy substituted by a halogen, preferably F, more preferably 1 to 5 F;

$R^4$ is independently selected from H, a hydroxyl, F, a cyano;

$R^5$ is a halogen, a cyano, a hydroxyl, a mercapto, a $C_{1-6}$ alkyl group or a $C_{1-6}$ alkyl group containing 1 to 5 F atoms, a $C_{1-6}$ alkoxy, a $C_{1-3}$ alkoxymethyloxy, a hydroxyl, COOH, a $C_{1-6}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a $C_{1-6}$ alkylthio or a $C_{1-6}$ alkylthio containing 1 to 5 F atoms, a $C_{1-6}$ alkylsulfinyl, a $C_{1-6}$ alkylsulfonyl, an amino, an acetylamino, a methanesulfonamido, a methylcarbamido, a N-propanesulfonyllactam group, a N-butanesulfonyllactam group, a 4-morpholinyl, a N-methylpiperazin-4-yl, a piperazinyl, a 3-methanesulfonylpiperazinyl, a 3,3-difluorotetrahydropyrrolyl, a 2-aminoformylpiperidyl, a 3-pyrazolylamino, q=1-4.

In general formula (II), the chemical configurations are shown in IIa and IIb, where A and $NH_2$ are transconfigurations, and two chiral carbon atoms on saturated six-membered ring are labeled with *:

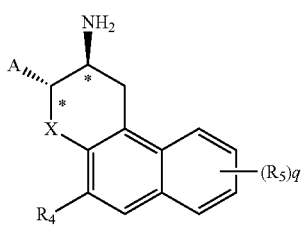

IIa

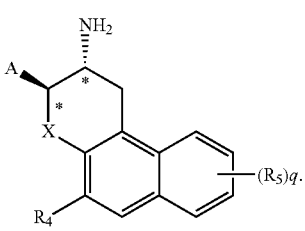

IIb

In a preferred embodiment, the absolute configuration is IIa.

In a particular embodiment, a compound of the present invention is a compound of general formula (III), or a pharmaceutically acceptable salt or prodrug thereof, or an optically active isomer or solvate thereof:

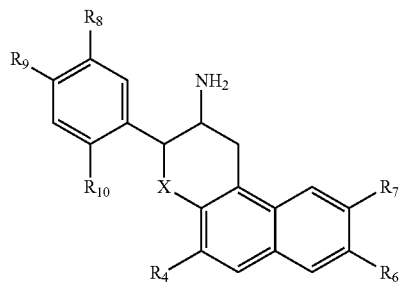

(III)

wherein,

X is selected from O, S and NH;

$R^4$ is independently selected from H, a hydroxyl;

$R^6$, $R^7$ are independently selected from a hydrogen, a halogen, a cyano, a hydroxy, a mercapto, a $C_{1-2}$ alkoxy, a $C_{1-2}$ alkylcarbonyloxy, a $C_{1-3}$ alkoxymethoxy, COOH, a $C_{1-2}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a methylthio, a methylsulfinyl, a methanesulfonyl, an amino, acetamido, methanesulfonamido, a methylcarbamido, N-propanesulfonyllactam group, N-butanesulfonyllactam group, a 4-morphinyl, a N-methylpiperazin-4-yl, a piperazinyl, a 3-methanesulfonylpiperazinyl, a 3,3-difluorotetrahydropyrrolyl, a 2-aminoformylpiperidyl, a 3-pyrazolylamino;

$R^8$, $R^9$ and $R^{10}$ are independently selected from H, Cl, F, a cyano.

The general method for preparing the compounds of the present invention is shown as follows:

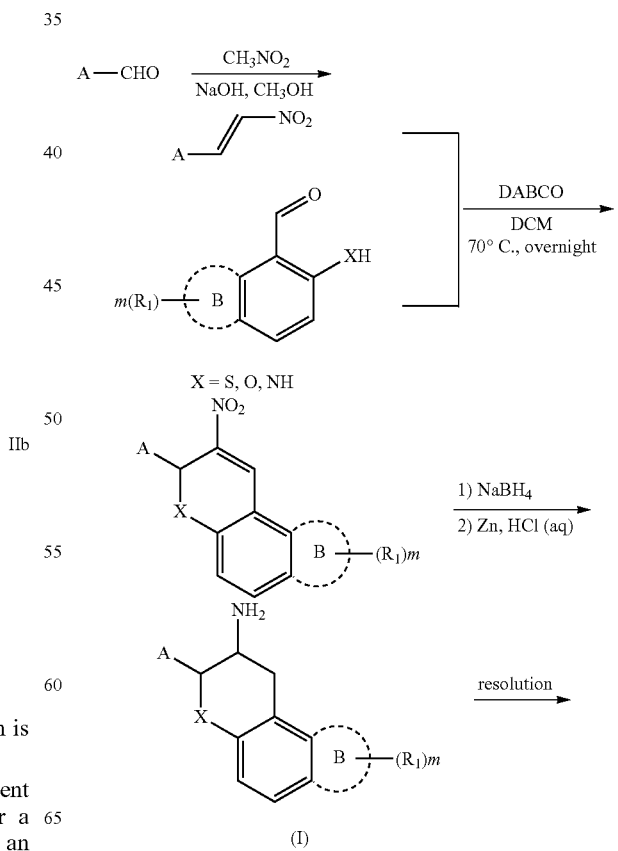

-continued
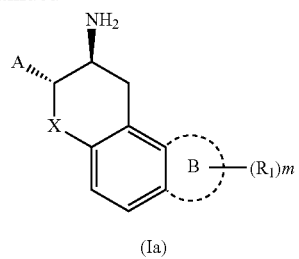
(Ia)
In a preferred embodiment, the compound of the present invention is shown as follows:
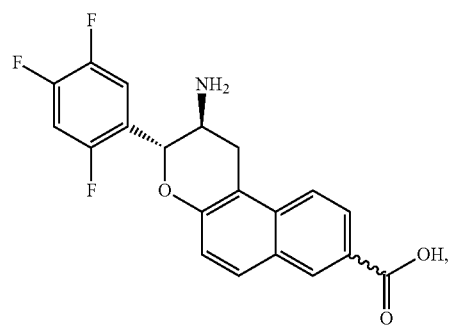
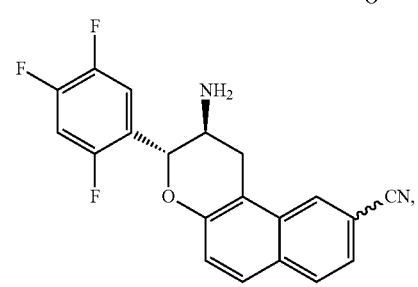
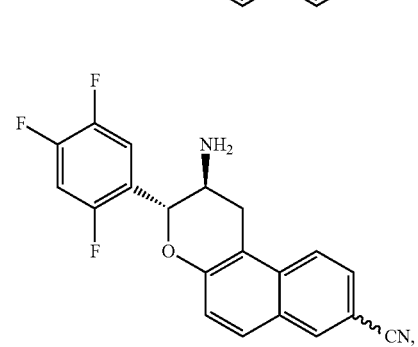
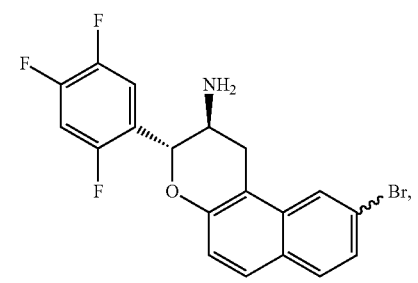
-continued
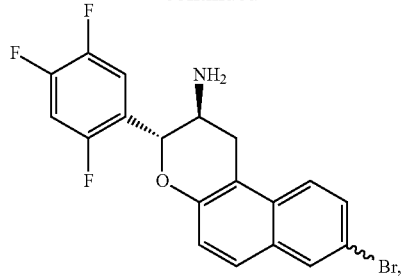
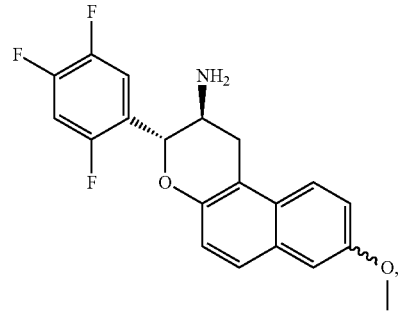
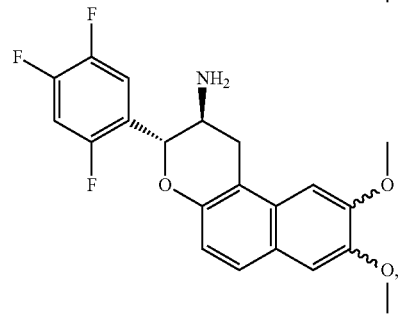
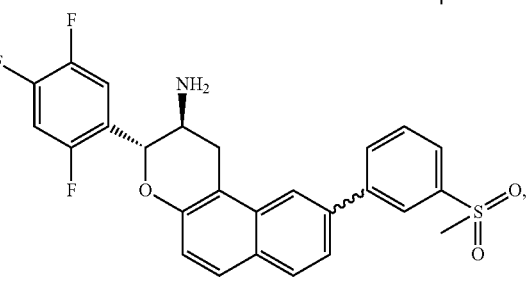
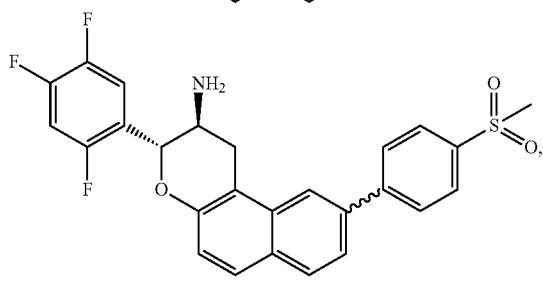

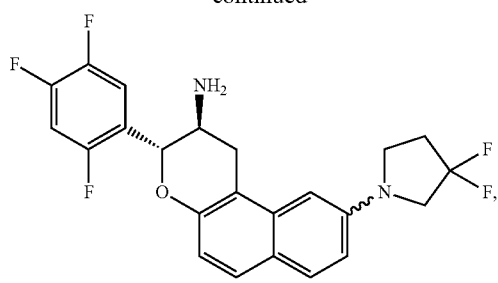
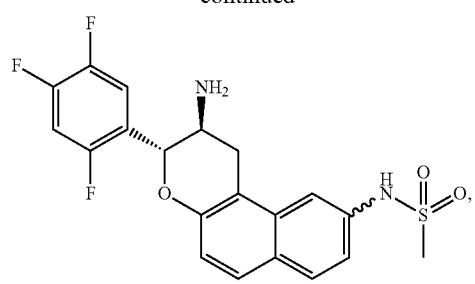
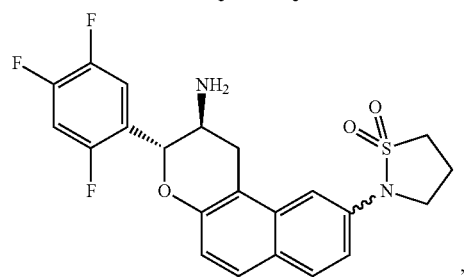
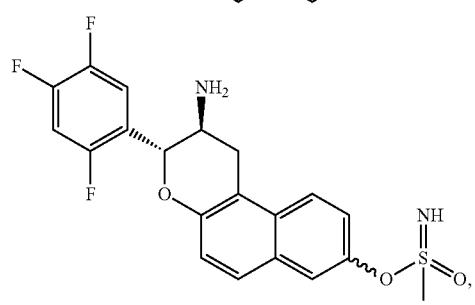
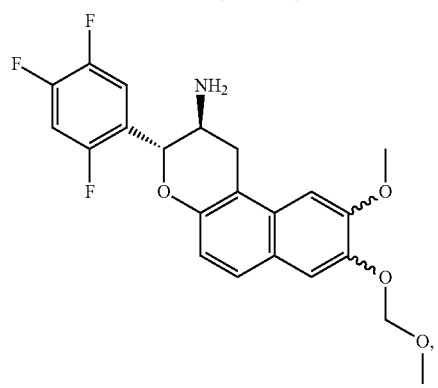
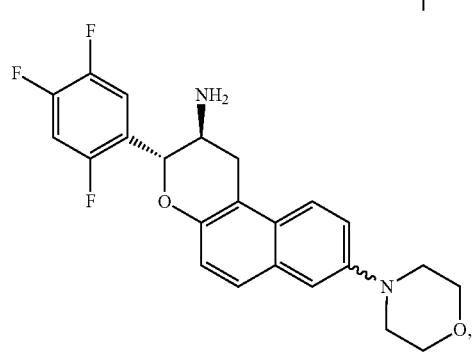
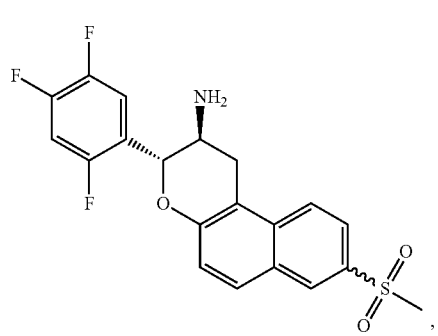
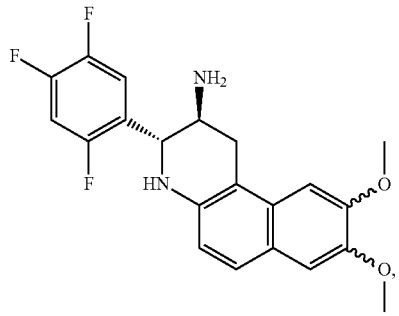
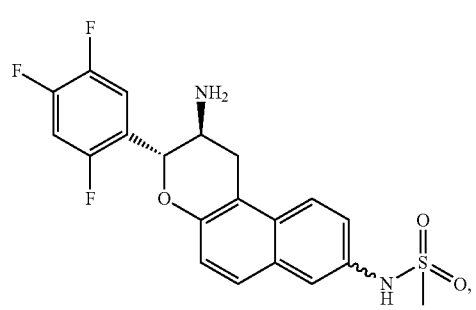
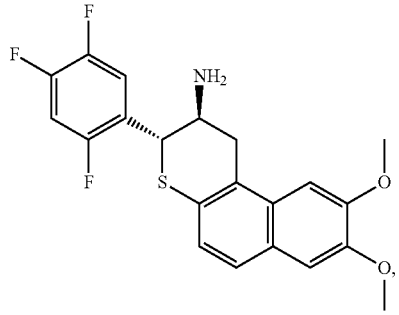

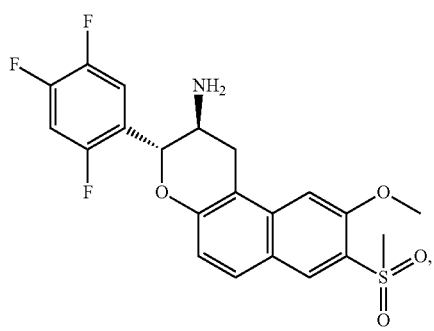
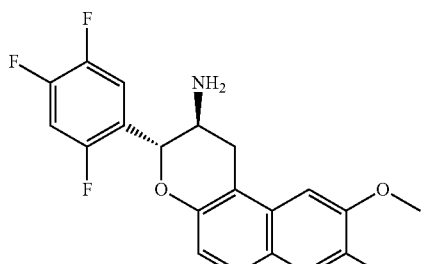
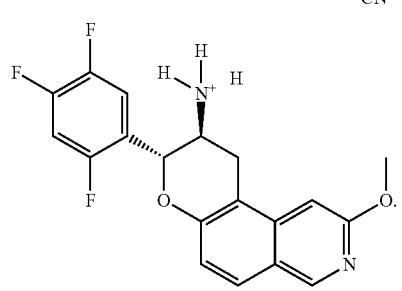
In other preferred embodiments, the present invention further provides the following compounds:
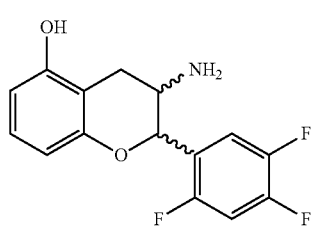 [SMILES: NC1Cc2c(O)cccc2OC1c1cc(F)c(F)cc1F]
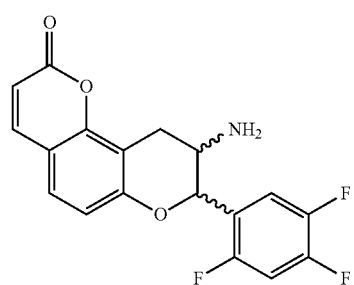 [SMILES: NC1Cc2c(ccc3ccc(=O)oc23)OC1c1cc(F)c(F)cc1F]
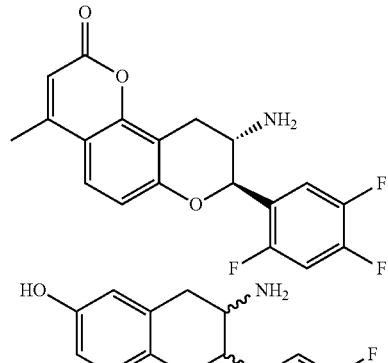
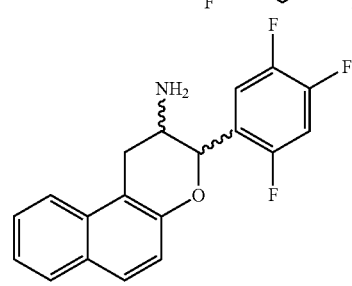
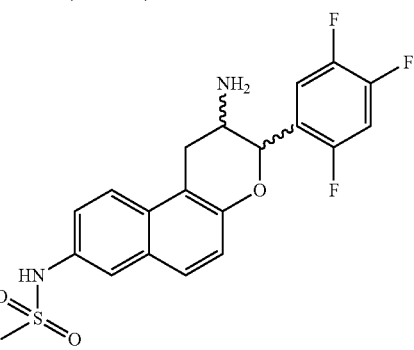
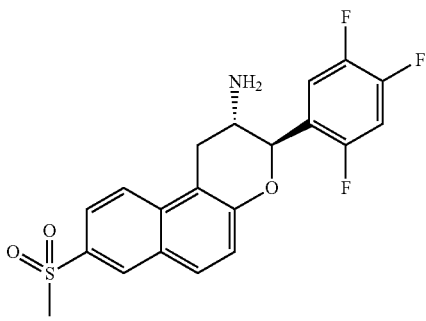

-continued

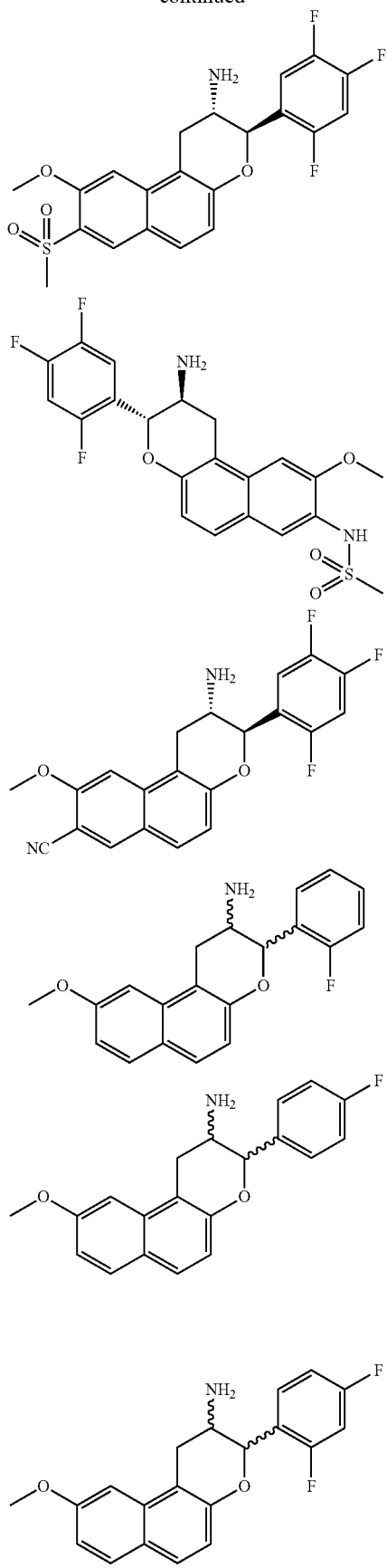

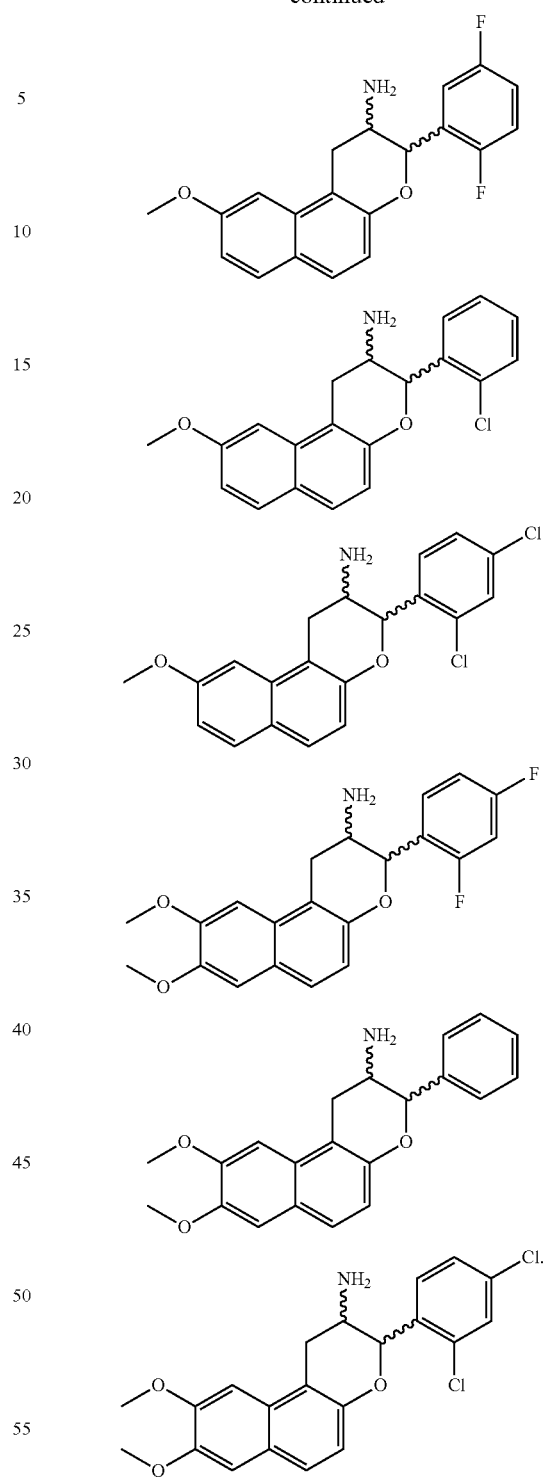

All of the compounds contain more than one chiral carbon atom and may exist in optical pure isomers and enantiomers, and the invention encompasses all forms.

In view of the teachings of the present invention and the knowledge in the prior art, a skilled person will recognize that functional groups of a compound of the present invention can be derivatized for obtaining derivatives which can be converted into a maternal compound in vivo.

The present invention also relates to a process for preparing a compound of the preceding general formulas (I) to (III), and the preparation method of (III) will be described as an example:

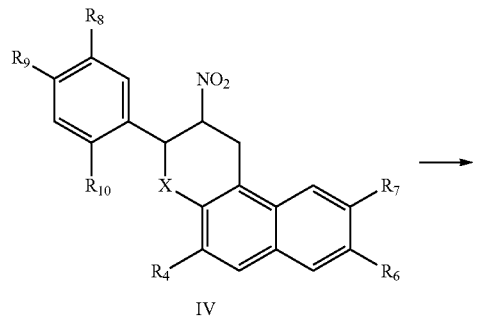

IV

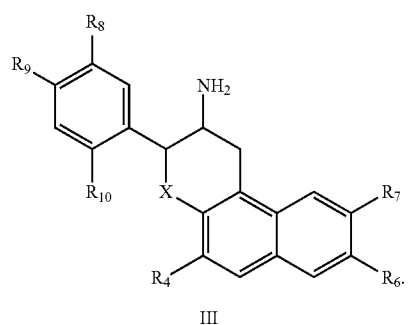

III

Amino compound (III) is reduced by a conventional reduction process, such as catalytic hydrogenation in a solvent such as methanol and ethanol; a catalyst, such as Raney nickel, metal Pd or metal platinum, etc., is used; conventional reduction conditions for a metal and acid and acid salt are used; commonly used metals include Zn, Fe; used acids include hydrochloric acid, sulfuric acid, acetic acid, and the acid salt is, for example, ammonium chloride and the like. The temperature for reduction reaction is 20~80° C.

V

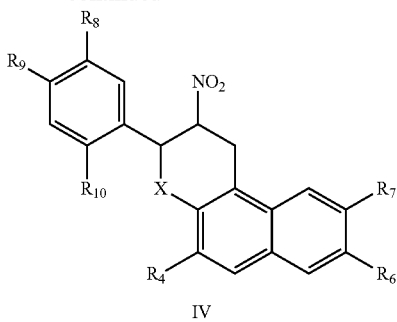

IV

Nitro compound (IV) is prepared by reduction of nitro-double bond compound (V), using sodium borohydride in a mixed solvent. The mixture is THF and methanol with a ratio of 20:1~1:1; and the temperature for reduction reaction is 20~80° C.

V

The preparation method for nitro-double bond compound (V) (X=S, O, NH, $CH_2$) is similar to Michael addition method, which is prepared from nitro-vinylbenzene (VI) and aldehyde group compound (VII) with electron-enriched group X at the corresponding ortho-position under neutral to alkaline conditions. The basic catalyst includes organic base triethylamine, diisopropylethylamine, trivinyl diamine, and metal base including Grignard reagent, butyl lithium, LDA and the like. The temperature for reaction is −80° C.~80° C.

+ $CH_3NO_2$ →

-continued

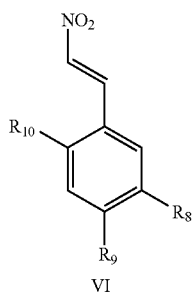

VI

Nitro-vinylbenzene (VI) is prepared by condensation of substituted benzaldehydes and nitromethane, and used bases include inorganic bases NaOH, KOH, and organic bases including triethylamine, diisopropylethylamine, trivinyl diamine.

Based on to the novel compounds of the present invention, the present invention also provides a pharmaceutical composition comprising a therapeutically effective amount of a compound of formula I, II or III of the present invention or a pharmaceutically acceptable salt thereof and a pharmaceutically acceptable carrier or excipient.

The examples of a pharmaceutically acceptable salt of the compound according to the present invention include, but are not limited to, an inorganic and organic acid salt, such as hydrochloride, hydrobromide, sulfate, citrate, lactate, tartrate, maleate, fumarate, mandelate and oxalate; and an inorganic and organic base salt formed with a base, such as sodium hydroxyl, Tris (hydroxymethyl) aminomethane (TRIS, amine tromethamine) and N-methyl glucamine.

Each person will have different requirements, but the optimal dosage of each active ingredient in the pharmaceutical composition of the present invention can be determined by a person skilled in the art.

The pharmaceutical composition of the present invention may be formulated into forms suitable for various routes of administration, including, but not limited to, for parenteral, subcutaneous, intravenous, intramuscular, intraperitoneal, transdermal, buccal, intrathecal, intracranial, nasal or topical routes of administration, for the treatment of DPP-4 related diseases. In a preferred embodiment, the compounds of the present invention are formulated in an oral dosage form. The administered amount is effective to ameliorate or eliminate one or more conditions. For the treatment of a particular disease, the effective amount is sufficient to ameliorate, or reduce the symptoms of diseases by some manner. Such doses may be administered as a single dose, or can be administered according to an effective treatment. The dose may cure the disease, but it is usually administered to improve the symptoms of the disease. Generally, repeated administration is required to achieve the desired improvement in symptoms. The dosage will be determined depending on the patient's age, health and weight, concurrent treatment, frequency of treatment, and the desired therapeutic effects.

Pharmaceutical formulations of the present invention may be administered to any mammal, as long as the therapeutic effects can be achieved. In mammals, the most important is human.

The compound of the present invention or a pharmaceutical composition thereof may be useful in the treatment or prevention of Dipeptidyl peptidase-4 (DPP-4) related diseases. In a specific embodiment, DPP-4-related diseases include diabetes, in particular non-insulin dependent type 2 diabetes, impaired glucose tolerance, intestinal disease, ulcerative colitis, Crohn's disease, obesity or metabolic syndrome. The compounds of the present invention may also be used as a diuretic or for the prevention and treatment of inflammation.

The pharmaceutical formulations of the present invention can be manufactured by a known method. For example, it can be manufactured by conventional mixing, granulating, dragee, dissolution, or freeze-drying process. During the manufacture of oral formulations, solid excipients and active compounds can be combined and optionally ground. If necessary, a suitable amount of auxiliary agent can be added, and the mixture of granules can be processed to obtain tablets or dragee cores.

Suitable excipients (especially fillers) are, for example, sugars such as lactose or sucrose, mannitol or sorbitol; cellulose preparations or calcium phosphates, for example tricalcium phosphate or calcium hydrogen phosphate; and binders, such as starch, including corn starch, wheat starch, rice starch, potato starch, gelatin, tragacanth, methyl cellulose, hydroxypropyl methyl cellulose, sodium carboxymethyl cellulose, or polyvinyl pyrrolidone. If desired, disintegrating agents can be added, for example, starches mentioned above as well as carboxymethyl starch, cross-linked polyvinylpyrrolidone, agar, or alginic acid or a salt thereof, such as sodium alginate. Adjuvants, especially flow modifiers and lubricants, e.g., silica, talc, stearic acid salts such as magnesium and calcium stearate, stearic acid or polyethylene glycol can be added. If necessary, suitable coatings resistant to gastric juices can be provided to the dragee core. For this purpose, concentrated sugar solutions may be applied. Such solution can contain gum arabic, talc, polyvinylpyrrolidone, polyethylene glycol and/or titanium dioxide, lacquer solutions, and suitable organic solvents or solvent mixtures. For the preparation of coatings resistant to gastric juices, an appropriate cellulose solution, for example cellulose acetate phthalate or hydroxypropylmethyl cellulose phthalate can be used. Dyestuffs or pigments may be added to the coating of tablets or dragee cores, for example, for identification or characterization of the dosage combinations of active ingredients.

Based on the compounds of the present invention, a skilled person will know that prodrugs of the compounds of the present invention should also be included within the scope of the present invention. As used herein, the term "prodrug" has the same meaning as commonly understood by a skilled person, that is, a compound having pharmacological activities is chemically modified to obtain a compound which is inactive or less active in vitro, and can release an active drug through enzymatic or non-enzymatic conversion in vivo, thereby exerting the efficacy. A prodrug itself is of no biological activity or few activities, and can be converted into an active substance through in vivo metabolism, thereby increasing bioavailability of drugs, enhancing targeting property, and reducing toxicity and side effects of the drug. In a specific embodiment, the prodrug of the compound of the present invention includes a derivative of ester, amide and the like obtained by chemically modifying the compounds of the present invention.

Based on a compound of the present invention and a pharmaceutical composition thereof, the present invention also provides a method for treating or preventing a dipeptidyl peptidase-4 (DPP-4) related disease, which includes, but not limited to, diabetes mellitus, especially non-insulin dependent 2-type diabetes mellitus, impaired glucose tolerance, intestinal disease, ulcerative colitis, Crohn's disease, obesity or metabolic syndrome. The method comprises administering to a subject in need thereof a compound of formula I, II or III of the present invention or a pharmaceutically acceptable salt thereof or a pharmaceutical composition of the invention.

Methods for administration include, but not limited to, various methods for administration well known in the art and can be determined according to the actual situation of a patient. Such methods include, but not limited to, parenteral, subcutaneous, intravenous, intramuscular, intraperitoneal, transdermal, oral, intrathecal, intracranial, nasal or topical routes.

Moreover, the present invention includes the use of a compound of formula I, II or III of the present invention or a pharmaceutically acceptable salt thereof in the preparation of a medicament for treating or preventing a dipeptidyl peptidase-4 (DPP-4) related disease, which includes, but not limited to, diabetes mellitus, especially non-insulin dependent 2-type diabetes mellitus, impaired glucose tolerance, intestinal disease, ulcerative colitis, Crohn's disease, obesity or metabolic syndrome; in the preparation of a medicament for inhibiting DPP-4; and in the preparation of a diuretic or a medicament for the prevention and treatment of inflammation.

Advantages of the Invention

1. The compound of the present invention is a DPP-4 inhibitor with novel structure;
2. The compound of the present invention possesses excellent inhibitory activities against DPP-4;
3. The compounds of the present invention can replace the existing hypoglycemic drugs, and have great prospects of industrialization and commercialization and market value, and significant economic benefits.

The present invention will be illustrated in the following referring to the specific examples; however, the present invention is not limited to such examples. For the experimental methods in the following examples the specific conditions of which are not specifically indicated, they are performed under routine conditions or manufacturer's instruction. All the percentages or fractions refer to weight percentage and weight fraction, unless stated otherwise.

EXAMPLE 1. trans-(2RS, 3RS)-3-amino-2-(2,4,5-trifluorophenyl)chroman-5-ol (Compound-1)

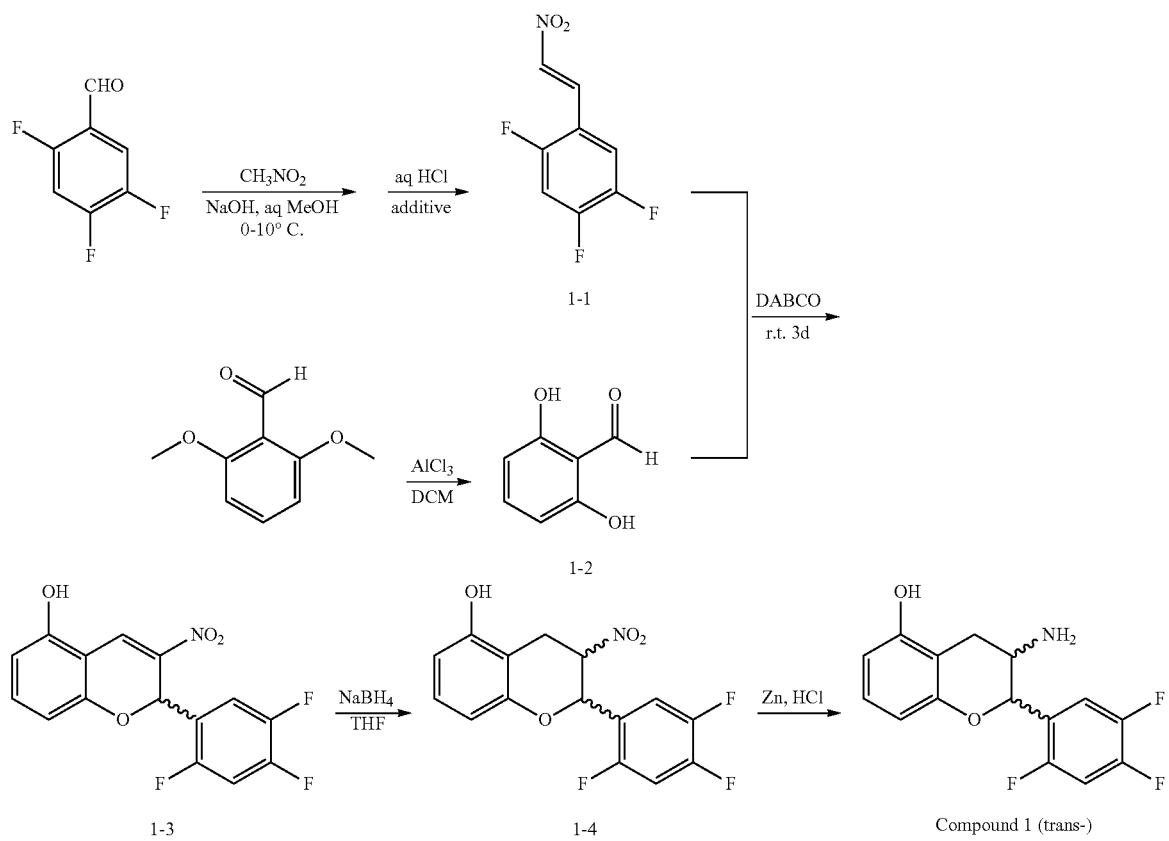

Synthesis of Intermediate 1-1

2,4,5-trifluorobenzaldehyde (10 g, 62.46 mmol), nitromethane (4 mL) and methanol (10 mL) were prepared into a solution. Methanol (60 mL), water (30 mL), sodium hydroxide (2.5 N, 30 mL) were prepared into a solution, and maintained at 5° C. The former solution was added dropwise to the latter solution over about 30-60 mins, and the temperature of the solution was maintained at 5-10° C. Upon addition, the above obtained solution was added dropwise to a mixture solution of zinc chloride (42.6 g, 31.25 mmol), concentrated hydrochloric acid (13 mL) and water (17 mL), and the temperature was maintained at 0 to 10° C. during addition. Upon addition, the reaction was carried out at room temperature for 2-4 h. After the reaction, the reaction system was filtered by suction under reduced pressure, and the filter cake was washed with 40% methanol solution for several times to obtain the product 9.8 g (yield 77%). GC-MS: 203.

¹H-NMR (400 MHz, CDCl₃): δ 7.95 (d, J=14.0 Hz, 1H), 7.65 (d, J=14.0 Hz, 1H), 7.36 (d, J=7.2 Hz, J=16.0 Hz, 1H), 7.09 (d, J=6.4 Hz, J=16.0 Hz, 1H).

Synthesis of Intermediate 1-2

AlCl₃ (82.9 g, 600 mmol) was weighed into a 1 L round bottom flask, dissolved in 500 mL of dichloromethane and stirred at room temperature. 2,6-dimethoxybenzaldehyde (19.92 g, 120 mmol) was dissolved in 200 ml of dichloromethane and slowly added dropwise to the above-mentioned round bottom flask dropwise (for 1 h). Upon addition, the mixture was stirred for 12 h. The reaction was monitored by TLC, and quenched by adding diluted hydrochloric acid (2 mol/L, 600 mL). The organic phase was separated and the aqueous phase was extracted with ethyl acetate. The organic phases were combined, dried over anhydrous sodium sulfate, and filtered. The solvents were removed in vacuo, and the residue was separated through column chromatography (PE:EA=9:1) to give 12.5 g of yellow solids in 78.3% yield. GC-MS, 138.

¹H-NMR (400 MHz, CDCl₃): δ 10.37 (s, 1H), 7.32 (t, J=8.4 Hz, 1H), 7.26 (s, 1H), 6.41 (d, J=8.0 Hz, 1H).

Synthesis of Intermediate 1-3

Intermediate 1-1 (0.88 g, 4 mmol) and intermediate 1-2 (0.5 g, 3.6 mmol) were weighed in a 50 ml round bottom flask, and dissolved by adding dioxane (15 mL). And DABCO (0.2 g, 1.8 mmol) was added in an atmosphere of argon. The reaction mixture was stirred at room temperature for 24 hrs, and monitored by TLC until the raw compound 5 was totally consumed. The reaction was quenched with saturated ammonium chloride solution (30 mL) and extracted with ethyl acetate (3*30 ml). The organic phase was washed with saturated brine and dried over anhydrous sodium sulfate. And the solvents were removed in vacuo. The crude product was separated through flash column chromatography (PE:EA=4:1) to give 230 mg of a dark yellow oil (yield 19.6%). GC-MS, 323.

¹H-NMR (400 MHz, CDCl₃): δ 10.94 (s, 1H), 8.36 (s, 1H), 7.70 (m, 1H), 6.46 (m, 1H), 7.21 (t, J=8.4 Hz, 1H), 6.80 (s, 1H), 6.54 (d, J=8.4 Hz, 1H), 6.32 (d, J=8.0 Hz, 1H).

Synthesis of Intermediate 1-4

Intermediate 1-3 (3.2 g, 10 mmol) was weighed in a 500 mL round bottom flask, dissolved by adding 220 ml of THF/CH₃OH (10:1) and magnetically stirred. Sodium borohydride (NaBH₄) (490 mg, 13 mmol) was stirred at room temperature for 20 mins. After reaction, 10 ml of water was added to quench the reaction. The solvents were removed in vacuo, and then 100 ml of water was added. The obtained mixture was extracted with ethyl acetate, dried over anhydrous sodium sulfate, and separated through column chromatography (PE:EA=10:1) to give 1.4 g of pale yellow solids (43.7% yield).

¹H-NMR (400 MHz, DMSO-d6): δ 9.89 (s, 1H), 7.73-7.64 (m, 2H), 7.00 (t, J=8.0 Hz, 1H), 6.51 (d, J=7.6 Hz, 1H), 6.40 (t, J=8.0 Hz, 1H), 5.71 (d, J=8.0 Hz, 1H), 5.64-5.59 (m, 1H), 3.31 (dd, J=8.8 Hz, J=16.8 Hz, 1H), 3.22 (dd, J=5.6 Hz, J=16.8 Hz, 1H).

Synthesis of (2RS, 3RS)-3-amino-2-(2,4,5-trifluorophenyl)chroman-5-ol (compound-1)

Compound 6 (325 mg, 1 mmol) and zinc powder (780 mg, 12 mmol) were weighed into 10 mL of ethanol. A solution of 6N hydrochloric acid (3.2 mL) was added for 1 hour. After completion of the reaction, the filtrate was neutralized with saturated sodium bicarbonate to pH=8 and the aqueous phase was extracted with ethyl acetate. The organic phase was dried over anhydrous sodium sulfate and separated by column chromatography (PE:EA=2:1) to give a white solid powder (yield 77.9%).

¹HNMR (400 MHz, DMSO-d6): δ 9.50 (s, 1H), 7.61-7.53 (m, 2H), 6.88 (t, J=8.0 Hz, 1H), 6.40 (d, J=8.0 Hz, 1H), 6.26 (t, J=8.0 Hz, 1H), 4.74 (d, J=9.2 Hz, 1H), 3.23-3.17 (m, 1H), 2.93 (dd, J=5.2 Hz, J=16.4 Hz, 1H), 2.36 (dd, J=10.4 Hz, J=16.4 Hz, 1H). LCMS (M+1)+ 296.06.

2. trans-(8RS,9RS)-9-amino-8-(2,4,5-trifluorophenyl)-9,10-dihydropyran[2,3-f]chroman-2(8H)-one (compound-2)

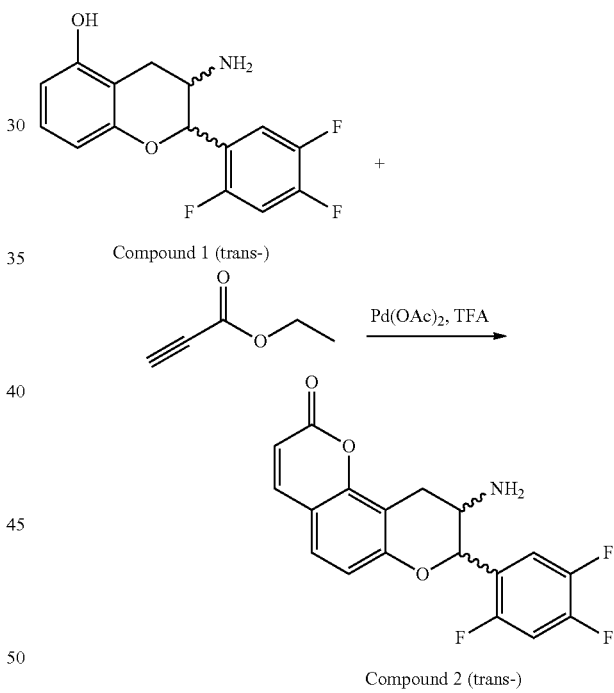

Compound 7 (117 mg, 0.6 mmol) was added into trifluoroacetic acid (1 mL), Pd(OAc)₂ (1.68 mg, 0.0075 mmol) and ethyl propiolate (117 mg, 1.8 mmol) were added and stirred for 5 mins in an ice bath. And then the mixture was stirred at room temperature for 22 h. After the reaction, the mixture was neutralized with 10% sodium bicarbonate solution. The aqueous phase was extracted with ethyl acetate. The organic phase was dried over anhydrous sodium sulfate, and the solvents were removed in vacuo. The obtained residue was separated through column chromatography to give 35 mg of white solid powder (Yield 18.5%).

¹H-NMR (400 MHz, DMSO-d6): δ 8.00 (d, J=9.2 Hz, 1H), 7.69-7.60 (m, 2H), 7.49 (d, J=8.4 Hz, 1H), 6.86 (d, J=8.4 Hz, 1H), 6.31 (d, J=9.2 Hz, 1H), 4.96 (d, J=9.2 Hz,

1H), 3.30 (m, 1H), 3.17 (dd, J=5.6 Hz, J=16.8 Hz, 1H), 2.65 (dd, J=10.4 Hz, J=16.8 Hz, 1H), 1.72 (m, 2H). LCMS (M+1)+348.18.

3. (8R,9S)-9-amino-4-methyl-8-(2,4,5-trifluorophenyl)-9,10-dihydropyran[2,3-f]-chroman-2(8H)-one (compound-3)

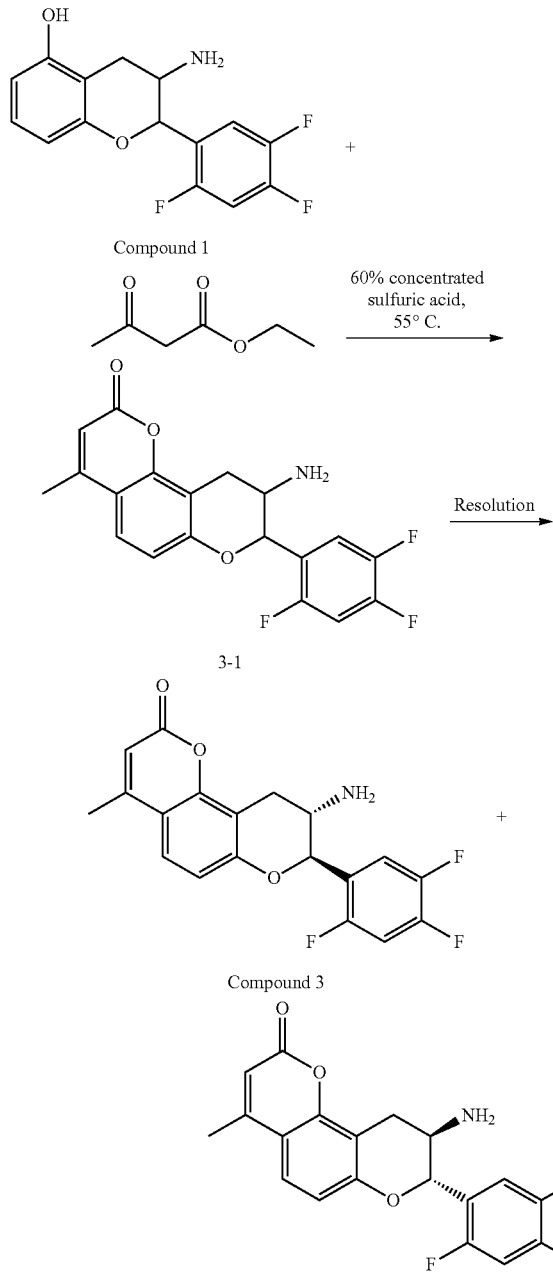

Compound 7 (1.7 g, 5.26 mmol) was weighed into a 100 ml round bottom flask and dissolved in 50 ml of 60% sulfuric acid solution. Ethyl acetoacetate (2.55 g, 23.67 mmol) was added and then the obtained mixture was stirred at 55° C. for 24 hrs. After the reaction was completed, 40 mL of ice-water mixture was added, neutralized with saturated sodium bicarbonate, extracted with ethyl acetate, and separated by column chromatography (CH₃OH:CH₂Cl₂=1:8) to give 1.02 g of white powder in a yield of 54%.

¹HNMR (400 MHz, DMSO-d6): δ7.68-7.59 (m, 2H), 7.55 (d, J=8.8 Hz, 1H), 6.88 (d, J=8.8 Hz, 1H), 6.23 (s, 1H), 4.96 (d, J=9.2 Hz, 1H), 3.39-3.34 (m, 1H), 3.17 (dd, J=5.6 Hz, J=16.8 Hz, 1H), 2.67 (dd, J=10.0 Hz, J=16.8 Hz, 1H). LCMS (M+1)+ 362.04.

Compound-3 was obtained through resolution by using a chiral column.

4. trans-(2RS,3RS)-3-amino-2-(2,4,5-trifluorophenyl)-chroman6-ol (compound-4)

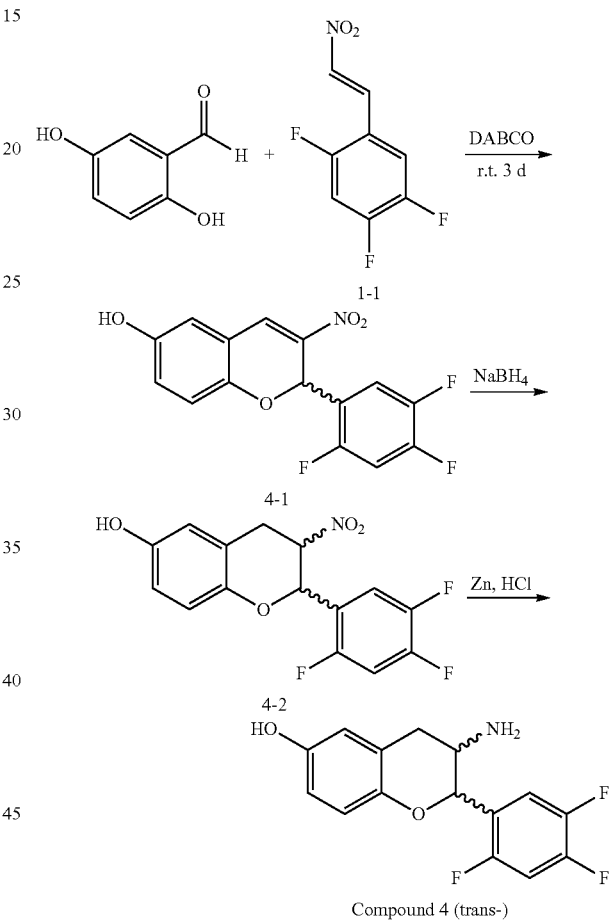

Synthesis of Intermediate 4-1

2,5-dihydroxybenzaldehyde (1.08 g, 10 mmol), intermediate 1-1 (6.09 g, 30 mmol), DABCO (0.56 g, 5 mmol) were weighed into a 25 ml round bottom flask, and stirred in an atmosphere of argon at 60° C. overnight to give 2.4 g of red solids in a yield of 74%.

¹H-NMR (400 MHz, DMSO-d6): δ 9.14 (s, 1H), 7.72-7.65 (m, 2H), 7.76-6.74 (m, 2H), 6.61-6.60 (m, 2H), 5.66 (d, J=7.6 Hz, 1H), 5.63-5.58 (m, 1H), 3.51 (dd, J=8.4 Hz, J=12.4 Hz, 1H), 3.3 (d, J=5.6 Hz, 1H).

Synthesis of Intermediate 4-2

4-1 (167 mg, 0.5 mmol) was weighed into a 25 mL round bottom flask, dissolved in 27.5 mL of THF/CH₃OH (10:1), and stirred at room temperature. Sodium borohydride was added in baech and stirred for another 20 mins. After completion of the reaction, 0.1 ml of water was added to quench the reaction, the solvent was removed under reduced pressure, and 2 ml of saturated ammonium chloride solution was added, extracted with ethyl acetate and separated by column chromatography (PE:EA=5:1) to give 50 mg of red solids in a yield of 31%.

$^1$H-NMR (400 MHz, DMSO-d6): δ 9.14 (s, 1H), 7.72-7.65 (m, 2H), 7.76-6.74 (m, 2H), 6.61-6.60 (m, 2H), 5.66 (d, J=7.6 Hz, 1H), 5.63-5.58 (m, 1H), 3.51 (dd, J=8.4 Hz, J=12.4 Hz, 1H), 3.3 (d, J=5.6 Hz, 1H).

Synthesis of (2RS, 3RS)-3-amino-2-(2,4,5-trifluorophenyl)-chroman6-ol (compound-4)

4-2 (975 mg, 3 mmol) and Zn powder (2.34 g, 36 mmol) were weighed into 11 ml of ethanol, and 11 ml of 6N HCl solution was added with stirring. The reaction was performed for 1 h, and then the reaction solution was neutralized with saturated sodium bicarbonate solution, extracted by ethyl acetate, and dried over anhydrous sodium sulfate. The solution was evaporated to dryness in vacuo and separated through column chromatography (PE:EA=1:1) to give 439 mg of product in a yield of 49.6%.

$^1$H-NMR (400 MHz, DMSO-d6): δ 9.50 (s, 1H), 7.61-7.53 (m, 2H), 6.88 (t, J=8.0 Hz, 1H), 6.40 (d, J=8.0 Hz, 1H), 6.26 (t, J=8.0 Hz, 1H), 4.74 (d, J=9.2 Hz, 1H), 3.23-3.17 (m, 1H), 2.93 (dd, J=5.2 Hz, J=16.4 Hz, 1H), 2.36 (dd, J=10.4 Hz, J=16.4 Hz, 1H). LCMS (M+1)+ 296.11.

5. (2S,3R)-9-methoxy-3-(2,4,5-trifluorophenyl)-2,3-dihydro-1H-benzo[f]-chroman-2-amine (compound-5)

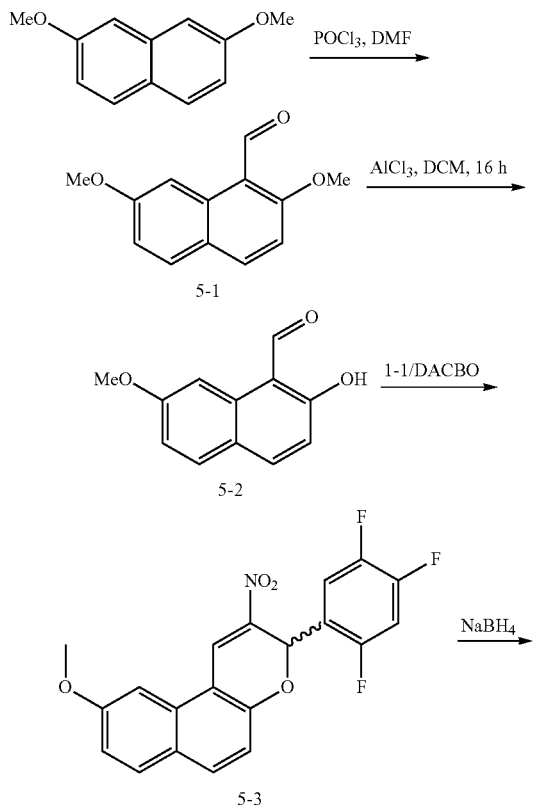

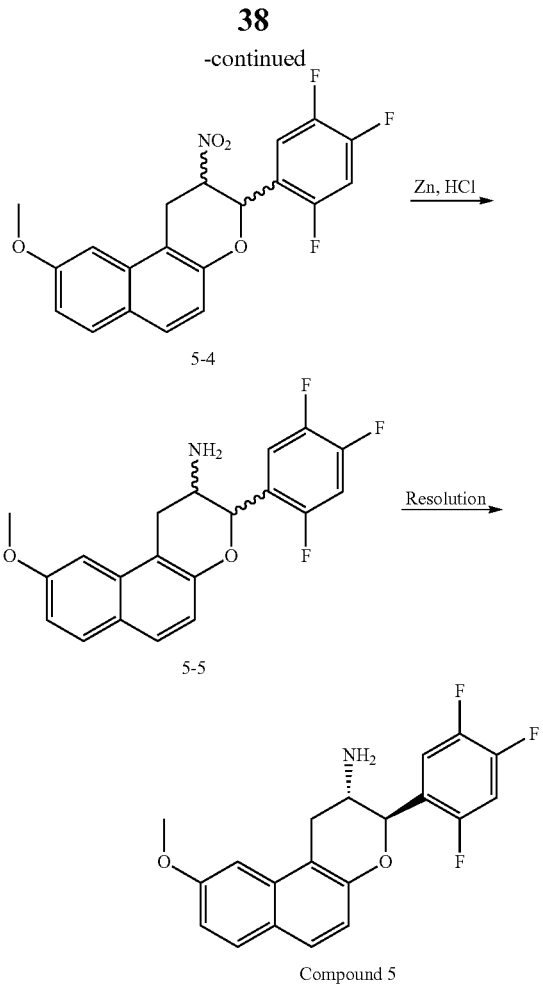

Compound 5

Synthesis of Intermediate 5-1

Compound 2,7-dimethoxynaphthalene (870 mg, 4.62 mmol) was weighed into 2 mL of DMF. POCl$_3$ (796 mg, 5.2 mmol) was added, and stirred overnight at 60° C. to form a brown solution. After completion of the reaction, 20 ml of ice water was added and the mixture was stirred overnight at room temperature. After completion of the reaction, the reaction mixture was filtered and the cake was recrystallized in methanol to obtain 690 mg of gray crystals (yield 75.5%). LC-MS: 217.10 (M+1)+.

$^1$H-NMR (400 MHz, DMSO-d6): δ 10.76 (s, 1H), 8.69 (d, J=2.0 Hz, 1H), 8.22 (d, J=8.8 Hz, 1H), 7.87 (d, J=9.2 Hz, 1H), 7.40 (d, J=9.2 Hz, 1H), 7.12 (d, J=9.2 Hz, J=1.6 Hz 1H), 4.04 (s, 3H), 3.88 (s, 3H).

Synthesis of Intermediate 5-2

2,7-dimethoxy-1-naphthaldehyde (6.0 g, 27.9 mmol) was weighed into 45 ml of dry dichloromethane. AlCl$_3$ (11.1 g, 83.4 mmol) was added in portions and stirred for 16 h at room temperature. After completion of the reaction, the reaction solution was poured into 150 ml of brine and extracted by ethyl acetate extract (2*150 ml). The organic phase was washed with brine for two times (2*150 ml), dried over anhydrous sodium sulfate and dried under vacuum to dryness to solids which were recrystallize in ethanol to give 3.2 g of pale yellow crystals (Yield 61.3%). LC-MS: 203.05 (M+1)+, 201.05 (M-1)-.

¹H-NMR (400 MHz, DMSO-d6): δ 11.93 (s, 1H), 10.81 (s, 1H), 8.46 (d, J=2.0 Hz, 1H), 8.04 (d, J=8.8 Hz, 1H), 7.79 (d, J=8.8 Hz, 1H), 7.09-7.04 (m, 2H), 3.89 (s, 3H), 4.04 (s, 3H), 3.88 (s, 3H).

Synthesis of Intermediate 5-3

Compound 7-methoxy-2-hydroxy-1-naphthaldehyde (101 mg, 0.5 mmol), intermediate 1-1 (506 mg, 2.5 mmol, 5 eq), DABCO (56 mg, 0.5 mmol) were weighed into a 50 ml of round bottom flask. The mixture was heated to 80° C. under argon atmosphere and stirred overnight. After completion of the reaction, 20 ml of methylene chloride was added and 51 mg of pale yellow solids were directly obtained by column chromatography (PE:EA=6:1) in a yield of 26.4%. LC-MS: 388.10 (M+1)⁺.

¹H-NMR (400 MHz, CDCl₃): δ 8.82 (s, 1H), 7.78 (d, J=8.8 Hz, 1H), 7.69 (d, J=8.8 Hz, 1H), 7.34 (d, J=2.0 Hz, 1H), 7.12 (dd, J=2.4 Hz, J=8.8 Hz, 1H), 7.07-6.99 (m, 2H), 6.98 (s, 1H), 6.90 (d, J=9.2 Hz, 1H), 4.04 (s, 3H).

Synthesis of Intermediate 5-4

Compound 5-3 (38.7 mg, 0.1 mmol) was weighed into a 10 mL round bottom flask, and 5.5 mL of a mixture of THF/CH₃OH (10:1) was added for dissolving the compound. Sodium borohydride (10 mg, 0.26 mmol) was added and magnetically stirred at room temperature for 20 mins. After completion of the reaction, a small amount of water was added to quench the reaction. The solvent was removed in vacuo and 10 ml of saturated ammonium chloride solution was added, extracted with ethyl acetate and dried over anhydrous sodium sulfate to give 20 mg of off-white solids in a yield of 51.4%.

¹H-NMR (400 MHz, CDCl₃): δ 7.73 (d, J=9.2 Hz, 1H), 7.66 (d, J=9.6 Hz, 1H), 7.31-7.25 (m, 1H), 7.10 (dd, J=2.4 Hz, J=8.8 Hz, 1H), 7.05-6.98 (m, 3H), 5.75 (d, J=8.4 Hz, 1H), 5.31-5.26 (m, 1H), 3.94 (s. 3H), 3.85 (dd, J=8.4 Hz, J=16.4 Hz, 1H), 3.55 (d, J=6.0 Hz, J=16.4 Hz, 1H).

Synthesis of (2S,3R)-9-methoxy-3-(2,4,5-trifluorophenyl)-2,3-dihydro-1H-benzo[f]-chroman-2-amine (compound-5)

Intermediate 5-4 (233.4 mg, 0.6 mmol), Zn powder (468 mg, 7.2 mmol) were weighed in 3.4 ml of ethanol, and 6N HCl solution (2 ml) was added with stirring. The reaction was performed at 50° C. for 1 h. Afterwards, the reaction solution was neutralized with saturated sodium bicarbonate solution, extracted with ethyl acetate, and dried over anhydrous sodium sulfate. The solution was evaporated to dryness in vacuo, and the residue was separated by column chromatography (PE:EA=1:1) to give 49 mg of product in a yield of 22.8%. Compound 5 was obtained through resolution by using a chiral column. LC-MS: 360.10 (M+1)⁺.

¹H-NMR (400 MHz, DMSO-d6): δ 7.91-7.84 (m, 1H), 7.80 (d, J=8.8 Hz, 1H), 7.68 (d, J=8.4 Hz, 1H), 7.64-7.62 (m, 1H), 7.17 (dd, J=4.0 Hz, J=1.6 Hz, 1H), 7.07 (dd, J=2.4 Hz, J=6.4 Hz, 1H), 6.95 (d, J=8.8 Hz, 1H), 5.48 (d, J=9.6 Hz, 1H), 5.08-5.01 (m, 1H), 3.77 (dd, J=16.4 Hz, J=10.8 Hz, 1H), 3.55 (d, J=5.6 Hz, J=16.4 Hz, 1H).

6. (2S,3R)-8-methyoxy-3-(2,4,5-trifluorophenyl)-2,3-dihydro-H-benzo[f]-chroman-2-amine (compound-6)

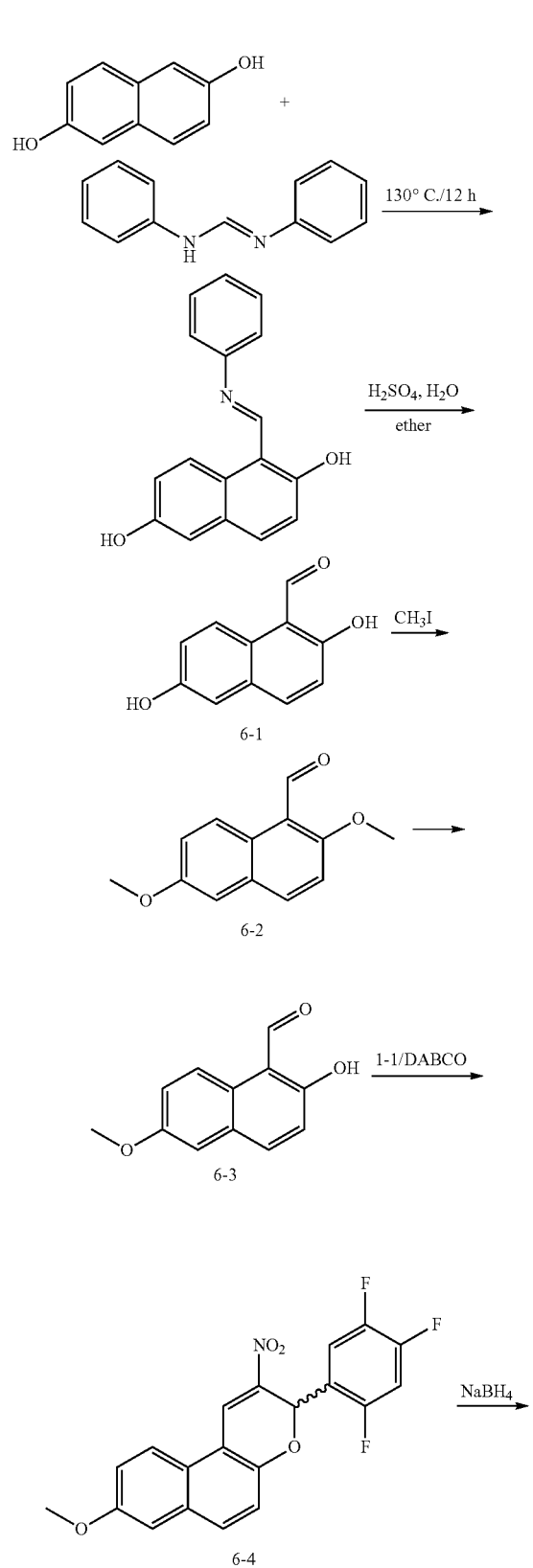

-continued

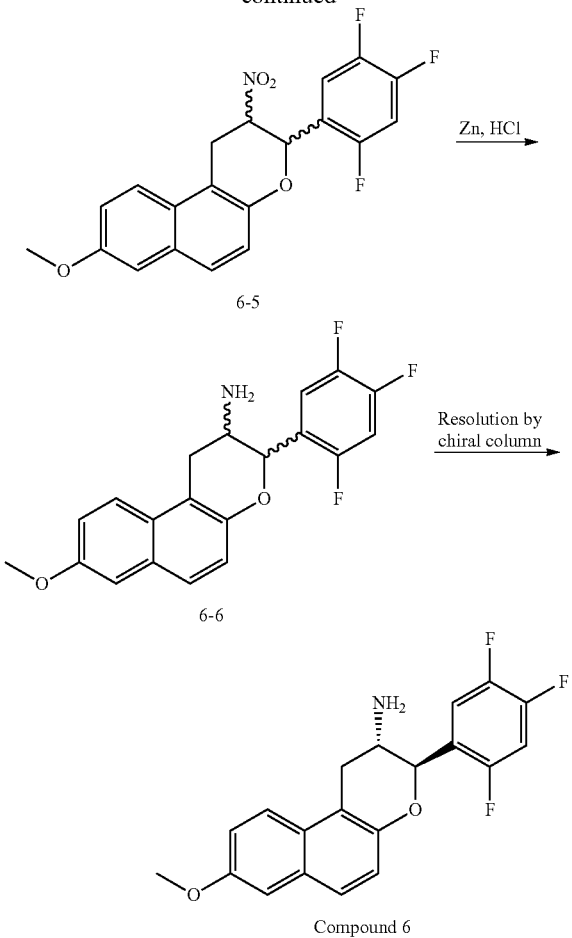

Synthesis of Intermediate 6-1

2,6-dihydroxynaphthalene (5 g, 31.2 mmol) and dibenzoformamidine (8.7 g, 44.35 mmol) were weighed and stirred under argon for 5 h at 130° C. The reaction was monitored by TLC, and after cooled to room temperature, 30 ml of acetone was added. Precipitates were filtered and dried to give a red powder. 5.5 g of red solid powder was obtained in a yield of 70%.

$^1$H-NMR (400 MHz, DMSO-d6): δ 15.37 (d, J=3.2 Hz, 1H), 8.46 (d, J=2.0 Hz, 1H), 9.60 (d, J=2.8 Hz, 1H), 9.53 (s, 1H), 8.37 (d, J=10.0 Hz, 1H), 7.78 (d, J=7.2 Hz, 1H), 7.59 (d, J=7.6 Hz, 2H), 7.49 (t, J=7.6 Hz, J=8.0 Hz, 2H), 7.31 (t, J=7.6 Hz, J=7.2 Hz, 1H), 7.11 (m, 2H), 6.98 (d, J=10.2 Hz, 1H).

The above compound (6 g, 22.8 mmol) was weighed into to 5 ml of water and 4 ml of concentrated sulfuric acid. 80 ml of ether was added and stirred at room temperature for 4 days. The upper layer of ether was separated and extracted with ether for several times. The organic phases were combined and the solvent was removed in vacuo to obtain yellow solids in a yield of 35%.

$^1$H-NMR (400 MHz, DMSO-d6): δ 10.76 (s, 1H), 8.78 (d, J=8.8 Hz, 1H), 7.94 (d, J=9.2 Hz, 1H), 7.19-7.13 (m, 3H).

Synthesis of Intermediate 6-2

2,6-dihydroxy-1-naphthaldehyde (564 mg, 3 mmol) and K$_2$CO$_3$ (1.34 g, 9 mmol) were weighed into 6 ml of DMF and stirred at room temperature for 1 h. Methyl iodide (1.28 g, 9 mmol) was added and stirred at room temperature overnight. After completion of the reaction, sodium thiosulfate was added to quench the reaction, and extracted by ethyl acetate. Solvents were removed in vacuo, and the obtained residue was recrystallized in ethanol to give 430 mg of solids in a yield of 66.4%.

LC-MS: 217.10 (M+1)$^+$.

$^1$H-NMR (400 MHz, DMSO-d6): δ 10.74 (s, 1H), 9.02 (d, J=9.2 Hz, 1H), 8.23 (d, J=9.2 Hz, 1H), 7.58 (d, J=9.2 Hz, 1H), 7.39 (s, 1H), 7.31 (d, J=9.6 Hz, 1H), 4.03 (s, 3H), 3.86 (s, 3H).

Synthesis of Intermediate 6-3

2,6-dimethoxy-1-naphthaldehyde (11.3 g, 0.1597 mol) was weighed into 250 ml of dry methylene chloride. AlCl$_3$ (21.3 g, 0.1597 mol) was added in portions and stirred at 40° C. for 36 h. After completion of the reaction, the reaction solution was poured into brine and extracted with ethyl acetate. The organic phase was washed with saturated brine for two times, dried over anhydrous sodium sulfate, evaporated to dryness in vacuo to give solids. The solids were recrystallized in ethanol to obtain pale yellow solids. LC-MS: 203.10 (M+1)$^+$, 201.10 (M−1)$^−$.

$^1$HNMR (400 MHz, DMSO-d$_6$): δ 10.78 (s, 1H), 8.86 (d, J=9.2, 1H), 8.04 (d, J=8.8 Hz, 1H), 7.35 (d, J=2.8 Hz, 1H), 7.28 (dd, J$_1$=9.2 Hz, J$_2$=2.8 Hz, 1H), 7.22 (d, J=8.8 Hz, 1H), 3.86 (s, 3H)

Synthesis of Intermediate 6-4

7-methoxy-2-hydroxy-1-naphthaldehyde (101 mg, 0.5 mmol), compound 1-1 (506 mg, 2.5 mmol, 1.5 eq), DABCO (56 mg, 0.5 mmol) were weighed into a 50 ml of round bottom flask. Appropriate amount of DCM was added and stirred at 70° C. overnight. After completion of the reaction, the reaction mixture was purified by column chromatography (dichloromethane:petroleum ether=1:2) to give the product as red solids. LC-MS: 388.10 (M+1)$^+$.

$^1$HNMR (400 MHz, CDCl$_3$): δ 8.82 (s, 1H), 8.01 (d, J=9.2 Hz, 1H), 7.77 (d, J=8.8 Hz, 1H), 7.34 (dd, J=9.2 Hz, J=2.4 Hz, 1H), 7.12 (dd, J=2.8 Hz, 1H), 7.05-7.00 (m, 2H), 6.97 (s, 1H), 3.93 (s, 3H)

Synthesis of Intermediate 6-5

Compound 42 (500 mg, 1.292 mmol) was weighed into a 250 mL round bottom flask and 55 ml of THF/CH$_3$OH (10:1) mixture was added into the flask to dissolve the solid. Sodium borohydride (100 mg, 2.642 mmol) was added in portions. A drying tube was installed at the mouth of the bottle, and the reaction was performed for 20 mins at room temperature and under normal pressure. After the reaction was completed, water was added into the reaction solution for quenching the reaction, extracted with ethyl acetate, and dried over anhydrous sodium sulfate. The solution was evaporated to dryness in vacuo, and directly used in the next step.

Synthesis of (2S,3R)-8-methoxy-3-(2,4,5-trifluorophenyl)-2,3-dihydro-1H-benzo[f]-chroman-2-amine (compound-6)

The above obtained compound was dissolved in 100 ml of ethanol, Zn powder (835 mg, 12.85 mmol) was added, 6 ml of 6N HCl solution was added and the reaction was performed at 50° C. for 2 hours. The reaction solution was neutralized with saturated sodium bicarbonate solution, extracted with ethyl acetate, dried over anhydrous sodium sulfate, evaporated to dryness and separated by column chromatography (PE:EA=2:1) to give a white product 6-6 (175 mg, 37.8%). Compound 6 was obtained through resolution by a HPLC chiral column. LC-MS (M+1)+: 360.15.

¹H NMR (400 MHz, DMSO-d₆): δ 7.76 (d, J=9.2 Hz, 1H), 7.70-7.57 (m, 3H), 7.30 (d, J=2.4 Hz, 1H), 7.21 (dd, J₁=9.0 Hz, J₂=2.4 Hz, 1H), 7.04 (d, J=8.8 Hz, 1H), 4.89 (d, J=8.8 Hz, 1H), 3.86 (s, 3H), 3.44-3.38 (m, 1H), 3.34 (dd, J₁=16.2 Hz, J₂=5.6 Hz, 1H), 2.86 (dd, J₁=17.2 Hz, J₂=10.0 Hz, 1H), 1.76 (s, 2H).

7. (2S,3R)-8-bromo-3-(2,4,5-trifluorophenyl)-2,3-dihydro-1H-benzo[f]-chroman-2-amine (compound-7)

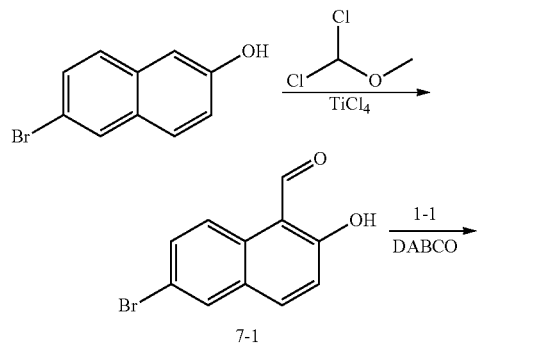

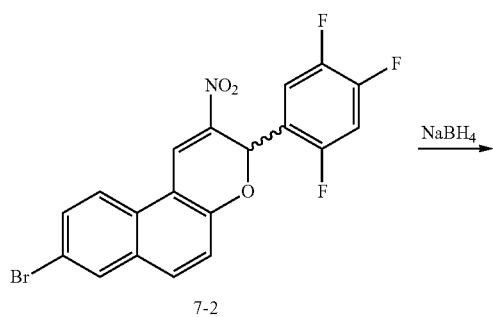

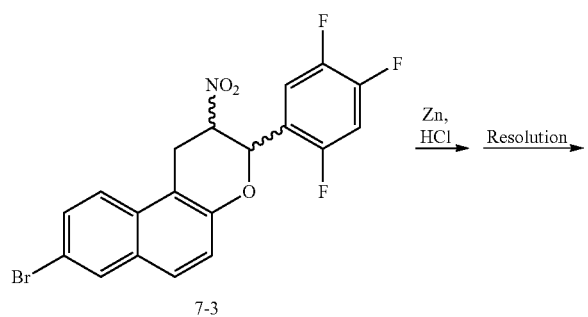

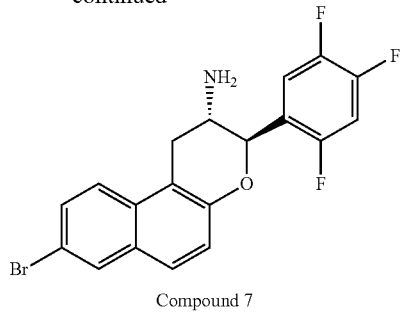

Compound 7

Synthesis of Intermediate 7-1

TiCl₄ (7.97 g, 42 mmol) and 1,1-dichloromethyl ether (2.53 g, 22 mmol) were weighed in 20 ml of dichloromethane and stirred at 0° C. for 15 min. 6-bromo-2-hydroxynaphthalene (4.46 g, 20 mmol) was weighed into 60 ml of dichloromethane and added dropwise to the above reaction solution and stirred at room temperature for 12 h. After completion of the reaction, 200 ml of 1N hydrochloric acid was added and extracted with dichloromethane. The organic phase was washed with water and dried to directly give 3.4 g of product in a yield of 67.7%. LC-MS: 250.95 (M−1)⁻.

¹H-NMR (400 MHz, DMSO-d6): δ 11.91 (s, 1H), 10.77 (s, 1H), 8.93 (d, J=8.8 Hz, 1H), 8.17 (d, J=2.0 Hz, 1H), 8.11 (d, J=9.2 Hz, 1H), 7.73 (dd, J=8.8 Hz, J=2.0 Hz, 1H), 7.31 (d, J=8.8 Hz, 1H).

Synthesis of Intermediate 7-2

Compound 6-bromo-2-hydroxy-1-naphthaldehyde (40 mg, 0.16 mmol), Compound 1-1 (162.4 mg, 0.8 mmol), DABCO (9 mg, 0.08 mmol) were weighed into a 10 ml round bottom flask and was heated to 60° C. under Argon atmosphere and stirred overnight. After completion of the reaction, 10 ml of methylene chloride was added and the obtained mixture was separated by column chromatography to give 28 mg of pale yellow solids in a yield of 40%. LC-MS: 437.95 (M+1)+, 436.05 (M−1)⁻.

¹H NMR (400 MHz, DMSO-d6): δ 9.00 (s, 1H), 8.37 (d, J=9.2 Hz, 1H), 8.23 (d, J=1.6 Hz, 1H), 8.03 (d, J=9.2 Hz, 1H), 7.80 (dd, J₁=9.2 Hz, J₂=1.6 Hz, 1H), 7.76-7.69 (m, 1H), 7.65-7.59 (m, 1H), 7.21 (d, J=8.8 Hz, 1H), 7.03 (s, 1H).

Synthesis of Intermediate 7-3

7-2 (217 mg, 0.5 mmol) was weighed into a 50 ml reaction flask and dissolved by adding THF:CH₃OH=(10:1, 11 ml). Sodium borohydride (76 mg, 2 mmol) was slowly added with magnetically stirring and stirred at room temperature for 20 min. After completion of the reaction, a small amount of water was added to quench the reaction, and the solvent was dried under reduced pressure. 10 ml of water was added and extracted with ethyl acetate (10 ml*3). The organic phases were combined and directly separated by column chromatography to give 60 mg of pale yellow solids in a yield of 27.5%.

¹HNMR (400 MHz, CDCl₃): δ 7.99 (s, 1H), 7.67-7.64 (m, 3H), 7.28-7.22 (m, 1H), 7.16 (d, 0.9.2 Hz, H), 7.06-7.00 (m, 1H), 5.78 (d, J=7.6 Hz, 1H), 5.31-5.26 (m, 1H), 3.90 (dd, J=8.4 Hz, J=16.8 Hz, 1H), 3.59 (dd, J=6.0 Hz, J=16.8 Hz, 1H).

Synthesis of (2S,3R)-8-bromo-3-(2,4,5-trifluorophenyl)-2,3-dihydro-1H-benzo[f]-chroman-2-amine (compound-7)

7-3 (44 mg, 0.1 mmol) and zinc powder (78 mg, 1.2 mmol) were weighed into 6 ml of ethanol, a few drops of DMF was added dropwise to dissolve them. 6 N hydrochloric acid solution (1.5 ml) was added at room temperature with stirred, and heated to 50° C. for reacting overnight. After completion of the reaction, the reaction mixture was neutralized with saturated sodium bicarbonate solution, extracted with ethyl acetate, and dried over anhydrous sodium sulfate. The solvent was evaporated in vacuo and the residue was separated by column chromatography (PE: EA=1:1) to give 17 mg of product in a yield of 41.5%. Compound 7 was obtained by chiral resolution. LC-MS: 408.05 (M+1)$^+$.

$^1$HNMR (400 MHz, CDCl$_3$): δ 7.94 (d, J=2.0 Hz, 1H), 7.67 (d, J=8.8 Hz, 1H), 7.59-7.56 (m, 2H), 7.38-7.32 (m, 1H), 7.12 (d, J=8.8 Hz, 1H), 7.05-6.98 (m, 1H), 5.03 (d, J=8.0 Hz, 1H), 3.44-3.36 (m, 2H), 2.96-2.88 (m, 1H), 1.45 (s, 2H).

8. trans-(2RS,3RS)-9-bromo-3-(2,4,5-trifluorophenyl)-2,3-dihydro-1H-benzo[f]-chroman-2-amine (compound-8)

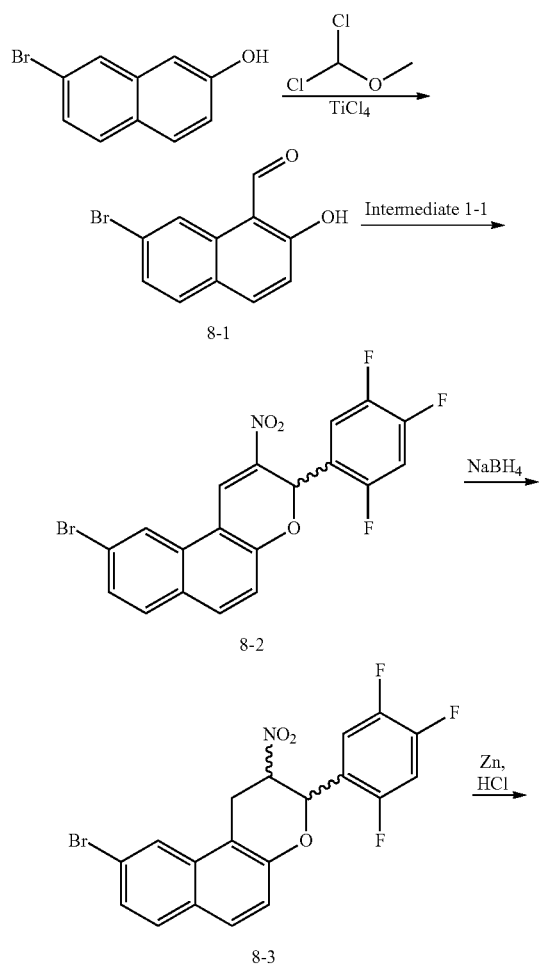

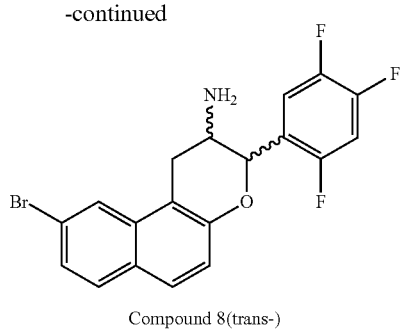

Compound 8(trans-)

Synthesis of Intermediate 8-1

TiCl$_4$ (797 mg, 4.2 mmol) and 1,1-dichloromethyl ether (253 mg, 2.2 mmol) were weighed into 2 ml of dichloromethane and stirred at 0° C. for 15 mins. 7-bromo-2-hydroxynaphthalene (446 mg, 2 mmol) was weighed into 6 ml of methylene chloride, added dropwise to the above reaction solution, and stirred at room temperature for 12 h. After completion of the reaction, 20 ml of 1 N hydrochloric acid solution was added, extracted with ethyl acetate and dried over anhydrous sodium sulfate to directly give the product 440 mg in a yield of 87.6%. LC-MS: 253.00 (M+1)$^+$, 251.00 (M−1)$^−$.

$^1$HNMR (400 MHz, DMSO-d6): δ 11.94 (s, 1H), 10.74 (s, 1H), 8.93 (d, J=2.0 Hz, 1H), 8.14 (d, J=8.8 Hz, 1H), 7.85 (d, J=8.4 Hz, 1H), 7.73 (dd, J=8.8 Hz, J=2.0 Hz, 1H), 7.29 (d, J=9.2 Hz, 1H).

Synthesis of Intermediate 8-2

Compound 7-bromo-2-hydroxy-1-naphthaldehyde (300 mg, 1.2 mmol), compound 1-1 (1.22 mg, 6 mmol), DABCO (134.4 mg, 1.2 mmol) were weighed into a 25 ml round bottom flask, heated to 70° C. under an argon atmosphere and stirred overnight. After completion of the reaction, 50 ml of methylene chloride was added and the mixture was directly separated by column chromatography to give 212 mg of pale yellow solids in a yield of 40.6%. LC-MS: 438.00 (M+1)$^+$.

$^1$HNMR (400 MHz, CDCl$_3$): δ 8.77 (s, 1H), 8.25 (m, 1H), 7.83 (d, J=8.8 Hz, 1H), 7.76 (d, J=8.4 Hz, 1H), 7.57 (dd, J=6.0 Hz, J=8.8 Hz, 1H), 7.07-6.99 (m, 4H).

Synthesis of Intermediate 8-3

8-2 (261 mg, 0.6 mmol) was weighed into a 50 ml reaction flask and dissolved by adding THF:CH$_3$OH (10:1, 22 ml). Sodium borohydride (45.6 mg, 1.2 mmol) was slowly added with magnetically stirring at room temperature for 20 min. After completion of the reaction, a small amount of water was added to quench the reaction, the solvent was evaporated to dryness under reduced pressure, and 10 ml of water was added and extracted with ethyl acetate (10 ml*3). The organic phases were combined and directly separated by column chromatography to give 65 mg of pale yellow solids in a yield of 24.8%.

$^1$HNMR (400 MHz, CDCl$_3$): δ 7.92 (s, 1H), 7.72-7.68 (m, 2H), 7.52 (dd, J=1.6, J=8.8, 1H), 7.15 (d, J=8.8, 1H), 7.06-6.95 (m, 2H), 5.80 (d, J=7.2 Hz, 1H), 5.31-5.26 (m, 1H), 3.87 (dd, J=16.4 Hz, J=8.0 Hz, 1H), 3.54 (dd, J=5.6 Hz, J=16.4 Hz, 1H).

Synthesis of Compound-8

8-2 (44 mg, 0.1 mmol) and zinc powder (78 mg, 1.2 mmol) were weighed into 6 ml of ethanol, and a few drops of DMF was added dropwise to dissolve them. 1.5 mL of 6 N hydrochloric acid solution was added at room temperature with stirring, and heated to 50° C. to react overnight. After completion of the reaction, the reaction mixture was neutralized with saturated sodium bicarbonate solution, extracted with ethyl acetate, and dried over anhydrous sodium sulfate. The solvent was evaporated to dryness and separated by column chromatography (PE:EA=1:1) to give 20 mg of product in a yield of 48.8%. LC-MS (M+1)$^+$: 408.00.

$^1$HNMR (400 MHz, CDCl$_3$): δ 8.00 (s, 1H), 7.84 (d, J=8.4 Hz, 1H), 7.76 (d, J=8.8 Hz, 1H), 7.71-7.59 (m, 2H), 7.52 (d, J=8.8 Hz, J=2.0 Hz, 1H), 7.13 (d, J=8.8 Hz, 1H), 4.96 (d, J=9.2 Hz, 1H), 3.49-3.43 (m, 1H), 3.36 (m, 1H), 2.86 (d, J=10.0 Hz, J=10.8 Hz, 1H), 1.45 (s, 2H).

9. trans-(2RS,3RS)-8-cyano-3-(2,4,5-trifluorophenyl)-2,3-dihydro-1H-benzo[f]-chroman-2-amine (compound-9)

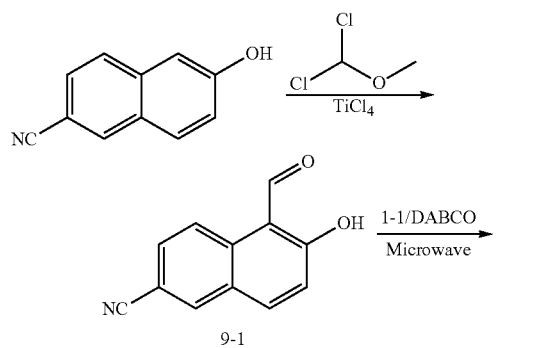

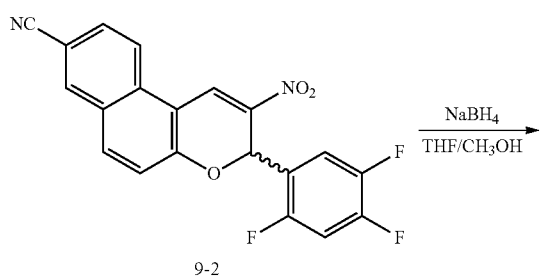

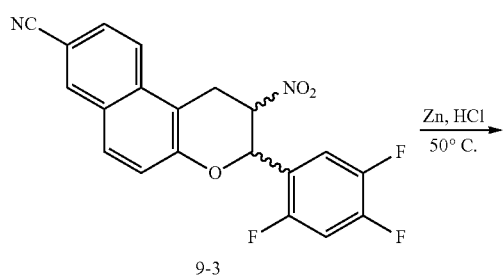

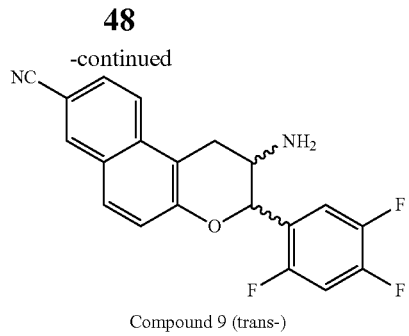

Compound 9 (trans-)

Synthesis of Intermediate 9-1

TiCl$_4$ (398.5 mg, 2.1 mmol) and 1,1-dichloromethyl ether (126.5 mg, 1.1 mmol) were weighed into 2 ml of dichloromethane and stirred at 0° C. for 15 mins. 6-cyano-2-naphthol (169 mg, 1 mmol) was weighed into 6 ml of methylene chloride, added dropwise to the above reaction solution, and stirred at room temperature for 12 h. After completion of the reaction, 20 ml of 1 N hydrochloric acid solution was added, and extracted with methylene chloride. The organic phase was washed with water and dried to directly give a product 350 mg in a yield of 75.4%. LC-MS: 196.05 (M-1)$^-$.

$^1$HNMR (400 MHz, DMSO-d6): δ 12.22 (s, 1H), 10.76 (s, 1H), 9.11 (d, J=9.2 Hz, 1H), 8.50 (d, J=2.0 Hz, 1H), 8.22 (d, J=8.8 Hz, 1H), 7.88 (dd, J=9.2 Hz, J=2.4 Hz, 1H), 7.39 (d, J=9.2 Hz, 1H)

Synthesis of Intermediate 9-2

Compound 6-cyano-2-hydroxy-1-naphthaldehyde (197 mg, 1 mmol), compound 1-1 (609 mg, 3 mmol), DABCO (112 mg, 1 mmol) were weighed, and heated by microwave to 11° C. and stirred for 25 mins. After completion of the reaction, 10 ml of methylene chloride was added and the mixture was directly separated by column chromatography to give 102 mg of pale yellow solids in a yield of 26.7%. LC-MS: 381.05 (M-1)$^-$.

$^1$HNMR (400 MHz, CDCl$_3$): δ 8.80 (s, 1H), 8.19 (m, 2H), 7.93 (d, J=8.8 Hz, 1H), 7.82 (dd, J=9.2 Hz, J=1.6 Hz, 1H), 7.19 (d, J=9.2 Hz, 1H), 7.09-7.00 (m, 3H).

Synthesis of Intermediate 9-3

9-2 (176 mg, 0.5 mmol) was weighed into a 50 ml reaction flask and dissolved by adding THF:CH$_3$OH (10:1, 22 ml). Sodium borohydride (76 mg, 2 mmol) was slowly added with magnetically stirring at room temperature for 20 min. After completion of the reaction, a small amount of water was added to quench the reaction, the solvent was evaporated to dryness under reduced pressure, and 10 ml of water was added and extracted with ethyl acetate (10 ml*3). The organic phases were combined and directly separated by column chromatography to give 57 mg of pale yellow solids in a yield of 32.2%.

$^1$HNMR (400 MHz, DMSO-d6): δ 8.57 (d, J=1.6 Hz, 1H), 8.09 (d, J=8.8 Hz, 1H), 7.98 (d, J=9.2 Hz, 1H), 7.87 (d, J=8.8 Hz, J=1.6 Hz, 1H), 7.80-7.70 (m, 2H), 7.36 (s, J=9.2 Hz, 1H), 5.96 (d, J=8.0 Hz, 1H), 5.85 (dd, J=6.8 Hz, J=14.8 Hz, 1H), 3.85 (d, J=7.2 Hz, 2H).

Synthesis of Compound-9

9-3 (38.4 mg, 0.1 mmol) and zinc powder (78 mg, 1.2 mmol) were weighed into 10 ml of ethanol, and stirred at room temperature. 1.5 mL of 6 N hydrochloric acid solution was added, and heated to 50° C. to react overnight. After completion of the reaction, the reaction mixture was neutralized with saturated sodium bicarbonate solution, extracted with ethyl acetate, and dried over anhydrous sodium sulfate. The solvent was evaporated to dryness and separated by column chromatography (PE:EA=1:1) to give 17 mg of product in a yield of 48%. LC-MS (M+1)⁺: 355.10.

¹HNMR (400 MHz, DMSO-d6): δ 8.50 (d, J=1.6 Hz, 1H), 8.00 (d, J=8.8 Hz, 1H), 7.88 (d, J=8.8 Hz, 1H), 7.81 (d, J=8.8 Hz, J=1.6 Hz, 1H), 7.72-7.59 (m, 2H), 7.25 (d, J=8.8 Hz, 1H), 5.00 (d, J=9.2 Hz, 1H), 3.45-3.36 (m, 2H), 2.90 (d, J=8.8 Hz, J=16 Hz, 1H).

10. trans-(2RS,3RS)-8-hydroxyformyl-3-(2,4,5-trifluorophenyl)-2,3-dihydro-1H-benzo[f]-chroman-2-amine (compound-10)

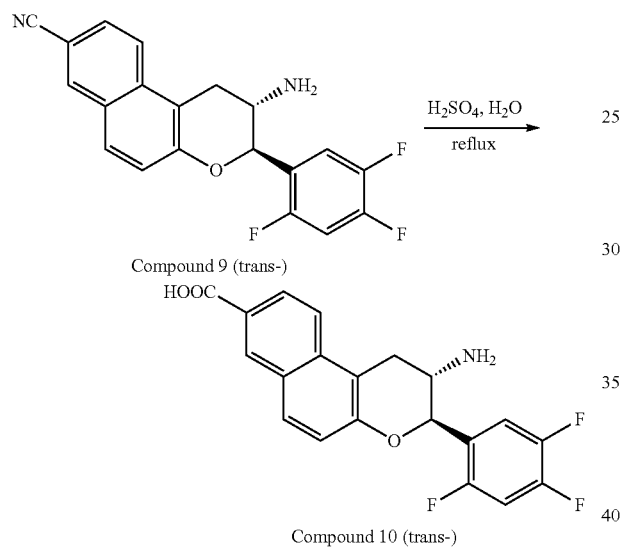

Compound 9 (35.4 mg, 0.1 mmol) was weighed in 45% sulfuric acid solution (1.8 mL) and stirred at reflux overnight. After completion of the reaction, the mixture was neutralized with saturated sodium bicarbonate solution, extracted with ethyl acetate and separated by column chromatography (DCM:CH₃OH=10:1) to give 8 mg of a white powder in a yield of 22%. LC-MS (M+1)⁺: 374.10

¹HNMR (400 MHz, DMSO-d6): δ 8.49 (d, J=1.6 Hz, 1H), 8.13 (dd, J=8.8 Hz, J=1.6 Hz, 1H), 7.87 (d, J=8.8 Hz, 1H), 7.79 (d, J=9.2 Hz, 1H), 7.49-7.43 (m, 1H), 7.32-7.25 (m, 1H), 7.15 (d, J=8.8 Hz, 1H), 5.17 (d, J=8.4 Hz, 1H), 4.6 (s, 1H), 3.64 (m, 1H), 3.44 (dd, J=8.8 Hz, J=16.4 Hz, J=5.6 Hz, 1H, 3.05 (dd, J=16.4 Hz, J=9.2 Hz, 1H).

11. trans-(2RS,3RS)-9-cyano-3-(2,4,5-trifluorophenyl)-2,3-dihydro-1H-benzo[f]-chroman-2-amine (compound-11)

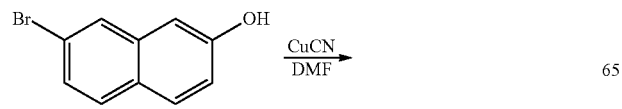

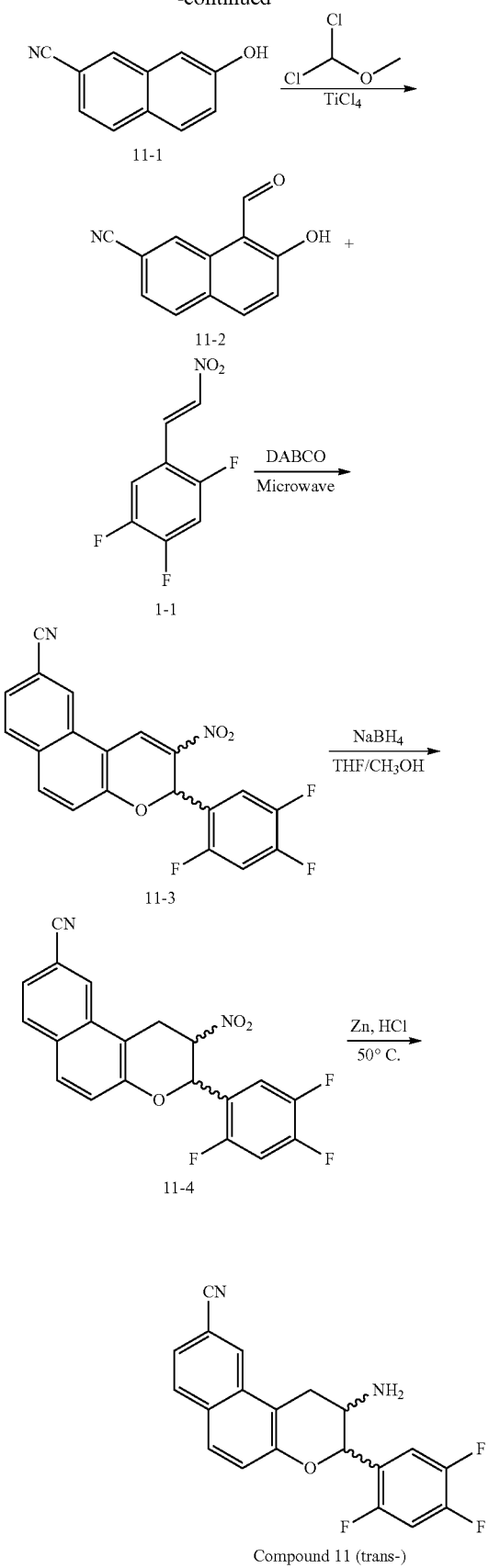

Synthesis of Intermediate 11-1

7-bromo-2-naphthol (2.22 g, 10 mmol), CuCN (1.08 g, 12 mmol) were weighed and dissolved into 3 ml of DMF. Under an atmosphere of argon, the mixture was heated to 160° C. for 3 hours. The reaction was monitored until the reaction was completed, and cooled to room temperature. 20 ml of water was added and extracted with ethyl acetate. Recrystallization was performed in an ethanol-water system to give 1.4 g of brown powder in a yield of 83%.

$^1$HNMR (400 MHz, DMSO-d6): δ 10.18 (s, 1H), 8.35 (s, 1H), 7.97 (d, J=8.0 Hz, 1H), 7.91 (d, J=8.4 Hz, 1H), 7.52 (dd, J=8.4 Hz, J=1.6 Hz, 1H), 7.29-7.27 (m, 2H)

Synthesis of Intermediate 11-2

TiCl$_4$ (3.99 mg, 21 mmol) and 1,1-dichloromethyl ether (1.265 mg, 11 mmol) were weighed into 20 ml of dichloromethane and stirred at 0° C. for 15 mins. 7-cyano-2-naphthol (1.69 mg, 10 mmol) was weighed into 40 ml of methylene chloride, added dropwise to the above reaction solution, and stirred at room temperature for 12 h. After completion of the reaction, 20 ml of 1 N hydrochloric acid solution was added, and extracted with methylene chloride. The organic phase was washed with water and dried to directly give a product 500 mg in a yield of 25.3%. LC-MS: 196.10 (M−1)$^-$.

$^1$HNMR (400 MHz, DMSO-d6): δ 12.11 (s, 1H), 10.77 (s, 1H), 8.25 (d, J=9.2 Hz, 1H), 8.22 (d, J=8.8 Hz, 1H), 8.10 (d, J=8.4 Hz, 1H), 7.74 (dd, J=8.4 Hz, J=1.6 Hz, 1H), 7.45 (d, J=9.2 Hz, 1H)

Synthesis of Intermediate 11-3

Compound 7-cyano-2-hydroxy-1-naphthaldehyde (197 mg, 1 mmol), 1-1 (609 mg, 3 mmol), DABCO (112 mg, 1 mmol) were weighed, and heated by microwave to 11° C. and stirred for 25 mins. After completion of the reaction, 10 ml of methylene chloride was added and the mixture was directly separated by column chromatography to give 112 mg of pale yellow solids in a yield of 29.3%. LC-MS: 383.15 (M+1)$^+$, 381.00 (M−1)$^-$.

$^1$H NMR (400 MHz, DMSO-d6): δ 9.21 (s, 1H), 9.11 (s, 1H), 8.16 (d, J=9.2 Hz, 1H), 8.12 (d, J=8.8 Hz, 1H), 7.81 (d, J=8.4 Hz, 1H), 7.76-7.71 (m, 1H), 7.69-7.61 (m, 1H), 7.35 (d, J=8.8 Hz, 1H), 6.99 (s, 1H), 7.06 (s, 3H).

Synthesis of Intermediate 11-4

11-3 (176 mg, 0.5 mmol) was weighed into a 50 ml reaction flask and dissolved by adding THF:CH$_3$OH (10:1, 22 ml). Sodium borohydride (76 mg, 2 mmol) was slowly added with magnetically stirring at room temperature for 20 min. After completion of the reaction, a small amount of water was added to quench the reaction, the solvent was evaporated to dryness under reduced pressure, and 10 ml of water was added and extracted with ethyl acetate (10 ml*3). The organic phases were combined and directly separated by column chromatography to give 57 mg of pale yellow solids in a yield of 32.2%.

Synthesis of Compound-11

11-4 (38.4 mg, 0.1 mmol) and zinc powder (78 mg, 1.2 mmol) were weighed into 10 ml of ethanol, and stirred at room temperature. 1.5 mL of 6 N hydrochloric acid solution was added, and heated to 50° C. to react overnight. After completion of the reaction, the reaction mixture was neutralized with saturated sodium bicarbonate solution, extracted with ethyl acetate, and dried over anhydrous sodium sulfate. The solvent was evaporated to dryness and separated by column chromatography (PE:EA=1:1) to give 17 mg of product in a yield of 48%. LC-MS (M+1)$^+$: 355.10.

12. (2S,3R)-8,9-dimethoxy-3-(2,4,5-trifluorophenyl)-2,3-dihydro-1H-benzo[f]-chroman-2-amine (compound-12)

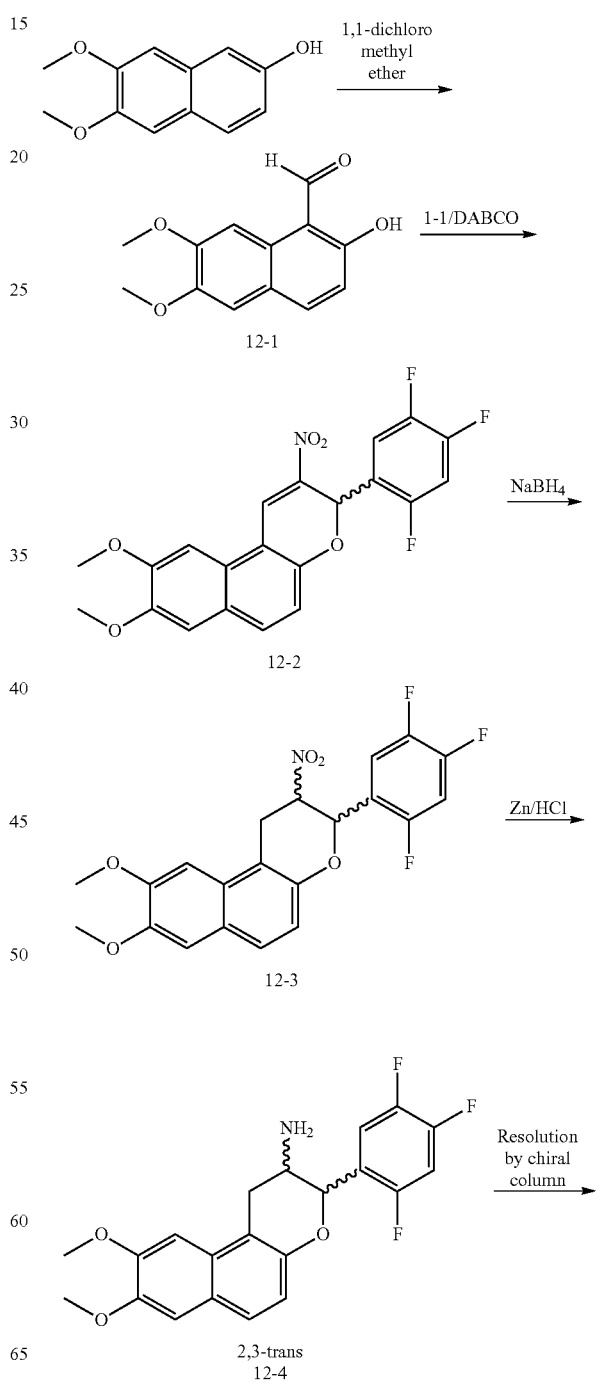

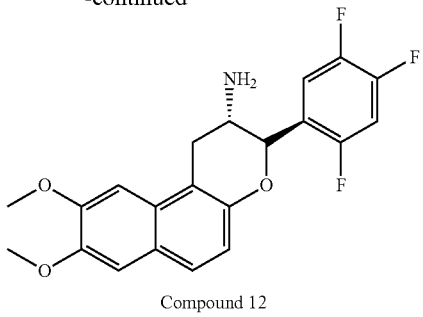

Compound 12

Synthesis of Intermediate 12-1

1,1-dichloromethyl ether (0.62 g, 0.0054 mol) was weighed in a 250 mL round bottom flask and dissolved in an appropriate amount of dichloromethane. Titanium tetrachloride (2.0 g, 0.0102 mol) was added at 0° C., and stirred at 0° C. for 15 mins. 6,7-dimethoxy-2-naphthol (1 g, 0.0049 mol) was weighed and dissolved in an appropriate amount of methylene chloride and added dropwise to the above solution. The solution changed from pale yellow to red in color. Upon addition, the solution was allowed to react overnight at room temperature. After completion of the reaction, the solution was poured into 50 mL of 1 N hydrochloric acid solution, stirred at room temperature for 1 h, and extracted with ethyl acetate. The organic phase was washed with saturated brine, and dried over anhydrous sodium sulfate. The solution was evaporated to dryness and separated by column chromatography, thereby obtaining the product. LC-MS: 233.10 (M+1)$^+$, 231.10 (M−1)$^-$.

$^1$HNMR (400 MHz, CDCl$_3$): δ 12.85 (s, 1H), 10.75 (s, 1H), 7.82 (d, J=9.2 Hz, 1H), 7.64 (s, 1H), 7.10 (s, 1H), 6.99 (d, J=8.8, 1H), 4.05 (s, 3H), 3.99 (s, 3H)

Synthesis of Intermediate 12-2

6,7-dimethoxy-2-cyano-1-naphthaldehyde (200 mg, 0.8618 mmol), Compound 1-1 (875 mg, 4.3103 mmol), DABCO (97 mg, 0.8661 mmol) were weighed in a pressure tube, homogeneously mixed and tightly compressed. Under microwave conditions, the reaction was performed at 120° C. for 30 mins. After completion of the reaction, the solids were dissolved in methylene chloride and separated by column chromatography (DCM:PE=1:2) to give the product. LC-MS: 418.10 (M+1)$^+$.

$^1$H NMR (400 MHz, DMSO-d6): δ 9.12 (s, 1H), 7.85 (d, J=8.8 Hz, 1H), 7.75-7.68 (m, 1H), 7.72 (s, 1H), 7.53-7.46 (m, 1H), 7.34 (s, 1H), 6.95 (s, 1H), 6.94 (d, J=8.4 Hz, 1H), 4.04 (s, 3H), 3.87 (s, 3H).

Synthesis of Intermediate 12-3

Compound 47 (50 mg, 0.1200 mmol) was weighed into a 50 mL round bottom flask and 5 ml of THF/CH$_3$OH (10:1) mixture was added into the flask to dissolve the solid. Sodium borohydride (10 mg, 0.2642 mmol) was added in portions. A drying tube was installed at the mouth of the bottle, and the reaction was performed for 20 mins at room temperature and under normal pressure. After the reaction was completed, water was added into the reaction solution for quenching the reaction, extracted with ethyl acetate, and dried over anhydrous sodium sulfate. The solution was evaporated to dryness in vacuo, and directly used in the next step.

Synthesis of Intermediate 12-4

The above obtained compound was dissolved in 50 ml of ethanol. Zn powder (8.35 mg, 1.285 mmol) and 2 N of 6 N HCl solution was added and reacted at 50° C. for 2 h. The reaction solution was neutralized with saturated sodium bicarbonate solution, extracted with ethyl acetate, dried over anhydrous sodium sulfate. The solution was evaporated to dryness and separated by column chromatography (PE:EA=2:1) to give a white product. LC-MS (M+1)$^+$: 390.15.

$^1$H NMR (500 MHz, DMSO-d$_6$): δ 7.70-7.57 (m, 2H), 7.55 (d, J=8.8 Hz, 1H), 7.28 (s, 1H), 7.10 (s, 1H), 6.90 (d, J=8.8 Hz, 1H), 4.87 (d, J=9.2 Hz, 1H), 3.92 (s, 3H), 3.86 (s, 3H), 3.44-3.38 (m, 1H), 3.32 (dd, J$_1$=15.0 Hz, J$_2$=5.6 Hz, 1H), 2.82 (dd, J$_1$=16.4 Hz, J$_2$=10.0 Hz, 1H), 1.62 (s, 2H).

Compound 12: Compound 12 obtained from compound 12-4 of trans-configuration through resolution by chiral column

13. trans-(2RS,3RS)-9-(4-(methanesulfonyl)phenyl)-3-(2,4,5-trifluorophenyl)-2,3-dihydro-1H-benzo[f]-chroman-2-amine (compound-13)

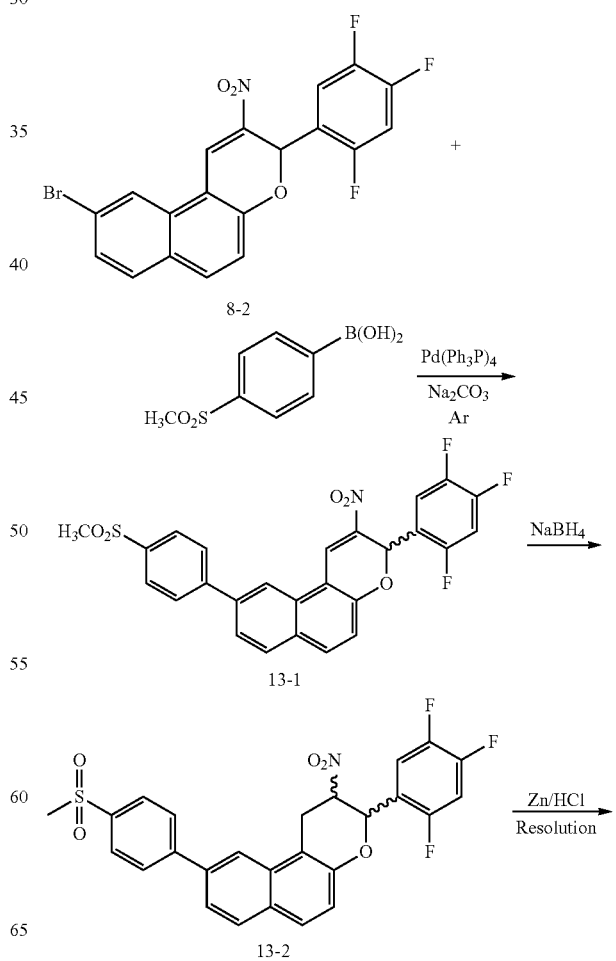

-continued

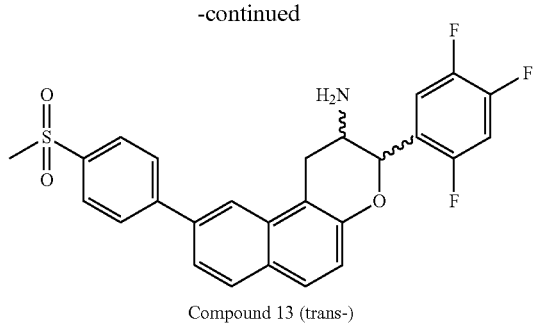

Compound 13 (trans-)

Synthesis of Intermediate 13-1

8-2 (300 mg, 0.69 mmol), 4-methanesulfonylphenylboronic acid (276 mg, 1.38 mmol) were dissolved in toluene (2.8 mL). To the solution was added 5% tetraphenylphenylphosphine palladium (39.9 mg). Argon was bubbled for 15 min. The reaction was performed at 80° C. for 1 h under argon atmosphere. NaHCO$_3$ solution (2 M, 1.4 mL) and ethanol (1.4 mL) were added with a syringe and the reaction was performed for another 24 hr. After completion of the reaction, an appropriate amount of water was added to the solution, and extracted with ethyl acetate. The organic phase was washed with water for several times and with saturated aqueous NaCl solution, and dried over anhydrous Na$_2$CO$_3$. 274 mg of product was obtained through column chromatography (Petroleum ether:ethyl acetate=2:1) in a yield of 77.7%. LC-MS: 512.10 (M+1)$^+$.

$^1$HNMR (400 MHz, DMSO-d$_6$): δ 9.30 (s, 1H), 8.75 (s, 1H), 8.25 (d, J=8.8 Hz, 2H), 8.09 (d, J=8.8 Hz, 2H), 8.06 (d, J=8.4 Hz, 2H), 7.90 (dd, J$_1$32 8.0 Hz, J$_2$=1.2 Hz, 1H), 7.73-7.67 (m, 1H), 7.71-7.54 (m, 1H), 7.19 (d, J=9.2 Hz, 1H), 7.03 (s, 1H), 3.30 (s, 3H)

Synthesis of Intermediate 13-2

Compound 7 (250 mg, 0.4892 mmol) was dissolved in 3 mL of anhydrous methanol and 30 mL of anhydrous tetrahydrofuran was added. Sodium borohydride (74 mg, 1.955 mmol) was added in portions and stirred at room temperature for about 20 mins. When the reaction was completed, the solvent was evaporated to dryness, and the residue was directly used in the next reaction.

Synthesis of Compound 13

Compound 8 (250 mg, 0.5175 mmol) was dissolved in 5 mL of ethanol, and to the solution was added 12 mL of 6 N hydrochloric acid and zinc powder (406.1 mg, 6.210 mmol). The reaction was performed by heating at 55° C. overnight until the reaction solution was a clear solution. After the reaction was completed, saturated NaHCO$_3$ was added to the solution, and the solution was neutralized, extracted with ethyl acetate, washed with saturated brine and dried over anhydrous Na$_2$SO$_4$. The residue was purified by column chromatography on ethyl acetate:petroleum ether=1:2 to obtain the product. LC-MS (M+1)$^+$: 484.20.

$^1$HNMR (400 MHz, DMSO-d$_6$): δ 8.15 (s, 1H), 8.11 (d, J=8.8 Hz, 2H), 8.05 (d, J=8.4 Hz, 2H), 8.01 (d, J=8.4 Hz, 1H), 7.08-7.77 (m, 2H), 7.72-7.65 (m, 1H), 7.63-7.58 (m, 1H), 7.15 (d, J=8.8 Hz, 1H), 4.98 (d, J=8.8 Hz, 1H), 3.58-3.46 (m, 1H), 3.26 (s, 3H), 3.01-2.95 (m, 1H)

14. (2S,3R)-9-(3-(methanesulfonyl)phenyl)-3-(2,4,5-trifluorophenyl)-2,3-dihydro-1H-benzo[f]-chroman-2-amine (compound-14)

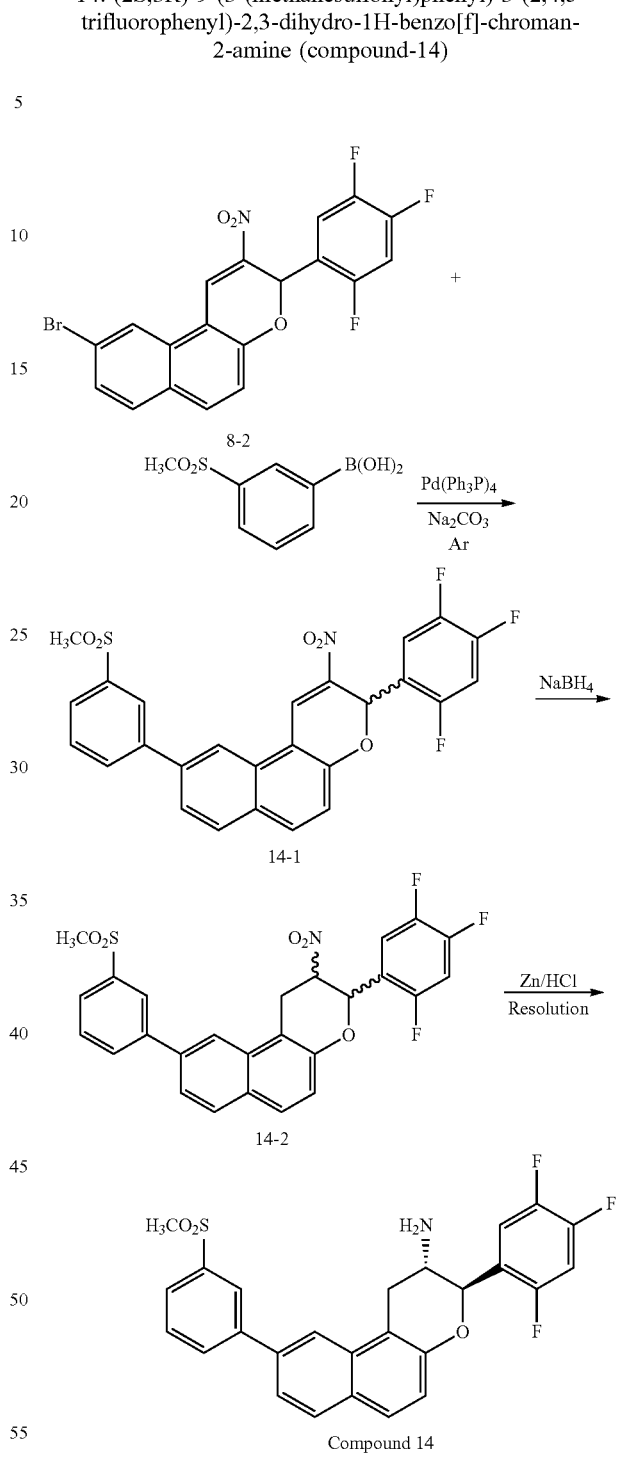

Synthesis of Intermediate 14-1

8-2 (500 mg, 1.15 mmol), 3-methanesulfonylphenylboronic acid (459.8 mg, 2.30 mmol) were dissolved in toluene (4.6 mL). To the solution was added 5% tetraphenylphenylphosphine palladium (66.4 mg). Argon was bubbled for 15 min. The reaction was performed at 80° C. for 1 h under argon atmosphere. NaHCO$_3$ solution (2 M, 2.3 mL) and ethanol (2.3 mL) were added with a syringe and the reaction was performed for another 24 hr. After completion of the reaction, an appropriate amount of water was added to the solution, and extracted with ethyl acetate. The organic phase was washed with water for several times and with saturated aqueous NaCl solution, and dried over anhydrous $Na_2CO_3$. The product was obtained through column chromatography (Petroleum ether:ethyl acetate=2:1). LC-MS: 512.10 $(M+1)^+$.

$^1$HNMR (400 MHz, DMSO-$d_6$): δ 9.30 (s, 1H), 8.73 (s, 1H), 8.46 (s, 1H), 8.34 (d, J=8.80 Hz, 1H), 8.09 (d, J=9.2 Hz, 1H), 8.07 (d, J=8.8 Hz, 1H), 8.01 (d, J=8.0 Hz, 1H), 7.92 (dd, $J_1$=8.0 Hz, $J_2$=1.6 Hz, 1H), 7.84 (t, J=8.0 Hz, 1H), 7.77-7.67 (m, 1H), 7.63-7.57 (m, 1H), 7.19 (d, J=8.8 Hz, 1H), 7.03 (s, 1H), 3.36 (s, 3H)

Synthesis of Intermediate 14-2

14-1 (250 mg, 0.4892 mmol) was dissolved in 3 mL of anhydrous methanol and 30 mL of anhydrous tetrahydrofuran was added. Sodium borohydride (74 mg, 1.955 mmol) was added in portions and stirred at room temperature for about 20 mins. When the reaction was completed, water was added to quench the reaction, the solvent was evaporated to dryness, and the residue was extracted by ethyl acetate. The organic phase was dried over $Na_2CO_3$, evaporated to dryness, and directly used in the next reaction.

Synthesis of compound 14

14-2 (250 mg, 0.5175 mmol) was dissolved in 5 mL of ethanol, and to the solution was added 12 mL of 6 N hydrochloric acid and zinc powder (406.1 mg, 6.210 mmol). The reaction was performed by heating at 55° C. overnight until the reaction solution was a clear solution. After the reaction was completed, saturated $NaHCO_3$ was added to the solution, and the solution was neutralized, extracted with ethyl acetate, washed with saturated brine and dried over anhydrous $Na_2SO_4$. The residue was purified by column chromatography on ethyl acetate:petroleum ether=1:2 to obtain a white product. LC-MS: 484.10 $(M+1)^+$.

$^1$HNMR (400 MHz, DMSO-$d_6$): δ 8.32 (s, 1H), 8.21 (d, J=7.6 Hz, 1H), 8.14 (s, 1H), 8.02 (d, J=8.4 Hz, 1H), 7.98 (d, J=7.6 Hz, 1H), 7.83-7.78 (m, 3H), 7.73-7.69 (m, 1H), 7.67-7.61 (m, 1H), 7.14 (d, J=8.8 Hz, 1H), 4.97 (d, J=9.2 Hz, 1H), 3.58-3.52 (m, 1H), 3.50-3.44 (m, 1H), 3.35 (s, 3H), 2.98 (dd, $J_1$=16.2 Hz, $J_2$=10.0 Hz, 1H)

Compound 14 was obtained from the product of trans-configuration through resolution by chiral column.

15. trans-(2RS,3RS)-3-(2,4,5-trifluorophenyl)-2,3-dihydro-1H-benzo[f]-chroman-2-amine (compound-15)

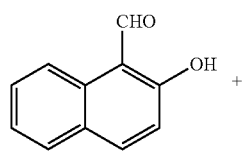

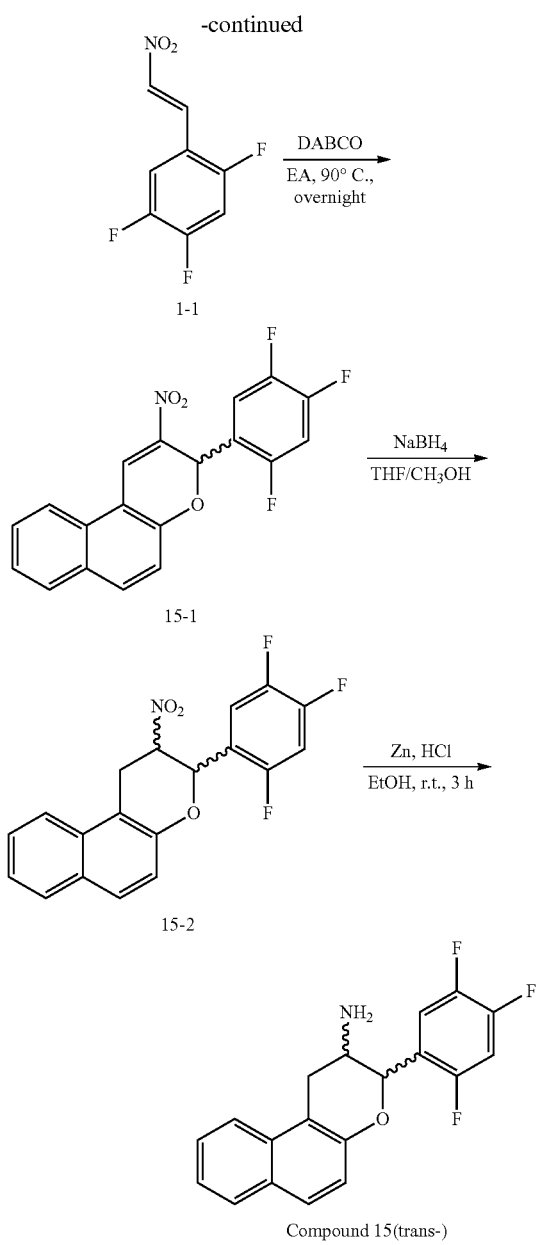

Synthesis of Intermediate 15-1

Compound 2-hydroxy-1-naphthaldehyde (6 g, 34.87 mmol), compound 1-1 (6.37 g, 31.32 mmol), DABCO (3.9 g, 34.87 mmol) were weighed into a 250 ml of round bottom flask. 100 ml of ethyl acetate was added and heated to 70° C. with stirring overnight under an argon atmosphere. After completion of the reaction, ethyl acetate was evaporated to dryness, and a suitable amount of dichloromethane was added to dissolve the residue. 1.5 g of solids in red were obtained by column chromatography in a yield of 13%. LC-MS: 358.10 $(M+1)^+$.

$^1$H NMR (400 MHz, DMSO-d6): δ 9.02 (s, 1H), 8.40 (d, J=8.4 Hz, 1H), 8.05 (d, J=9.2 Hz, 1H), 7.94 (d, J=8.0 Hz, 1H), 7.75-7.64 (m, 2H), 7.64-7.57 (m, 1H), 7.53 (t, J=8.0 Hz, 1H), 7.16 (d, J=8.8 Hz, 1H), 7.03 (s, 1H).

Synthesis of Intermediate 15-2

15-1 (1.2 g, 3.4 mmol) was weighed in a 100 mL reaction flask and dissolved by adding THF/CH$_3$OH (10:1, 55 ml). Sodium borohydride (0.38 g, 10.1 mmol) was slowly added with magnetically stirring at room temperature for 20 min. After completion of the reaction, a small amount of water was added to quench the reaction, the solvent was evaporated to dryness under reduced pressure, and 10 ml of water was added and extracted with ethyl acetate (10 ml*3). The organic phases were combined and dried over anhydrous sodium sulphate. The solvent was evaporated to dryness and the residue was directly used in the next step.

Synthesis of Compound 15

The above obtained crude product 15-2 was dissolved in 10 mL of ethanol, and to the solution was added 6 mL of 6 N hydrochloric acid and zinc powder (1.10 g, 1.70 mmol). The reaction was performed at room temperature and under normal pressure overnight until the reaction solution was a clear solution. After the reaction was completed, saturated NaHCO$_3$ was added to the solution, and the solution was neutralized, extracted with ethyl acetate, washed with saturated brine and dried over anhydrous Na$_2$SO$_4$. The residue was purified by column chromatography on ethyl acetate: petroleum ether=1:2 to obtain 920 mg of a white product in a two-step yield of 84%. LC-MS: 330.10 (M+1)$^+$.

$^1$H NMR (400 MHz, DMSO-d$_6$): 7.87 (d, J=3.6 Hz, 1H), 7.85 (d, J=4.0 Hz, 1H), 7.72 (d, J=8.8 Hz, 1H), 7.70-7.59 (m, 2H), 7.55 (t, J=7.6 Hz, 1H), 7.40 (t, J=7.6 Hz, 1H), 7.09 (d, J=8.8 Hz, 1H), 4.93 (d, J=9.2 Hz, 1H), 3.45-3.34 (m, 2H), 2.88 (dd, J$_1$=15.8 Hz, J$_2$=9.2 Hz, 1H), 1.69 (s, 2H).

16. N-((2S,3R)-2-amino-3-(2,4,5-trifluorophenyl)-2,3-dihydro-1H-benzo[f]-chroman-8)-methanesulfonamide (compound-16)

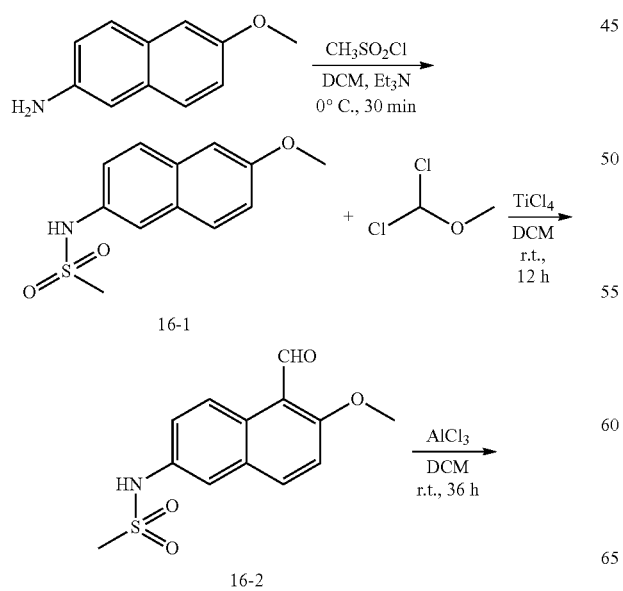

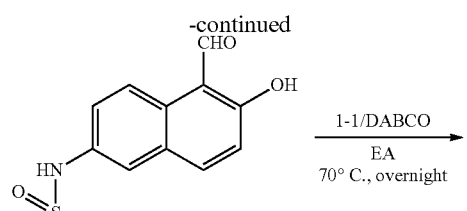

Synthesis of Intermediate 16-1

Compound 6-methoxy-2-naphthylamine (7 g, 0.04044 mol), triethylamine (6 g, 0.06067 mol) were weighed into a 100 mL reaction flask. 15 mL of methylene chloride was added to the reaction flask and reacted at 0° C. for 15 mins. Methanesulfonyl chloride (7 g, 0.06067 mol) was added dropwise and reacted at 0° C. for 30 mins. The reaction was monitored by TLC, and after completion of the reaction, an appropriate amount of aqueous sodium hydroxide was added, extracted by ethyl acetate, washed by saturated brine, and dried over anhydrous sodium sulfate. The solution was evaporated to dryness, and 5.6 g of solids in purple were obtained by column chromatography (PE:EA=2:1) in a yield of 55.2%. LC-MS: 252.10 (M+1)$^+$, 250.10 (M−1)$^+$.

$^1$H NMR (400 MHz, DMSO-d$_6$): δ 9.78 (s, 1H), 7.79 (d, J=12.0 Hz, 1H), 7.77 (d, J=12.0 Hz, 1H), 7.63 (d, J=1.6 Hz, 1H), 7.35 (dd, J$_1$=8.8 Hz, J$_2$=2.0 Hz, 1H), 7.29 (d, J=2.4 Hz, 1H), 7.15 (dd, J$_1$=8.8 Hz, J$_2$=2.4 Hz, 1H), 3.86 (s, 3H), 3.00 (s, 3H).

Synthesis of Intermediate 16-2

1,1-dichloromethyl ether (1.374 g, 0.0118 mol) was weighed into a 250 mL eggplant flask, and dissolved by adding 30 mL of dichloromethane. TiCl4 (2.2 mL, 0.0199 mol) was added into the solution and stirred at 0° C. for 15 mins. Compound 16-1 (2 g, 0.0080 mol) was weighed into an appropriate amount of methylene chloride and added dropwise to the above reaction solution. The mixture was stirred at room temperature for 36 h. After completion of the reaction, an appropriate amount of 1 N hydrochloric acid solution was added, extracted by ethyl acetate, dried over anhydrous sodium sulfate and separated by column chromatography (PE:EA=2:1) to give 1.515 g as white solids in a yield of 68.2%. LC-MS: 280.10 (M+1)$^+$, 278.05 (M−1)$^+$ $^1$H NMR (400 MHz, DMSO-d$_6$): δ 10.74 (s, 1H), 9.98 (s, 1H), 9.06 (d, J=9.2, 1H), 8.25 (d, J=9.2 Hz, 1H), 7.72 (d, J=2.0 Hz, 1H), 7.59 (d, J=9.2 Hz, 1H), 7.50 (dd, J$_1$=9.2 Hz, J$_2$=2.0 Hz, 1H), 4.05 (s, 3H), 3.06 (s, 3H).

Synthesis of Intermediate 16-3

Compound 16-2 (1.5 g, 0.0054 mol) was weighed into a 250 mL reaction flask and an appropriate amount of dry methylene chloride was added to the reaction flask until the substrate was completely dissolved. AlCl$_3$ (4.869 g, 0.03652 mmol) was added in portions. A drying tube was installed at the mouth of the flask, and the reaction was performed for 36 hrs at room temperature and under normal pressure. After the reaction was completed, a suitable amount of water was added into the reaction solution, stirred for a certain time, extracted with ethyl acetate, washed with saturated brine, and dried over anhydrous sodium sulfate. The solution was evaporated to dryness in vacuo, and 1.021 g of solids in orange were obtained by column chromatography (PE:EA=1:1) in a yield of 71.6%. LC-MS: 266.10 (M+1)$^+$, 264.00 (M−1)$^−$.

$^1$H NMR (400 MHz, DMSO-d$_6$): δ 11.83 (s, 1H), 10.78 (s, 1H), 9.91 (s, 1H), 8.93 (d, J=9.2 Hz, 1H), 8.09 (d, J=9.2 Hz, 1H), 7.68 (d, J=2.0 Hz, 1H), 7.48 (dd, J$_1$=9.2 Hz, J$_2$=2.4 Hz, 1H), 7.24 (d, J=8.8 Hz, 1H), 3.04 (s, 1H).

Synthesis of Intermediate 16-4

Compound 2-hydroxy-6-methanesulfonamido-1-naphthaldehyde (900 mg, 3.3957 mmol), compound 1-1 (1.032 g, 5.0936 mmol), DABCO (380 mg, 3.3957 mmol) were weighed in a 50 ml round bottom flask. Appropriate amount of EA was added and stirred at 70° C. overnight. After completion of the reaction, 850 mg of solids in dark red was obtained by column chromatography (dichloromethane:petroleum ether=2:1) in a yield of 52.7%. LC-MS: 449.00 (M−1)$^−$.

$^1$H NMR (400 MHz, DMSO-d6): δ 10.03 (s, 1H), 8.99 (s, 1H), 8.39 (d, J=9.2 Hz, 1H), 7.99 (d, J=9.2 Hz, 1H), 7.76-7.68 (m, 2H), 7.63-7.54 (m, 2H), 7.14 (d, J=9.2 Hz, 1H), 7.00 (s, 1H), 3.07 (s, 1H).

Synthesis of Intermediate 16-5

16-4 (800 mg, 1.777 mmol) was weighed in a 250 mL round bottom flask and THF/CH$_3$OH (10:1, 55 ml) was added to dissolve the solids. Sodium borohydride (673 mg, 17.77 mmol) was added into the solution in portions. A drying tube was installed at the mouth of the bottle, and the reaction was performed for 20 mins at room temperature and under normal pressure. The color of reaction solution changed from dark red to pale yellow. After the reaction was completed, water was added into the reaction solution for quenching the reaction, extracted with ethyl acetate, and dried over anhydrous sodium sulfate. The solution was evaporated to dryness in vacuo, and directly used in the next step.

Synthesis of Compound 16

The above obtained compound was dissolved in 40 mL of ethanol, and to the solution was added zinc powder (1150 mg, 17.692 mmol) and 10 mL of 6 N HCl. The reaction was performed at room temperature and under normal pressure for 2-3 hrs. Afterwards, the reaction solution was neutralized with saturated aqueous NaHCO$_3$, extracted with ethyl acetate and dried over anhydrous Na$_2$SO$_4$. The solution was evaporated to dryness and separated by column chromatography (PE:EA=1:2) to obtain 170 mg of a white product in a two-step yield of 22.7%. LC-MS: 423.10 (M+1)$^+$.

$^1$H NMR (500 MHz, DMSO-d$_6$): δ 7.84 (d, J=9.0 Hz, 1H), 7.69-7.62 (m, 3H), 7.62-7.58 (m, 1H), 7.44 (dd, J$_1$=9.0 Hz, J$_2$=2.0 Hz, 1H), 7.08 (d, J=9.0 Hz, 1H), 4.92 (d, J=9.0 Hz, 1H), 3.44-3.40 (m, 1H), 3.34 (dd, J$_1$=16.3 Hz, J$_2$=6.0 Hz, 1H), 3.01 (s, 3H), 2.86 (dd, J$_1$=16.3 Hz, J$_2$=10.5 Hz, 1H).

Compound 16 was obtained from the product of trans-configuration through resolution by chiral column. 17.

(2S,3R)-8-methanesulfonyl-3-(2,4,5-trifluorophenyl)-2,3-dihydro-1H-benzo[f]-chroman-2-amine (compound-17)

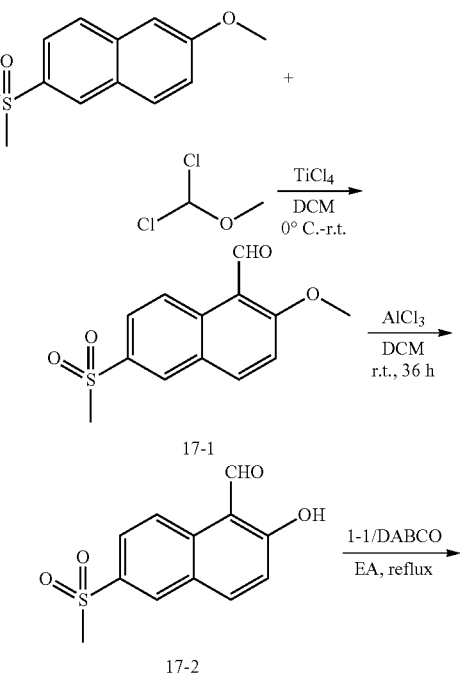

-continued

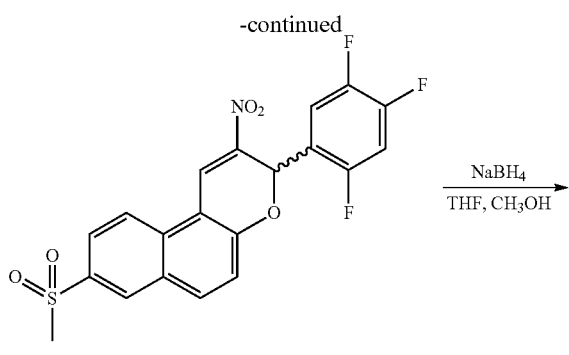

Synthesis of Intermediate 17-1

1,1-dichloromethyl ether (4.8 g, 0.04224 mol) was weighed into a 500 mL eggplant flask, and dissolved by adding 30 mL of dichloromethane. TiCl4 (14 g, 0.07040 mol) was added into the solution and stirred at 0° C. for 15 mins. 6-methoxy-2-methanesulfonylnaphthalene (4 g, 0.01693 mol) was weighed into an appropriate amount of methylene chloride and added dropwise to the above reaction solution. The mixture was stirred at room temperature for 36 h. The reaction was monitored by TLC, and after completion of the reaction, an appropriate amount of 1 N hydrochloric acid solution was added to adjust pH<7, extracted by dichloromethane, washed by saturated brine, dried over anhydrous sodium sulfate and separated by column chromatography or re-crystallization to give 3.275 g product as white solids (partial reddish) in a yield of 73.5%.

Synthesis of Intermediate 17-2

2-methoxy-6-methanesulfonyl naphthalene-1-naphthaldehyde (3.2 g, 0.01211 mol) was added into 250 ml of dry dichloromethane; AlCl$_3$ (18.2529 g, 0.1369 mol) was added in portions, and the mixture was stirred at room temperature and under normal pressure for 36 hrs. After completion of the reaction, the reaction solution was poured into brine and extracted with ethyl acetate. The organic phase was washed with saturated brine for two times, dried over anhydrous sodium sulfate, dried in vacuo to obtain solids, which were separated by column chromatography (PE:EA=3:1) to give 1.250 g of white solids in a yield of 41.25%.

Synthesis of Intermediate 17-3

Compound 6-methanesulfonylnaphthalene-1-formyl-2-naphthol (1.250 g, 0.0062 mol), compound 1-1 (1.851 g, 0.0074 mmol), DABCO (652 mg, 6.2 mmol) were weighed in a 50 ml eggplant flask. Appropriate amount of EA was added to dissolve the solids and heated to reflux. After completion of the reaction, 0.5 g of solids in red was obtained by column chromatography (DCM:PE=1:1) in a yield of 18.6%.

Synthesis of Intermediate 17-4

Compound (0.5 g, 0.0012 mol) was weighed in a 250 mL round bottom flask and THF/CH$_3$OH (10:1, 150 ml) was added to dissolve the solids. Sodium borohydride (459 mg, 0.0121 mmol) was added into the solution in portions. A drying tube was installed at the mouth of the bottle, and the color of reaction solution quickly changed from bright orange to pale yellow. The reaction was performed for 20 mins at room temperature and under normal pressure. After the reaction was completed, water was added into the reaction solution for quenching the reaction, extracted with ethyl acetate, and dried over anhydrous sodium sulfate. The solution was evaporated to dryness in vacuo, and directly used in the next step.

Synthesis of Compound 17

The above obtained compound was dissolved in 30 mL of ethanol, and to the solution was added zinc powder (1.388 g, 21.353 mmol) and 6 mL of 6 N HCl. The reaction was performed at room temperature and under normal pressure for 2-3 hrs. The reaction was monitored by TLC, and after completion of the reaction, the reaction solution was neutralized with saturated aqueous NaHCO$_3$, extracted with dichloromethane, washed by saturated brine, and dried over anhydrous Na$_2$SO$_4$. The solution was evaporated to dryness and separated by column chromatography (PE:EA=1:1) to obtain 450 mg of a white product (crude product).

Compound 17 was obtained from the product of trans-configuration through resolution by chiral column.

$^1$H NMR (500 MHz, DMSO-d$_6$): δ 8.52 (d, J=2.0 Hz, 1H), 8.08 (d, J=9.0 Hz, 1H), 8.01 (d, J=9.0 Hz, 1H), 7.97 (dd, J$_1$=8.5 Hz, J$_2$=2.0 Hz, 1H), 7.72-7.67 (m, 1H), 7.66-7.60 (m, 1H), 7.26 (d, J=9.0 Hz, 1H), 4.99 (d, J=9.5 Hz, 1H), 3.47-3.43 (m, 1H), 3.42 (dd, J$_1$=17.5 Hz, J$_2$=5.5 Hz, 1H), 3.26 (s, 3H), 2.93 (dd, J$_1$=15.8 Hz, J$_2$=10.0 Hz, 1H), 1.74 (s, 2H).

18. trans-(2RS,3RS)-8-morpholin-3-(2,4,5-trifluoro-phenyl)-2,3-dihydro-1H-benzo[f]-chroman-2-amine (compound-18)

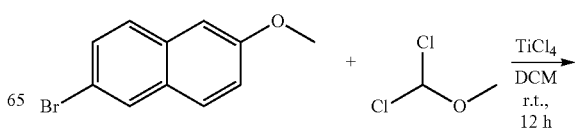

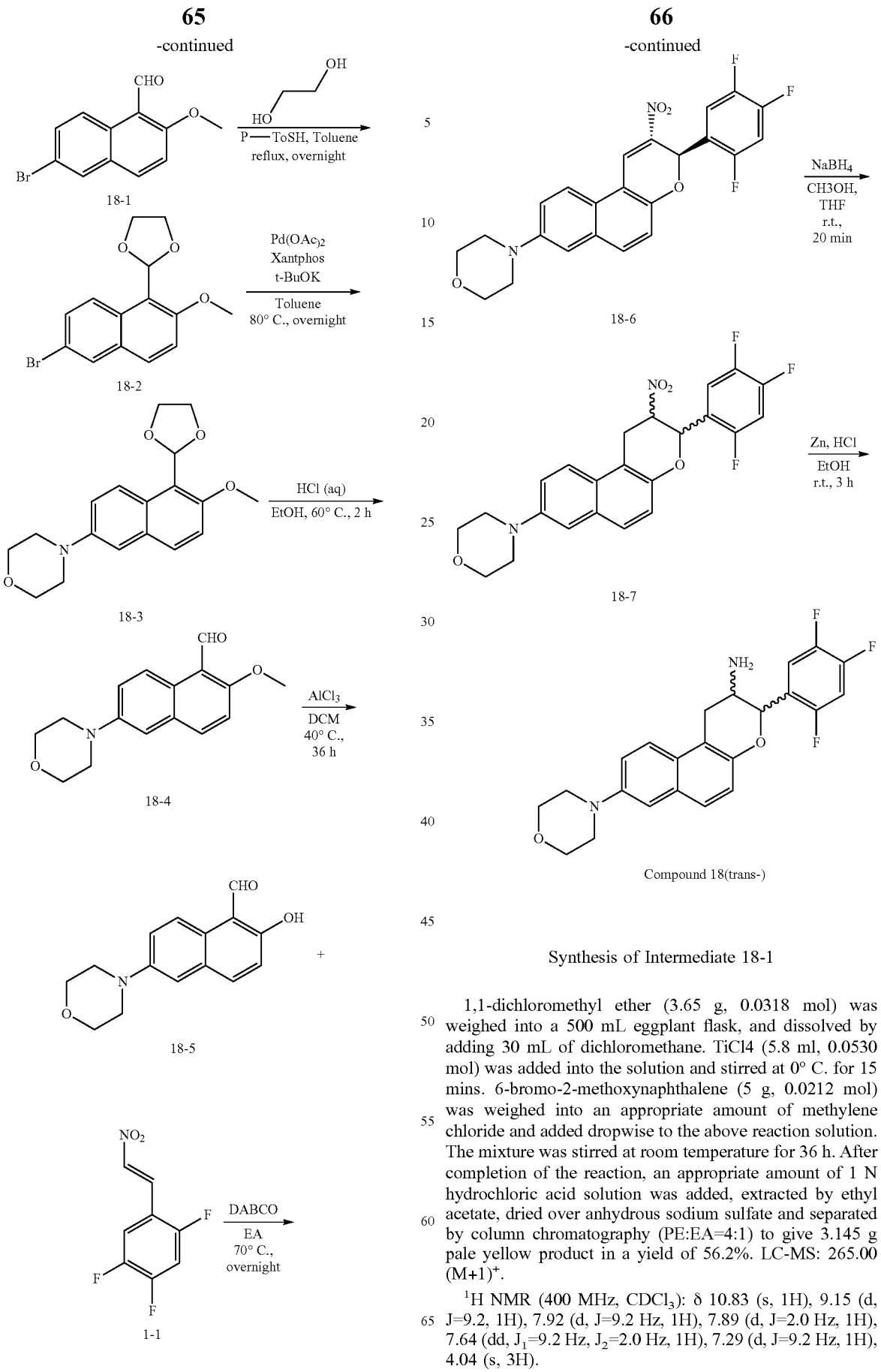

Synthesis of Intermediate 18-1

1,1-dichloromethyl ether (3.65 g, 0.0318 mol) was weighed into a 500 mL eggplant flask, and dissolved by adding 30 mL of dichloromethane. TiCl4 (5.8 ml, 0.0530 mol) was added into the solution and stirred at 0° C. for 15 mins. 6-bromo-2-methoxynaphthalene (5 g, 0.0212 mol) was weighed into an appropriate amount of methylene chloride and added dropwise to the above reaction solution. The mixture was stirred at room temperature for 36 h. After completion of the reaction, an appropriate amount of 1 N hydrochloric acid solution was added, extracted by ethyl acetate, dried over anhydrous sodium sulfate and separated by column chromatography (PE:EA=4:1) to give 3.145 g pale yellow product in a yield of 56.2%. LC-MS: 265.00 $(M+1)^+$.

$^1$H NMR (400 MHz, CDCl$_3$): δ 10.83 (s, 1H), 9.15 (d, J=9.2, 1H), 7.92 (d, J=9.2 Hz, 1H), 7.89 (d, J=2.0 Hz, 1H), 7.64 (dd, J$_1$=9.2 Hz, J$_2$=2.0 Hz, 1H), 7.29 (d, J=9.2 Hz, 1H), 4.04 (s, 3H).

Synthesis of Intermediate 18-2

6-bromo-2-methoxy-1-naphthaldehyde 18-1 (3.145 g, 0.0119 mol), ethylene glycol (4.437 g, 0.0715 mol), p-toluenesulfonic acid (123 mg, 0.0007 mol) were added into a 100 mL reaction flask. An appropriate amount of toluene was added into the bottle, and a water separator was installed. The reaction was performed at 150° C. under reflux conditions overnight. After completion of the reaction, an aqueous NaOH was added into the solution to adjust pH>7, extracted by ethyl acetate, washed by saturated brine, dried over anhydrous sodium sulfate. The solution was evaporated to dryness and separated by column chromatography (PE:EA=6:1) to give 2.275 g of pale yellow solids in a yield of 67%. LC-MS: 309.05 $(M+1)^+$.

Synthesis of Intermediate 18-3

Compound 18-2 (2.28 g, 0.0074 mol), Xantphos (0.214 g, 0.0004 mol), palladium acetate (0.083 g, 0.0004 mol), cesium carbonate (4.824 g, 0.0148 mol) were weighed into a 100 mL two-necked bottle. Argon was used to evacuate the bottle. Under aspiration, 10 mL of toluene was added with a syringe and morpholine (0.967 g, 0.0111 mol) was injected. Aspiration was continued and argon was used to evacuate the bottle for 30 mins. Under argon atmosphere, the reaction was performed at 80° C. overnight. The reaction was monitored by TLC. After the reaction was completed, an appropriate amount of water was added, extracted by ethyl acetate, washed by saturated brine, dried over anhydrous sodium sulfate, and separated by column chromatography (PE:EA=2:1) to give yellow solids, which can be directly used in the next step.

Synthesis of Intermediate 18-4

Compound 27-3 was weighed in a reaction flask, an appropriate amount of ethanol was added, and an appropriate amount of 1N hydrochloric acid was added into the reaction solution. The reaction mixture was heated to reflux at 60° C. for 2-3 h. After the reaction was completed, an appropriate amount of aqueous NaOH was added, and bright yellow solids precipitated. The solids were suction-filtered and the filtrate cake was separated by column chromatography (PE:EA=2:1) to give 1.6 g of bright yellow solids in a two-step yield of 80%. LC-MS: 272.20 (M+1)+.
$^1$H NMR (400 MHz, CDCl$_3$): δ 10.85 (s, 1H), 9.18 (d, J=9.6 Hz, 1H), 7.92 (d, J=8.8 Hz, 1H), 7.38 (dd, J$_1$=9.6 Hz, J$_2$=2.4 Hz, 1H), 7.24 (d, J=9.2 Hz, 1H), 7.05 (d, J=2.4 Hz, 1H), 4.02 (s, 3H), 3.91 (t, J=4.8 Hz, 4H), 3.24 (t, J=4.8 Hz, 4H).

Synthesis of Intermediate 18-5

2-methoxy-6-morpholine-1-naphthalene-formaldehyde 18-4 (1.6 g, 0.0059 mol) was weighed into a 250 mL reaction flask, and an appropriate amount of dry methylene chloride was added to the reaction flask until the substrate was completely dissolved. AlCl$_3$ (4.869 g, 0.03652 mmol) was added into the reaction solution in portions. A drying tube was installed at the mouth of the flask, and the reaction was performed for 36 hrs at room temperature and under normal pressure. After the reaction was completed, a suitable amount of water was added into the reaction solution, stirred for a certain time, extracted with ethyl acetate, washed with saturated brine, and dried over anhydrous sodium sulfate. The solution was evaporated to dryness in vacuo, and 720 mg of yellow solids were obtained by column chromatography (PE:EA=1:1) in a yield of 47%. LC-MS: 258.10 $(M+1)^+$, 256.15 $(M–1)^-$.
$^1$H NMR (400 MHz, DMSO-d$_6$): δ 11.66 (s, 1H), 10.77 (s, 1H), 8.80 (d, J=9.6 Hz, 1H), 7.98 (d, J=8.8 Hz, 1H), 7.47 (dd, J$_1$=9.6 Hz, J$_2$=2.4 Hz, 1H), 7.22 (d, J=2.4 Hz, 1H), 7.16 (d, J=9.2 Hz, 1H), 3.79 (t, J=4.4 Hz, 4H), 3.18 (t, J=4.4 Hz, 4H).

Synthesis of Intermediate 18-6

Compound 2-hydroxy-6-morpholine-1-naphthaldehyde (720 mg, 2.800 mmol), compound 1-1 (568 mg, 2.798 mmol), DABCO (313 mg, 2.795 mmol) were weighed in a 50 ml round bottom flask. Appropriate amount of EA was added and stirred at 70° C. overnight. After completion of the reaction, 350 mg of solids in dark red was obtained by column chromatography (dichloromethane:petroleum ether=1:1) in a yield of 28.3%. LC-MS: 443.10 $(M+1)^+$.
$^1$H NMR (400 MHz, DMSO-d6): δ 8.96 (s, 1H), 8.26 (d, J=9.2 Hz, 1H), 7.86 (d, J=8.8 Hz, 1H), 7.74-7.67 (m, 1H), 7.57-7.50 (m, 2H), 7.23 (d, J=2.0 Hz, 1H), 7.05 (d, J=9.2 Hz, 1H), 6.96 (s, 1H), 3.80 (t, J=4.4 Hz, 4H), 3.22 (t, J=4.4 Hz, 4H).

Synthesis of Intermediate 18-7

Compound 18-6 (350 mg, 0.7917 mmol) was weighed in a 250 mL round bottom flask and THF/CH$_3$OH (10:1, 33 ml) was added to dissolve the solids. Sodium borohydride (200 mg, 5.284 mmol) was added into the solution in portions. A drying tube was installed at the mouth of the bottle, and the reaction was performed for 20 mins at room temperature and under normal pressure. The color of reaction solution changed from dark red to pale yellow. After the reaction was completed, water was added into the reaction solution for quenching the reaction, extracted with ethyl acetate, and dried over anhydrous sodium sulfate. The solution was evaporated to dryness in vacuo, and directly used in the next step.

Synthesis of Compound 18

The above obtained compound was dissolved in 30 mL of ethanol, and to the solution was added zinc powder (835 mg, 12.85 mmol) and 6 mL of 6 N HCl. The reaction was performed at room temperature and under normal pressure for 2-3 hrs. Afterwards, the reaction solution was neutralized with saturated aqueous NaHCO$_3$, extracted with ethyl acetate and dried over anhydrous Na$_2$SO$_4$. The solution was evaporated to dryness and separated by column chromatography (PE:EA=1:2) to obtain 80 mg of a pale yellow product in a two-step yield of 26.7%.
$^1$H NMR (400 MHz, DMSO-d$_6$): δ 7.72 (d, J=9.2 Hz, 1H), 7.70-7.58 (m, 2H), 7.55 (d, J=8.8 Hz, 1H), 7.40 (dd, J$_1$=9.2 Hz, J$_2$=2.0 Hz, 1H), 7.19 (d, J=2.0 Hz, 1H), 6.99 (d, J=8.8 Hz, 1H), 4.87 (d, J=9.2 Hz, 1H), 3.79 (t, J=4.4 Hz, 4H), 3.43-3.39 (m, 2H), 3.18 (t, J=4.4 Hz, 4H), 2.83 (dd, J$_1$=16.4 Hz, J$_2$=10.0 Hz, 1H), 1.74 (s, 2H).

19. (2S,3R)-9-methoxy-8-methanesulfonyl-3-(2,4,5-trifluorophenyl)-2,3-dihydro-1H-benzo[f]-chroman-2-amine (compound-19)

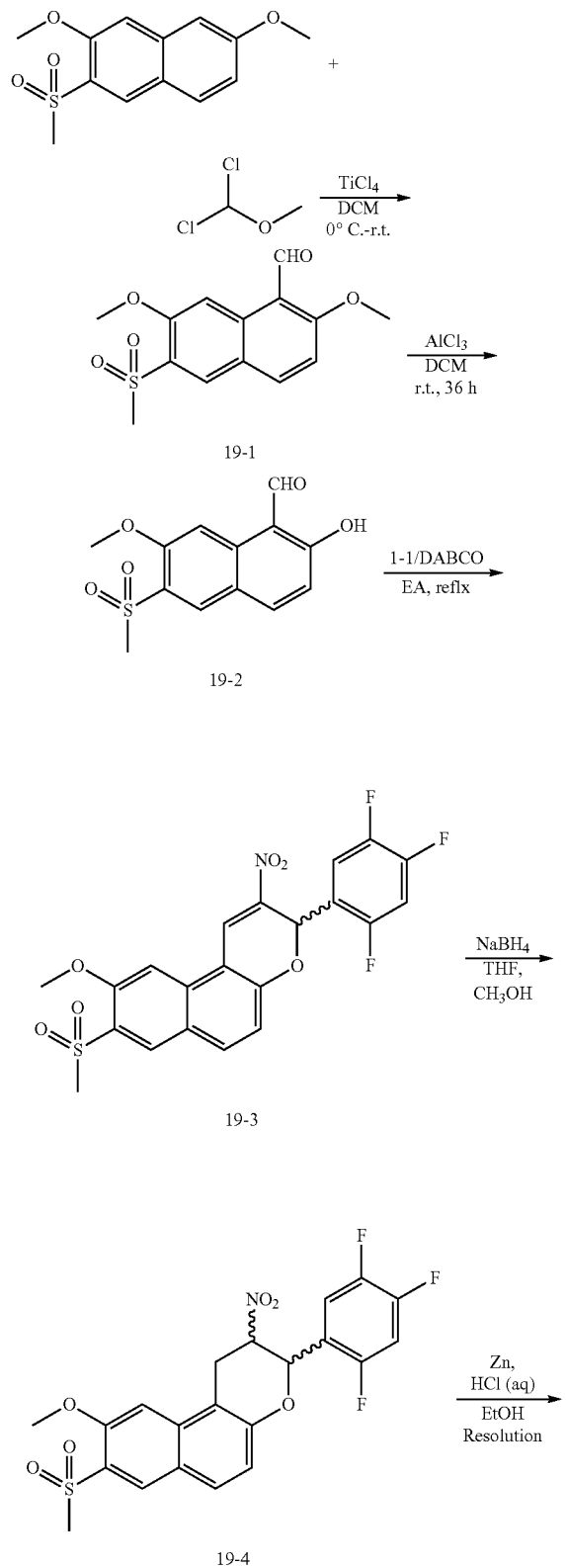

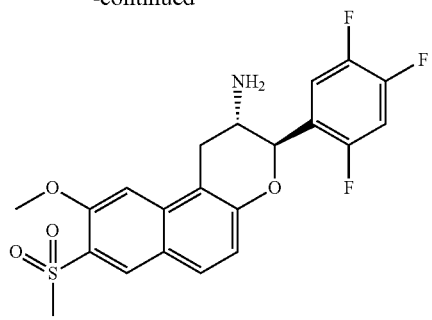

Compound 19

Synthesis of Intermediate 19-1

1,1-dichloromethyl ether (4.8 g, 0.04224 mol) was weighed into a 500 mL eggplant flask, and dissolved by adding 30 mL of dichloromethane. TiCl4 (14 g, 0.07040 mol) was added into the solution and stirred at 0° C. for 15 mins. 2,7-methoxy-6-methanesulfonylnaphthalene (4 g, 0.01693 mol) was weighed into an appropriate amount of methylene chloride and added dropwise to the above reaction solution. The mixture was stirred at room temperature for 36 h. The reaction was monitored by TLC, and after completion of the reaction, an appropriate amount of 1 N hydrochloric acid solution was added to adjust pH<7, extracted by dichloromethane, washed by saturated brine, dried over anhydrous sodium sulfate and separated by column chromatography or re-crystallization to give 3.275 g product as white solids (partial reddish) in a yield of 73.5%.

Synthesis of Intermediate 19-2

Compound 19-1 (3.2 g, 0.01211 mol) was added into 250 ml of dry dichloromethane; AlCl$_3$ (18.2529 g, 0.1369 mol) was added in portions, and the mixture was stirred at room temperature and under normal pressure for 36 hrs. After completion of the reaction, the reaction solution was poured into brine and extracted with ethyl acetate. The organic phase was washed with saturated brine for two times, dried over anhydrous sodium sulfate, dried in vacuo to obtain solids, which were separated by column chromatography (PE:EA=3:1) to give 1.250 g of white solids in a yield of 41.25%.

Synthesis of Intermediate 19-3

Compound 19-2 (1.250 g, 0.0062 mol), compound 1-1 (1.851 g, 0.0074 mmol), DABCO (652 mg, 6.2 mmol) were weighed in a 50 ml eggplant flask. Appropriate amount of EA was added to dissolve the solids and heated to reflux. After completion of the reaction, 0.5 g of solids in red was obtained by column chromatography (DCM:PE=1:1) in a yield of 18.6%.

Synthesis of Intermediate 19-4

Compound 19-3 (0.5 g, 0.0012 mol) was weighed in a 250 mL round bottom flask and THF/CH$_3$OH (10:1, 150 ml) was added to dissolve the solids. Sodium borohydride (459 mg, 0.0121 mmol) was added into the solution in portions. A drying tube was installed at the mouth of the bottle, and the color of reaction solution quickly changed from bright orange to pale yellow. The reaction was performed for 20 mins at room temperature and under normal pressure. After the reaction was completed, water was added into the reaction solution for quenching the reaction, extracted with ethyl acetate, and dried over anhydrous sodium sulfate. The solution was evaporated to dryness in vacuo to give white solids, which can be directly used in the next step.

Synthesis of Compound 19

The above obtained compound was dissolved in 30 mL of ethanol, and to the solution was added zinc powder (1.388 g, 21.353 mmol) and 6 mL of 6 N HCl. The reaction was performed at room temperature and under normal pressure for 2-3 hrs. The reaction was monitored by TLC, and after completion of the reaction, the reaction solution was neutralized with saturated aqueous NaHCO$_3$, extracted with dichloromethane, washed by saturated brine, and dried over anhydrous Na$_2$SO$_4$. The solution was evaporated to dryness and separated by column chromatography (PE:EA=1:1) to obtain 450 mg of a white product (crude product).

Compound 19 was obtained from the product of trans-configuration through resolution by chiral column.

$^1$H NMR (500 MHz, DMSO-d$_6$): δ 8.41 (s, 1H), 7.92 (d, J=9.0 Hz, 1H), 7.72-7.67 (m, 1H), 7.65-7.60 (m, 1H), 7.33 (s, 1H), 7.05 (d, J=9.0 Hz, 1H), 4.97 (d, J=9.0 Hz, 1H), 4.08 (s, 3H), 3.46-3.42 (m, 1H), 3.39 (dd, J$_1$=16.3 Hz, J$_2$=5.0 Hz, 1H), 3.30 (s, 3H), 2.86 (dd, J$_1$=16.0 Hz, J$_2$=9.5 Hz, 1H), 1.67 (s, 2H).

20. N-((2RS,3RS)-2-amino-9-methoxy-3-(2,4,5-trifluorophenyl)-2,3-dihydro-1H-benzo[f]-chroman-8)-methanesulfonamide (compound-20)

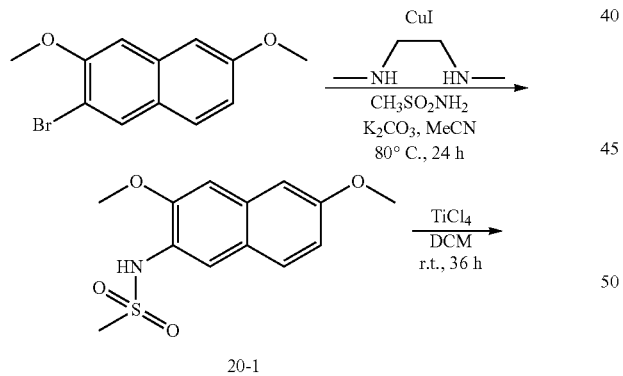

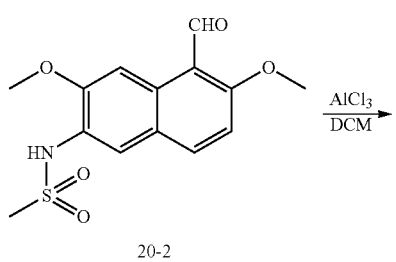

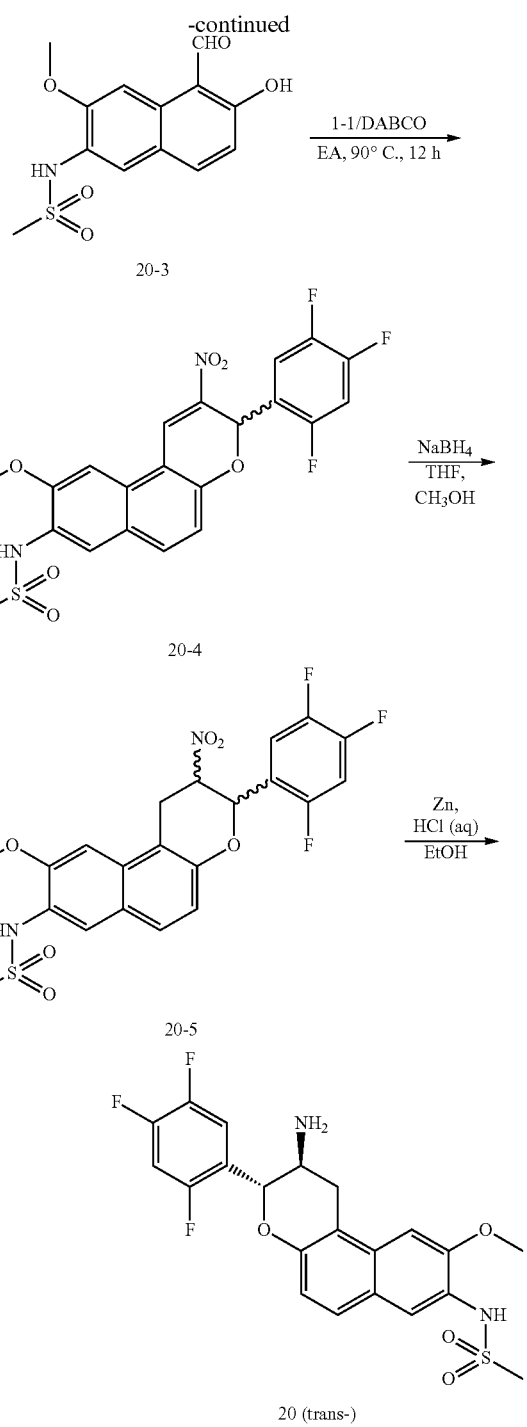

Synthesis of Intermediate 20-1

Compound 2-bromo-3,6-dimethoxynaphthalene (3 g, 0.0113 mol), N,N'-dimethylethylenediamine (0.509 g, 0.00565 mol), cuprous iodide (0.215 g, 0.0011 mol), potassium phosphate (4.68 g, 0.03384 mol), methanesulfonamide (1.61 g, 0.0169 mol) were weighed into a 250 mL two-necked bottle. Argon was used to evacuate the bottle. Under aspiration, 95 mL of acetonitrile was added with a syringe. Aspiration was continued and argon was used to evacuate the bottle for 30 mins. Under argon atmosphere, the reaction was performed at 80° C. for 36 hrs. The reaction was monitored by TLC. After the reaction was completed, water was added for quenching the reaction, extracted by ethyl acetate, washed by saturated brine, and dried over anhydrous sodium sulfate. The solution was evaporated to dryness and separated by column chromatography (PE:EA=3:1) to give 1.89 g of white solids in a yield of 59.6%. LC-MS: 282.10 (M+1)⁺, 280.05 (M−1)⁺.

¹H NMR (400 MHz, CDCl₃): δ 7.86 (s, 1H), 7.65 (d, J=9.6 Hz, 1H), 7.09 (s, 1H), 7.05 (s, 1H), 7.04 (d, J=3.2 Hz, 1H), 6.94 (s, 1H), 3.98 (s, 3H), 3.90 (s, 3H), 2.97 (s, 3H).

Synthesis of Intermediate 20-2

1,1-dichloromethyl ether (1.10 g, 0.0096 mol) was weighed into a 100 mL eggplant flask, and dissolved by adding 15 mL of dichloromethane. TiCl₄ (3.02 g, 0.0159 mol) was added into the solution and stirred at 0° C. for 15 mins. N-(3,6-dimethoxynaphthalene-2-)methanesulfonamide 62 (1.79 g, 0.0064 mol) was weighed into an appropriate amount of methylene chloride and added dropwise to the above reaction solution. The mixture was stirred at room temperature overnight. The reaction was monitored by TLC, and after completion of the reaction, an appropriate amount of 1 N hydrochloric acid solution was added to adjust pH=5-6, extracted by dichloromethane, washed by saturated brine, dried over anhydrous sodium sulfate and separated by column chromatography to give 1.5 g of orange product in a yield of 76.1%. LC-MS: 310.10 (M+1)⁺, 308.10 (M−1)⁺.

¹H NMR (400 MHz, DMSO-d₆): δ 10.75 (s, 1H), 9.15 (s, 1H), 8.76 (s, 1H), 8.22 (d, J=9.2 Hz, 1H), 7.82 (s, 1H), 7.41 (d, J=9.2 Hz, 1H), 4.04 (s, 3H), 3.95 (s, 3H), 3.04 (s, 3H).

Synthesis of Intermediate 20-3

Anhydrous AlCl₃ (4 g, 0.0299 mol) was weighed into a 250 mL eggplant bottle. Under a condition of cooling, 60 mL of DCM was added to the flask. After the solid was dissolved, N-(5-formyl-3,6-dimethoxynaphthalene-2-)methanesulfonamide 20-2 (1.85 g, 0.0060 mol) was added into the flask at room temperature and under normal atmospheric pressure. The reaction was carried out under the conditions of normal temperature and atmospheric pressure. The reaction was monitored by TLC, and after the reaction was completed, 1 N HCl was added into the reaction solution, extracted with EA, and separated by column chromatography to give 1.3 g of white solids in a yield of 73%. LC-MS: 296.10 (M+1)⁺, 294.10 (M−1)⁻.

¹H NMR (400 MHz, DMSO-d₆): δ 12.03 (s, 1H), 10.81 (s, 1H), 9.11 (s, 1H), 8.65 (s, 1H), 8.11 (d, J=9.2 Hz, 1H), 7.92 (s, 1H), 7.15 (d, J=8.8 Hz, 1H), 3.92 (s, 3H), 3.50 (s, 3H).

Synthesis of Intermediate 20-4

N-(5-formyl-3-dimethoxy-6-hydroxynaphthalene-2-)methanesulfonamide 20-3 (1 g, 0.0034 mol), (E)-1-(2,4,5-trifluorophenyl)-2-nitroolefin 1-1 (688 mg, 0.0034 mol), DABCO (88 mg, 0.007 mmol) were added into a 100 mL eggplant flask. 35 mL of EA was added, and the reaction was performed at 90° C. overnight. The reaction was monitored by TLC. After the reaction was completed, the reaction mixture was separated by column chromatography (PE:DCM=1:3) to give 420 mg of red solids in a yield of 25.8%. LC-MS: 481.15 (M+1)⁺, 479.10 (M−1)⁻.

¹H NMR (400 MHz, DMSO-d6): δ 9.18 (s, 1H), 9.16 (s, 1H), 7.95 (d, J=8.8 Hz, 1H), 7.83 (s, 1H), 7.89 (s, 1H), 7.75-7.68 (m, 1H), 7.56-7.49 (m, 1H), 6.99 (s, 1H), 6.98 (d, J=9.6 Hz, 1H), 4.11 (s, 3H), 3.06 (s, 3H).

Synthesis of Intermediate 20-5

N-[2-(2,4,5-trifluorophenyl)-3-nitro-6-methoxy-2H-benzo[f]-chroman-7-]methanesulfonamide 65 (420 mg, 0.8749 mmol) was weighed in a 100 mL round bottom flask and THF/CH₃OH (10:1, 35 ml) was added to dissolve the solids. Sodium borohydride (132 mg, 3.4996 mmol) was added into the solution in portions, and the color of reaction solution quickly changed from orange to pale yellow. A drying tube was installed at the mouth of the bottle, and the reaction was performed for 20 mins at room temperature and under normal pressure. After the reaction was completed, water was added into the reaction solution for quenching the reaction, extracted with ethyl acetate, and dried over anhydrous sodium sulfate. The solution was evaporated to dryness in vacuo, and directly used in the next step.

Synthesis of Compound 20

The above obtained crude N-[2-(2,4,5-trifluorophenyl)-3-nitro-6-methoxy-3,4-dihydro-2H-benzo[f]-chroman-7-]methanesulfon amide 66 was dissolved in 20 mL of ethanol, and to the solution was added zinc powder (2.6 g, 0.040 mol) and 2.6 mL of 6 N HCl. The reaction was performed at room temperature and under normal pressure for 2-3 hrs. The reaction was monitored by TLC, and after completion of the reaction, the reaction solution was neutralized with saturated aqueous NaHCO₃, extracted with ethyl acetate, washed by saturated brine, and dried over anhydrous Na₂SO₄. The solution was evaporated to dryness and separated by column chromatography (PE:EA=1:2).

21. (2S,3R)-2-amino-9-methoxy-3-(2,4,5-trifluorophenyl)-2,3-dihydro-1H-benzo[f]-chroman-8-nitrile (compound-21)

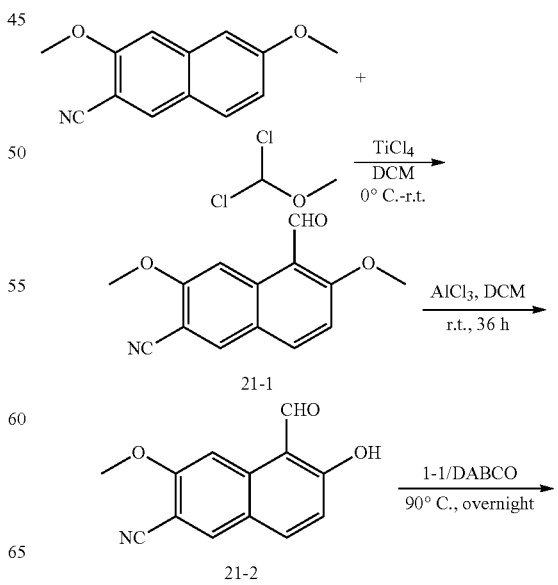

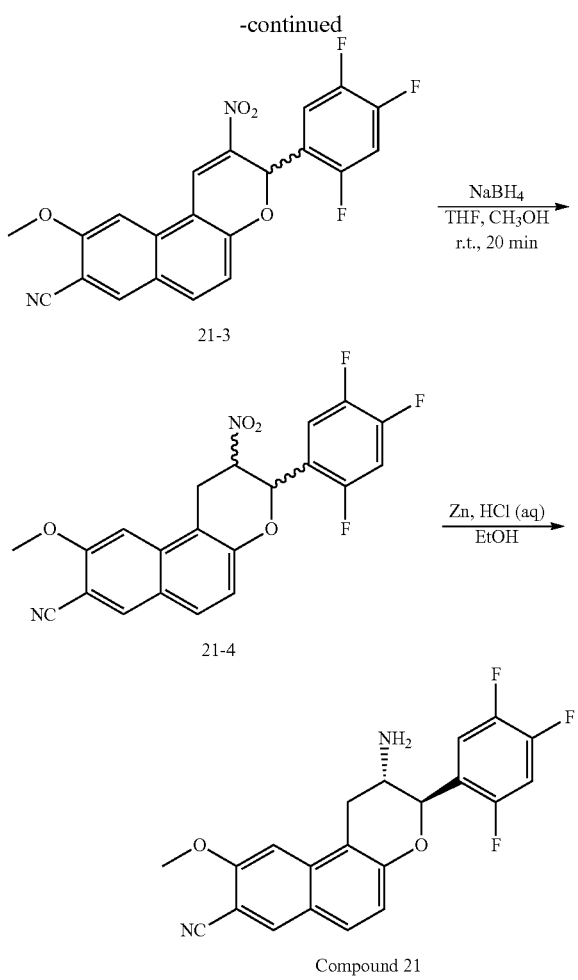

Synthesis of Intermediate 21-1

1,1-dichloromethyl ether (4.8 g, 0.04224 mol) was weighed into a 500 mL eggplant flask, and dissolved by adding 30 mL of dichloromethane. TiCl4 (14 g, 0.07040 mol) was added into the solution and stirred at 0° C. for 15 mins. 3,6-dimethoxynaphthalonitrile (4 g, 0.02816 mol) was weighed into an appropriate amount of methylene chloride and added dropwise to the above reaction solution. The mixture was stirred at room temperature for 36 h. The reaction was monitored by TLC, and after completion of the reaction, an appropriate amount of 1 N hydrochloric acid solution was added to adjust pH<7, extracted by dichloromethane, washed by saturated brine, dried over anhydrous sodium sulfate and separated by column chromatography or re-crystallization to give 4.275 g of white product in a yield of 94.5%.

$^1$HNMR (400 MHz, DMSO-$d_6$): δ 10.71 (s, 1H), 8.77 (s, 1H), 8.50 (s, 1H), 8.29 (d, J=8.4 Hz, 1H), 7.55 (d, J=8.8 Hz, 1H), 4.10 (s, 3H), 3.98 (s, 3H).

Synthesis of Intermediate 21-2

6-cyano-2,7-dimethoxy-1-naphthalene formaldehyde 21-1 (3.3 g, 0.01369 mol) was weighed into a 250 ml reaction flask and 150 ml of dry dichloromethane was added. AlCl$_3$ (18.2529 g, 0.1369 mol) was added in portions, and the mixture was stirred at room temperature and under normal pressure for 36 hrs. After completion of the reaction, the reaction solution was poured into brine and extracted with ethyl acetate. The organic phase was washed with saturated brine for two times, dried over anhydrous sodium sulfate, dried in vacuo to obtain solids, which were separated by column chromatography (PE:EA=3:1) to give 1.250 g of pale red solids in a yield of 40.2%.

$^1$HNMR (400 MHz, DMSO-$d_6$): δ 12.14 (s, 1H), 10.68 (s, 1H), 8.58 (s, 1H), 8.35 (s, 1H), 8.03 (d, J=9.2 Hz, 1H), 7.11 (d, J=9.2 Hz, 1H), 3.93 (s, 3H).

Synthesis of Intermediate 21-3

Compound 6-cyano-2-hydroxy-7-methoxy-1-naphthaldehyde 21-2 (1.250 g, 0.0055 mol), (E)-1-(2,4,5-trifluorophenyl)-2-nitroolefin 1-1 (1.341 g, 0.0066 mol), DABCO (616 mg, 5.5 mmol) were weighed in a 50 ml eggplant flask. Appropriate amount of EA was added to dissolve the solids and the reaction was performed at 90° C. overnight. After completion of the reaction, 1 g of solids in orange yellow was obtained by column chromatography (DCM:PE=1:1) in a yield of 44.1%.

$^1$H NMR (400 MHz, DMSO-$d_6$): δ 9.18 (s, 1H), 8.48 (s, 1H), 8.03 (d, J=9.2 Hz, 1H), 7.92 (s, 1H), 7.76-7.70 (m, 1H), 7.62-7.55 (m, 1H), 7.10 (d, J=8.8 Hz, 1H), 7.04 (s, 1H), 4.16 (s, 1H).

Synthesis of Intermediate 21-4

2-(2,4,5-trifluorophenyl)-3-nitro-6-methoxy-3H-benzo[f]chroman-7-nitrile 21-3 (2.2 g, 0.0053 mol) was weighed in a 250 mL round bottom flask and THF/CH$_3$OH (10:1, 150 ml) was added to dissolve the solids. Sodium borohydride (606 mg, 0.0160 mmol) was added into the solution in portions. The color of reaction solution quickly changed from bright orange to pale yellow. A drying tube was installed at the mouth of the bottle. The reaction was performed for 20 mins at room temperature and under normal pressure. After the reaction was completed, water was added into the reaction solution for quenching the reaction, extracted with ethyl acetate, and dried over anhydrous sodium sulfate. The solution was evaporated to dryness in vacuo to give white solids, which can be directly used in the next step.

Synthesis of Compound 21

The crude 2-(2,4,5-trifluorophenyl)-3-nitro-6-methoxy-3,4-dihydro-2H-benzo[f]chroman-7-nitrile 59 obtained by above method 1 was dissolved in 80 mL of ethanol, and to the solution was added zinc powder (3.45 g, 0.053 mol) and 16 mL of 6 N HCl. The reaction was performed at room temperature and under normal pressure for 2-3 hrs. The reaction was monitored by TLC, and after completion of the reaction, the reaction solution was neutralized with saturated aqueous NaHCO$_3$, extracted with ethyl acetate, washed by saturated brine, and dried over anhydrous Na$_2$SO$_4$. The solution was evaporated to dryness and separated by column chromatography (PE:EA=1:1) to obtain 670 mg of a white product in a yield of 32.7%.

Compound 21 was obtained from the product of trans-configuration through resolution by chiral column. LCMS (M+1)+, 384.21.

$^1$H NMR (500 MHz, DMSO-$d_6$): δ 8.41 (s, 1H), 7.75 (d, J=9.0 Hz, 1H), 7.69-7.65 (m, 1H), 7.64-7.58 (m, 1H), 7.25 (s, 1H), 7.04 (d, J=9.0 Hz, 1H), 4.96 (d, J=9.0 Hz, 1H), 4.03

(s, 3H), 3.44-3.39 (m, 1H), 3.35 (dd, $J_1$=16.5 Hz, $J_2$=5.5 Hz, 1H), 2.82 (dd, $J_1$=16.5 Hz, $J_2$=10.0 Hz, 1H), 1.72 (s, 2H).

22. trans-(2RS,3RS)-9-methoxy-3-(2-fluorophenyl)-2,3-dihydro-1H-benzo[f]-chroman-2-amine (compound-22)

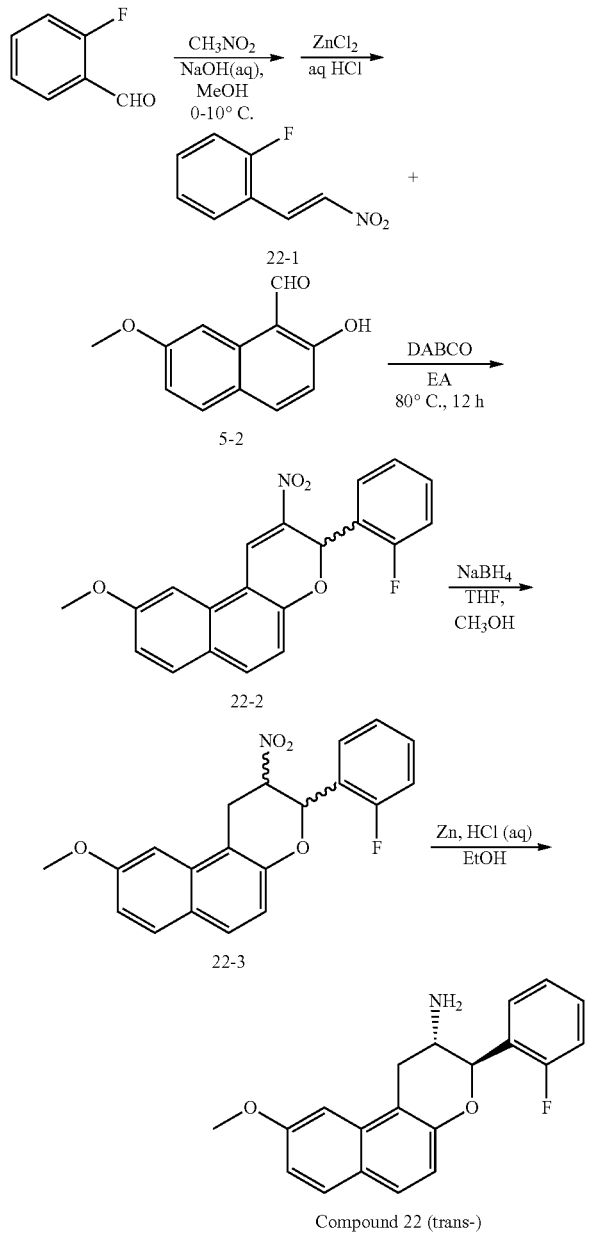

Synthesis of Intermediate 22-1

2-fluorobenzaldehyde (7.747 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pressure, and the filter cake was washed with 40% methanol solution for several times to give 8.1 g of a pale yellow product in a yield of 77.7%. GC-MS: 167.

$^1$H NMR (400 MHz, CDCl$_3$): δ 8.06 (d, J=14.0, 1H), 7.74 (d, J=14.0, 1H), 7.54 (d, J=7.6 Hz, 1H), 7.49 (t, J=6.8 Hz, 1H), 7.25 (t, J=6.8 Hz, 1H), 7.19 (t, J=9.6 Hz, 1H).

Synthesis of Intermediate 22-2

7-methoxy-2-hydroxy-1-naphthaldehyde 5-2 (4.85 g, 24.003 mmol), compound 22-1 (6 g, 35.928 mmol) was weighed into a 50 mL round bottom flask, 20 ml of ethyl acetate was added, and the solids were dissolved by heating. Afterwards, DABCO (27 g, 24.107 mmol) was added and heated to reflux at 80° C. for 12 h, and the color of the solution turned orange. The reaction mixture was suction-filtered and washed with ethyl acetate to give 2.38 g of product in a yield of 28%.

$^1$H NMR (400 MHz, DMSO-d$_6$): δ 9.18 (s, 1H), 7.92 (d, J=8.8 Hz, 1H), 7.81 (d, J=8.8 Hz, 1H), 7.78 (d, J=2.0 Hz, 1H), 7.44 (m, 1H), 7.36 (t, J=3.6 Hz, 1H), 7.32 (d, J=8.8 Hz, 1H), 7.11 (m, 1H), 7.03 (s, 1H), 6.94 (d, J=8.8 Hz, 1H), 4.02 (s, 3H), 2.88 (s, 1H).

Synthesis of Intermediate 22-3

Compound 6 (2.38 g, 6.779 mol) was weighed in a 50 mL round bottom flask and THF/CH$_3$OH (10:1, 20 ml) was added to dissolve the solids. Sodium borohydride (317 mg, 11.391 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 22

The above obtained compound was dissolved in 50 mL of ethanol, and to the solution was added zinc powder (4.53 g, 69.692 mmol) and 8 mL of 6 N HCl. The reaction was performed at 50° C. for 2 hrs. The zinc powder was filtered off through diatomite. The solvent was evaporated to dryness. The obtained residue was dissolved in saturated aqueous sodium hydroxide, extracted with dichloromethane, and dried over anhydrous sodium sulfate. The solution was evaporated to dryness and separated by column chromatography (PE:EA=2:1) to give 150 mg of white product. LC-MS: 324.15 (M+1)$^+$.

$^1$H NMR (400 MHz, DMSO-d$_6$): δ 7.76 (d, J=8.8 Hz, 1H), 7.63 (d, J=8.8 Hz, 1H), 7.54 (t, J=7.6 Hz, 1H), 7.45 (m, 1H), 7.30 (d, J=2.4 Hz, 1H), 7.26 (d, J=8.0 Hz, 1H), 7.13 (d, J=2.0 Hz, 1H), 7.05 (m, 1H), 6.93 (d, J=8.8 Hz, 1H), 5.01 (d, J=8.8 Hz, 1H), 3.90 (s, 3H), 2.85 (m, 1H), 1.79 (d, J=3.2 Hz, 2H).

23. trans-(2RS,3RS)-9-methoxy-3-(4-fluorophenyl)-2,3-dihydro-1H-benzo[f]-chroman 2-amine (compound-23)

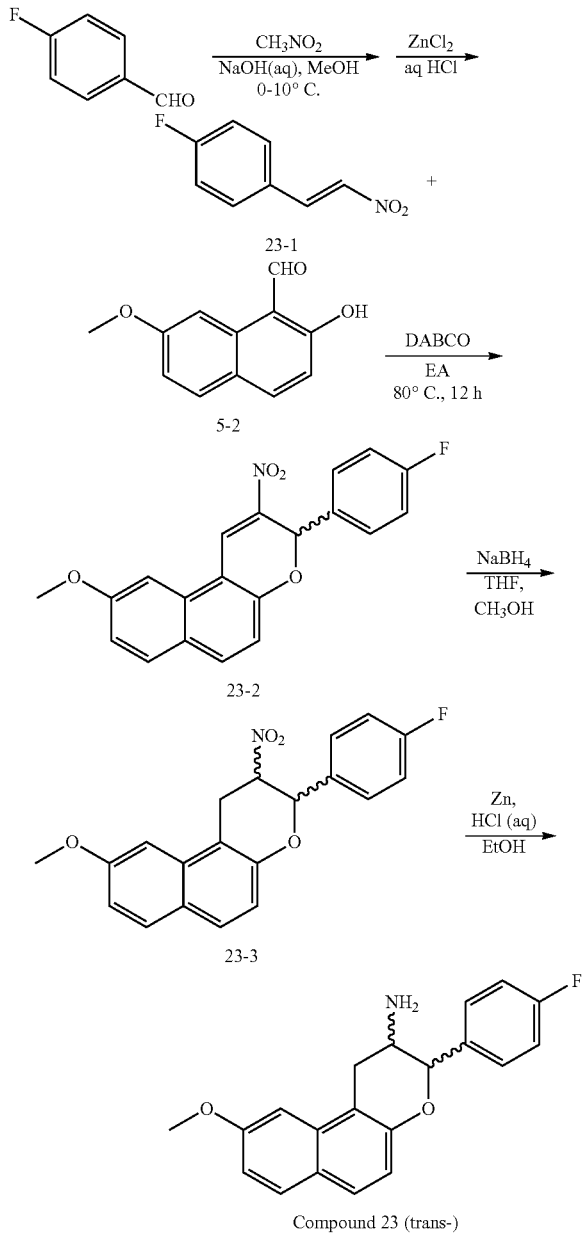

Synthesis of Intermediate 23-1

4-fluorobenzaldehyde (7.747 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pressure, and the filter cake was washed with 40% methanol solution for several times to give 8.1 g of product in a yield of 77.7%. GC-MS: 167.

$^1$H NMR (400 MHz, DMSO-$d_6$): δ 8.23 (d, J=13.6, 1H), 8.16 (d, J=13.6, 1H), 7.96 (m, 2H), 7.35 (t, J=8.8 Hz, 2H).

Synthesis of Intermediate 23-2

7-methoxy-2-hydroxy-1-naphthaldehyde (4.85 g, 24.003 mmol), compound 5-2 (6 g, 35.928 mmol) was weighed into a 50 mL round bottom flask, 20 ml of ethyl acetate was added, and the solids were dissolved by heating. Afterwards, DABCO (27 g, 24.107 mmol) was added and heated to reflux at 80° C. for 12 h, and the color of the solution turned orange. The reaction mixture was suction-filtered and washed with ethyl acetate to give 2.38 g of product in a yield of 28%.

$^1$H NMR (400 MHz, DMSO-$d_6$): δ 9.12 (s, 1H), 7.93 (d, J=8.8 Hz, 1H), 7.81 (d, J=8.8 Hz, 1H), 7.74 (s, 1H), 7.51 (m, 2H), 7.19 (t, J=8.4 Hz, 2H), 7.12 (dd, $J_1$=9.2 Hz, $J_2$=2.0 Hz, 1H), 6.98 (d, J=8.8 Hz, 1H), 6.80 (s, 1H), 4.01 (s, 3H).

Synthesis of Intermediate 23-3

Compound 23-2 (2.38 g, 6.779 mol) was weighed in a 50 mL round bottom flask and THF/CH$_3$OH (10:1, 20 ml) was added to dissolve the solids. Sodium borohydride (317 mg, 11.391 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 23

The above obtained compound was dissolved in 50 mL of ethanol, and to the solution was added zinc powder (4.53 g, 69.692 mmol) and 8 mL of 6 N HCl. The reaction was performed at 50° C. for 2 hrs. The zinc powder was filtered off through diatomite. The solvent was evaporated to dryness. The obtained residue was dissolved in saturated aqueous sodium hydroxide, extracted with dichloromethane, and dried over anhydrous sodium sulfate. The solution was evaporated to dryness and separated by column chromatography (PE:EA=2:1) to give 150 mg of white product. LC-MS: 324.15 (M+1)$^+$.

$^1$H NMR (400 MHz, DMSO-$d_6$): δ 7.75 (d, J=8.8 Hz, 1H), 7.63 (d, J=8.8 Hz, 1H), 7.52 (m, 2H), 7.25 (t, J=8.8 Hz, 2H), 7.11 (d, J=2.0 Hz, 1H), 7.04 (m, 1H), 6.94 (d, J=8.8 Hz, 1H), 4.71 (d, J=8.8 Hz, 1H), 3.90 (s, 3H), 2.78 (m, 1H), 1.54 (s, 2H).

24. trans-(2RS,3RS)-9-methoxy-3-(2,4-difluorophenyl)-2,3-dihydro-1H-benzo[f]-chroman-2-amine (compound-24)

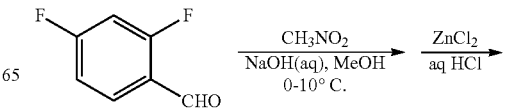

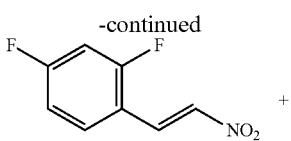

¹H NMR (400 MHz, DMSO-d₆): δ 8.14 (d, J=13.6, 1H), 8.09 (d, J=4.8, 1H), 8.06 (d, J=2.8 Hz, 1H), 7.49 (m, 1H), 7.25 (t, J=6.8 Hz, 1H), 7.28 (m, 1H).

Synthesis of Intermediate 24-2

7-methoxy-2-hydroxy-1-naphthaldehyde (2.7 g, 13.362 mmol), compound 5-2 (3.7 g, 19.997 mmol) was weighed into a 50 mL round bottom flask, 20 ml of ethyl acetate was added, and the solids were dissolved by heating. Afterwards, DABCO (1.5 g, 13.393 mmol) was added and heated to reflux at 80° C. for 12 h, and the color of the solution turned orange. The reaction mixture was suction-filtered and washed with ethyl acetate to give 1.5 g of product in a yield of 30.4%.

¹H NMR (400 MHz, DMSO-d₆): δ 9.17 (s, 1H), 7.93 (d, J=8.8 Hz, 1H), 7.82 (d, J=8.8 Hz, 1H), 7.77 (d, J=2.0 Hz, 1H), 7.40 (m, 2H), 7.13 (dd, J₁=8.8 Hz, J₂=2.4 Hz, 1H), 6.99 (s, 1H), 6.94 (d, J=8.8 Hz, 1H), 4.02 (s, 3H), 2.81 (s, 1H).

Synthesis of Intermediate 24-3

Compound 24-2 (2.50 g, 6.779 mol) was weighed in a 50 mL round bottom flask and THF/CH₃OH (10:1, 20 ml) was added to dissolve the solids. Sodium borohydride (317 mg, 11.391 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 24

The above obtained compound was dissolved in 50 mL of ethanol, and to the solution was added zinc powder (4.53 g, 69.692 mmol) and 8 mL of 6 N HCl. The reaction was performed at 50° C. for 2 hrs. The zinc powder was filtered off through diatomite. The solvent was evaporated to dryness. The obtained residue was dissolved in saturated aqueous sodium hydroxide, extracted with dichloromethane, and dried over anhydrous sodium sulfate. The solution was evaporated to dryness and separated by column chromatography (PE:EA=2:1) to give 160 mg of white product. LC-MS: 342.20 (M+1)⁺.

¹H NMR (400 MHz, DMSO-d₆): δ 7.78 (d, J=8.8 Hz, 1H), 7.65 (d, J=9.2 Hz, 1H), 7.60 (t, J=6.8 Hz, 1H), 7.32 (m, 1H), 7.17 (m, 1H), 7.11 (s, 1H), 7.05 (dd, J₁=8.8 Hz, J₂=2.4 Hz, 1H), 6.93 (d, J=8.8 Hz, 1H), 5.04 (d, J=8.8 Hz, 1H), 3.91 (s, 3H), 2.90 (m, 1H).

Synthesis of Intermediate 24-1

2,4-difluorobenzaldehyde (8.871 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pressure, and the filter cake was washed with 40% methanol solution for several times to give 8.1 g of product in a yield of 77.7%. GC-MS: 185.

25. trans-(2RS,3RS)-9-methoxy-3-(2,5-difluorophenyl)-2,3-dihydro-1H-benzo[f]-chroman-2-amine (compound-25)

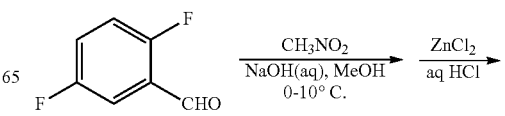

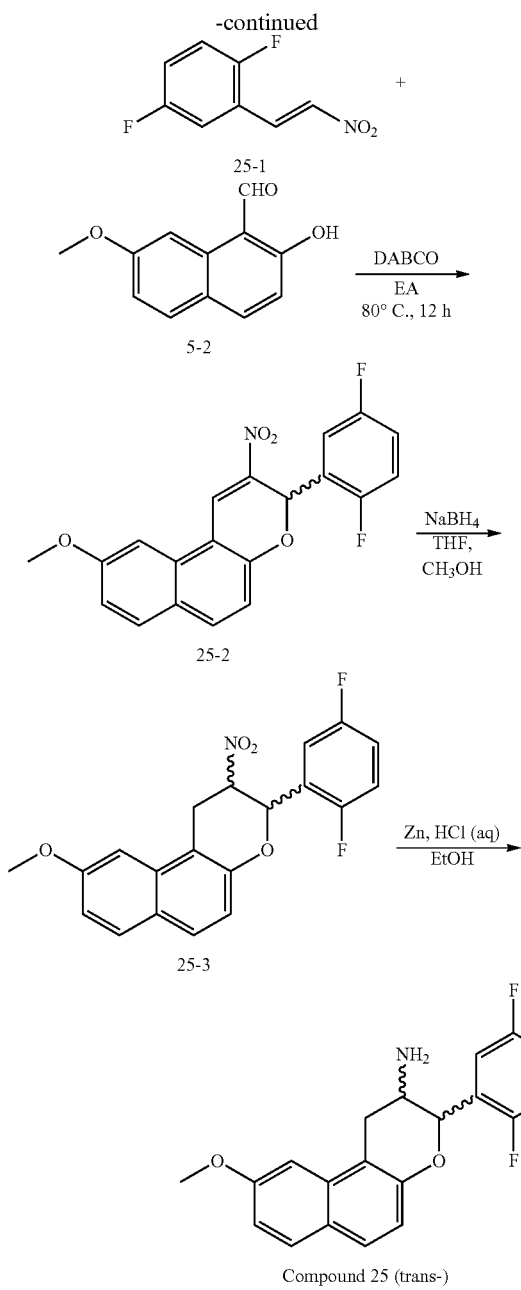

sure, and the filter cake was washed with 40% methanol solution for several times to give 8.1 g of product in a yield of 77.7%. GC-MS: 185.

$^1$H NMR (400 MHz, DMSO-d$_6$): δ 8.21 (d, J=13.6, 1H), 8.04 (d, J=13.6, 1H), 7.92 (m, 1H), 7.47 (m, 2H).

Synthesis of Intermediate 25-2

7-methoxy-2-hydroxy-1-naphthaldehyde (2.7 g, 13.362 mmol), compound 5-2 (3.7 g, 19.997 mmol) was weighed into a 50 mL round bottom flask, 20 ml of ethyl acetate was added, and the solids were dissolved by heating. Afterwards, DABCO (1.5 g, 13.393 mmol) was added and heated to reflux at 80° C. for 12 h, and the color of the solution turned orange. The reaction mixture was suction-filtered and washed with ethyl acetate to give 1.5 g of product in a yield of 30.4%.

$^1$H NMR (400 MHz, DMSO-d$_6$): δ 9.17 (s, 1H), 7.93 (d, J=8.8 Hz, 1H), 7.82 (d, J=9.2 Hz, 1H), 7.77 (d, J=2.0 Hz, 1H), 7.40 (m, 2H), 7.13 (dd, J$_1$=9.2 Hz, J$_2$=2.4 Hz, 1H), 6.99 (s, 1H), 6.94 (d, J=8.8 Hz, 1H), 4.02 (s, 3H), 2.78 (s, 1H).

Synthesis of Intermediate 25-3

Compound 25-2 (2.50 g, 6.779 mol) was weighed in a 50 mL round bottom flask and THF/CH$_3$OH (10:1, 20 ml) was added to dissolve the solids. Sodium borohydride (317 mg, 11.391 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 25

The above obtained compound was dissolved in 50 mL of ethanol, and to the solution was added zinc powder (4.53 g, 69.692 mmol) and 8 mL of 6 N HCl. The reaction was performed at 50° C. for 2 hrs. The zinc powder was filtered off through diatomite. The solvent was evaporated to dryness. The obtained residue was dissolved in saturated aqueous sodium hydroxide, extracted with dichloromethane, and dried over anhydrous sodium sulfate. The solution was evaporated to dryness and separated by column chromatography (PE:EA=2:1) to give 170 mg of white product. LC-MS: 342.20 (M+1)$^+$.

$^1$H NMR (400 MHz, DMSO-d$_6$): δ 7.68 (d, J=8.8 Hz, 1H), 7.56 (d, J=8.8 Hz, 1H), 7.30 (m, 1H), 7.23 (m, 2H), 7.04 (s, 1H), 6.97 (dd, J$_1$=8.8 Hz, J$_2$=2.4 Hz, 1H), 6.85 (d, J=8.8 Hz, 1H), 4.89 (d, J=8.8 Hz, 1H), 3.82 (s, 3H), 3.21 (m, 1H), 2.76 (m, 1H).

26. trans-(2RS,3RS)-9-methoxy-3-(2-chlorophenyl)-2,3-dihydro-1H-benzo[f]-chroman-2-amine (compound-26)

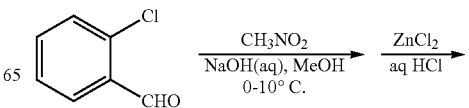

Synthesis of Intermediate 25-1

2,4-difluorobenzaldehyde (8.871 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pres-

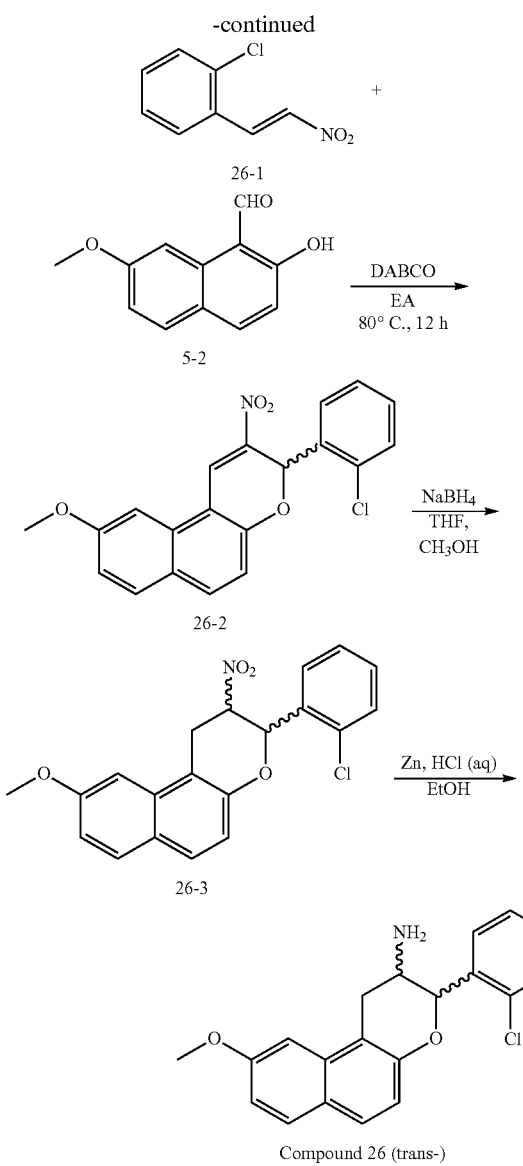

Synthesis of Intermediate 26-2

7-methoxy-2-hydroxy-1-naphthaldehyde (2.7 g, 13.362 mmol), compound 5-2 (3.7 g, 19.997 mmol) was weighed into a 50 mL round bottom flask, 20 ml of ethyl acetate was added, and the solids were dissolved by heating. Afterwards, DABCO (1.5 g, 13.393 mmol) was added and heated to reflux at 80° C. for 12 h, and the color of the solution turned orange. The reaction mixture was suction-filtered and washed with ethyl acetate to give 1.5 g of product in a yield of 30.6%.

$^1$H NMR (400 MHz, DMSO-$d_6$): δ 9.21 (s, 1H), 7.91 (d, J=8.8 Hz, 1H), 7.81 (d, J=8.8 Hz, 1H), 7.62 (d, J=7.6 Hz, 1H), 7.39 (m, 2H), 7.24 (t, J=7.6 Hz, 1H), 7.13 (dd, $J_1$=8.8 Hz, $J_2$=2.0 Hz, 1H), 7.08 (s, 1H), 6.90 (d, J=8.8 Hz, 1H), 4.03 (s, 3H), 2.83 (s, 1H).

Synthesis of Intermediate 26-3

Compound 26-2 (2.49 g, 6.779 mol) was weighed in a 50 mL round bottom flask and THF/CH$_3$OH (10:1, 20 ml) was added to dissolve the solids. Sodium borohydride (317 mg, 11.391 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 26

The above obtained compound was dissolved in 50 mL of ethanol, and to the solution was added zinc powder (4.53 g, 69.692 mmol) and 8 mL of 6 N HCl. The reaction was performed at 50° C. for 2 hrs. The zinc powder was filtered off through diatomite. The solvent was evaporated to dryness. The obtained residue was dissolved in saturated aqueous sodium hydroxide, extracted with dichloromethane, and dried over anhydrous sodium sulfate. The solution was evaporated to dryness and separated by column chromatography (PE:EA=2:1) to give 170 mg of white product. LC-MS: 340.10 (M+1)$^+$.

$^1$H NMR (400 MHz, DMSO-$d_6$): δ 7.68 (d, J=8.8 Hz, 1H), 7.55 (d, J=8.8 Hz, 1H), 7.46 (m, 2H), 7.33 (t, J=4.0 Hz, 2H), 7.04 (s, 1H), 6.96 (dd, $J_1$=8.8 Hz, $J_2$=1.6 Hz, 1H), 6.85 (d, J=8.8 Hz, 1H), 5.09 (d, J=8.4 Hz, 1H), 3.82 (s, 3H), 3.17 (m, 2H), 2.80 (m, 1H).

27. trans-(2RS,3RS)-9-methoxy-3-(2,4-dichlorophenyl)-2,3-dihydro-1H-benzo[f]-chroman-2-amine (compound-27)

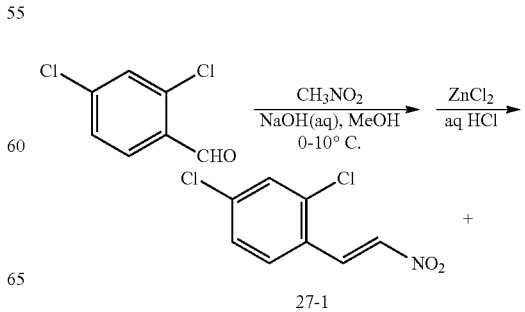

Synthesis of Intermediate 26-1

2-chlorobenzaldehyde (8.744 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pressure, and the filter cake was washed with 40% methanol solution for several times to give 8.1 g of product in a yield of 77.7%. GC-MS: 183.

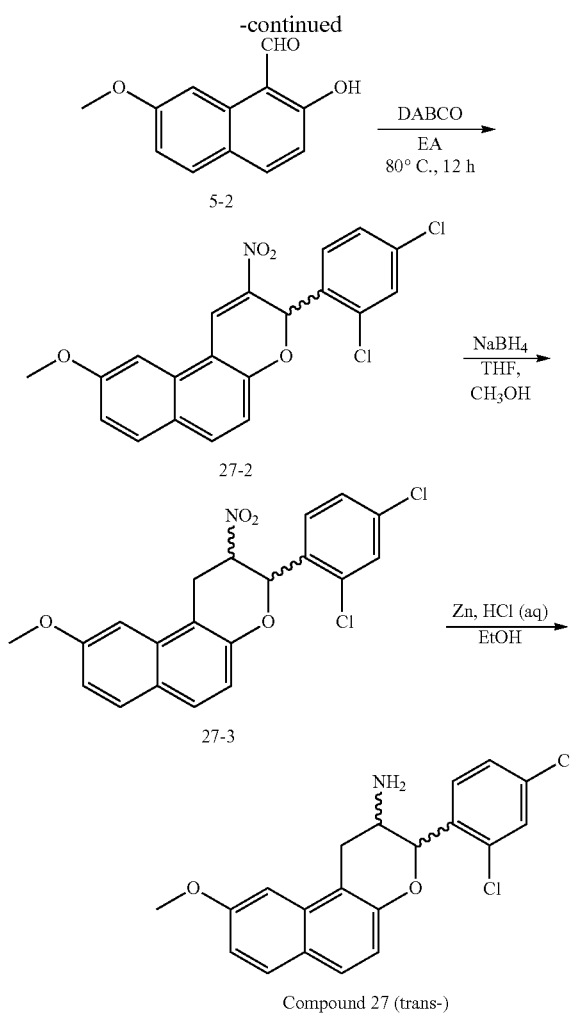

Synthesis of Intermediate 27-1

2,4-dichlorobenzaldehyde (10.866 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pressure, and the filter cake was washed with 40% methanol solution for several times to give 8.1 g of product in a yield of 77.7%. GC-MS: 217.

$^1$H NMR (400 MHz, DMSO-d$_6$): δ 8.31 (d, J=13.6, 1H), 8.18 (d, J=8.4, 1H), 8.07 (d, J=8.4 Hz, 1H), 7.84 (d, J=2.0 Hz, 1H), 7.58 (m, 1H).

Synthesis of Intermediate 27-2

7-methoxy-2-hydroxy-1-naphthaldehyde (4.0 g, 19.802 mmol), compound 5-2 (6.5 g, 29.954 mmol) was weighed into a 50 mL round bottom flask, 20 ml of ethyl acetate was added, and the solids were dissolved by heating. Afterwards, DABCO (2.2 g, 19.802 mmol) was added and heated to reflux at 80° C. for 12 h, and the color of the solution turned orange. The reaction mixture was suction-filtered and washed with ethyl acetate to give 3.0 g of product in a yield of 37.8%.

Synthesis of Intermediate 27-3

Compound 27-2 (2.72 g, 6.779 mol) was weighed in a 50 mL round bottom flask and THF/CH$_3$OH (10:1, 20 ml) was added to dissolve the solids. Sodium borohydride (317 mg, 11.391 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 27

The above obtained compound was dissolved in 50 mL of ethanol, and to the solution was added zinc powder (4.53 g, 69.692 mmol) and 8 mL of 6 N HCl. The reaction was performed at 50° C. for 2 hrs. The zinc powder was filtered off through diatomite. The solvent was evaporated to dryness. The obtained residue was dissolved in saturated aqueous sodium hydroxide, extracted with dichloromethane, and dried over anhydrous sodium sulfate. The solution was evaporated to dryness and separated by column chromatography (PE:EA=2:1) to give 170 mg of white product. LC-MS: 374.15 (M+1)$^+$.

$^1$H NMR (400 MHz, DMSO-d$_6$): δ 7.77 (d, J=8.8 Hz, 1H), 7.70 (d, J=2.0 Hz, 1H), 7.64 (d, J=8.8 Hz, 1H), 7.59 (d, J=8.4 Hz, 1H), 7.51 (m, 1H), 7.12 (d, J=2.0 Hz, 1H), 7.05 (dd, J$_1$=8.8 Hz, J$_2$=2.4 Hz, 1H), 6.92 (d, J=8.8 Hz, 1H), 5.13 (d, J=8.8 Hz, 1H), 3.90 (s, 3H), 3.015 (s, 2H), 2.88 (m, 1H).

28. trans-(2RS,3RS)-8,9-dimethoxy-3-(2,4-difluorophenyl)-2,3-dihydro-1H-benzo[f]-chroman-2-amine (compound-28)

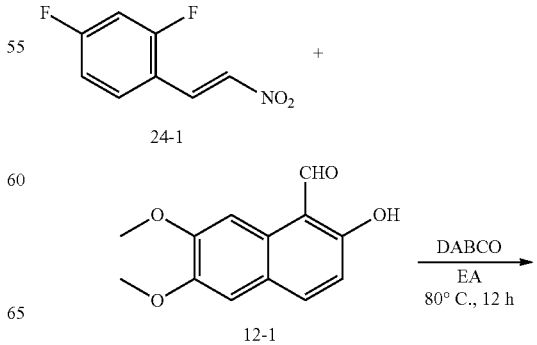

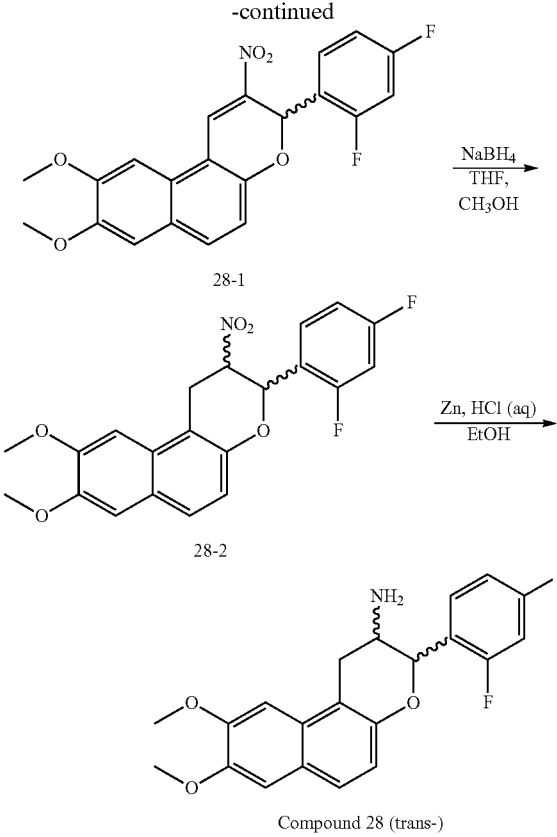

Compound 28 (trans-)

Synthesis of Intermediate 28-1

6,7-dimethoxy-2-hydroxy-1-naphthaldehyde (200 mg, 0.862 mmol), compound 2 (319 mg, 1.724 mmol) was weighed into a 50 mL round bottom flask, 20 ml of ethyl acetate was added, and the solids were dissolved by heating. Afterwards, DABCO (97 mg, 0.862 mmol) was added and heated to reflux at 80° C. for 12 h, and the color of the solution turned orange. The reaction mixture was suction-filtered and washed with ethyl acetate to give 150 mg of product in a yield of 44%.

Synthesis of Intermediate 28-2

Compound 8 (48 mg, 0.120 mol) was weighed in a 50 mL round bottom flask and THF/CH$_3$OH (10:1, 5 ml) was added to dissolve the solids. Sodium borohydride (9.08 mg, 0.240 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 28

The above obtained compound was dissolved in 50 mL of ethanol, and to the solution was added zinc powder (78 mg, 1.2 mmol) and 2 mL of 6 N HCl. The reaction was performed at 50° C. for 2 hrs. The reaction solution was neutralized with saturated aqueous sodium bicarbonate, extracted with ethyl acetate, and dried over anhydrous sodium sulfate. The solution was evaporated to dryness and separated by column chromatography (PE:EA=2:1) to give 15 mg of white product. LC-MS: 272.20 (M+1)$^+$.

$^1$HNMR (400 MHz, DMSO-d$_6$): δ 7.59 (m, 2H), 7.31 (m, 2H), 7.16 (m, 1H), 7.10 (s, 1H), 6.89 (d, J=8.8 Hz, 1H), 4.90 (d, J=8.8 Hz, 1H), 3.92 (s, 3H), 3.86 (s, 3H), 3.43 (d, J=5.6 Hz, 1H), 3.29 (d, J=5.2 Hz, 1H), 2.83 (q, J=9.6 Hz, 1H).

29. trans-(2RS,3RS)-8,9-dimethoxy-3-phenyl-2,3-dihydro-1H-benzo[f]-chroman-2-amine (compound-29)

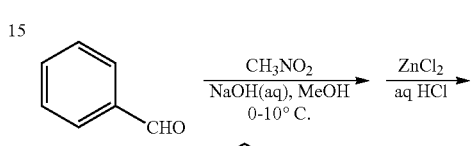

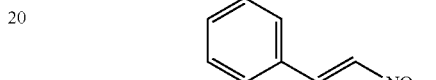

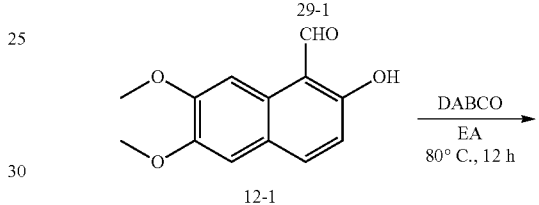

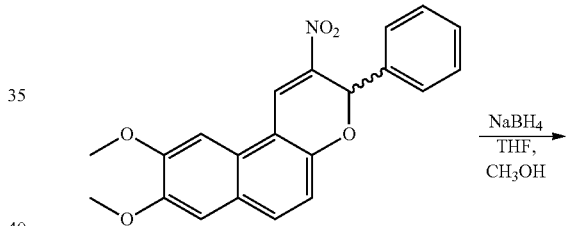

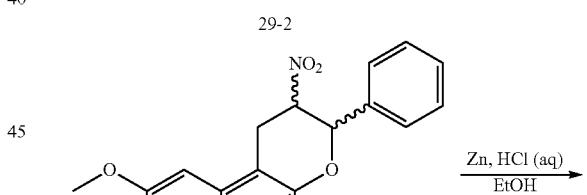

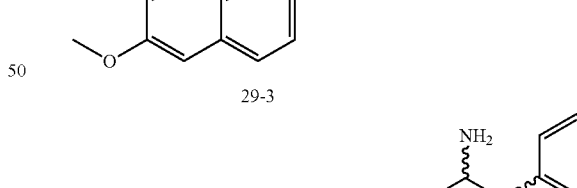

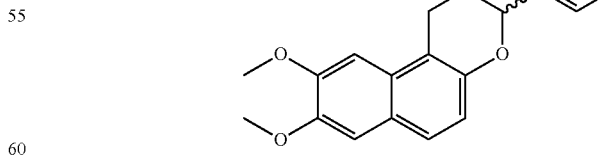

Compound 29 (trans-)

Synthesis of Intermediate 29-1

Benzaldehyde (6.620 g, 62.46 mmol), nitromethane (4 mL), methanol (10 mL) were prepared into a solution; and methanol (60 mL), water (30 mL), NaOH (2.5 N, 30 mL) were prepared into a solution. The temperature was maintained at 5° C. The former solution was added dropwise into the latter solution over about 30-60 min, and the temperature of solution was maintained at 5-10° C. Upon addition, the above solution was added dropwise to a mixed solution of zinc chloride (42.6 g, 31.25 mmol), concentrated hydrochloric acid (13 mL) and water (17 mL), and the temperature during addition was maintained at 0 to 10° C. Upon addition, the reaction was carried out at room temperature for 2-4 h. After the reaction was completed, the reaction mixture was suction-filtered under reduced pressure, and the filter cake was washed with 40% methanol solution for several times to give 6.8 g of product in a yield of 73%. GC-MS: 149.

$^1$HNMR (400 MHz, DMSO-$d_6$): δ 8.19 (q, J=13.6 Hz, 2H), 7.87 (d, J=7.2 Hz, 2H), 7.56-7.47 (m, 3H).

Synthesis of Intermediate 29-2

6,7-dimethoxy-2-hydroxy-1-naphthaldehyde (200 mg, 0.862 mmol), compound 2 (257 mg, 1.724 mmol) was weighed into a 50 mL round bottom flask, 20 ml of ethyl acetate was added, and the solids were dissolved by heating. Afterwards, DABCO (97 mg, 0.862 mmol) was added and heated to reflux at 80° C. for 12 h, and the color of the solution turned orange. The reaction mixture was suction-filtered and washed with ethyl acetate to give 150 mg of product in a yield of 44%.

Synthesis of Intermediate 29-3

Compound 8 (43.57 mg, 0.120 mol) was weighed in a 50 mL round bottom flask and THF/CH$_3$OH (10:1, 5 ml) was added to dissolve the solids. Sodium borohydride (9.08 mg, 0.240 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 29

The above obtained compound was dissolved in 50 mL of ethanol, and to the solution was added zinc powder (78 mg, 1.2 mmol) and 2 mL of 6 N HCl. The reaction was performed at 50° C. for 2 hrs. The reaction solution was neutralized with saturated aqueous sodium bicarbonate, extracted with ethyl acetate, and dried over anhydrous sodium sulfate. The solution was evaporated to dryness and separated by column chromatography (PE:EA=4:1) to give 14 mg of white product.

30. trans-(2RS,3RS)-8,9-dimethoxy-3-(2,4-dichlorophenyl)-2,3-dihydro-1H-benzo[f]-chroman-2-amine (compound-30)

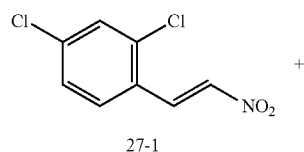

27-1

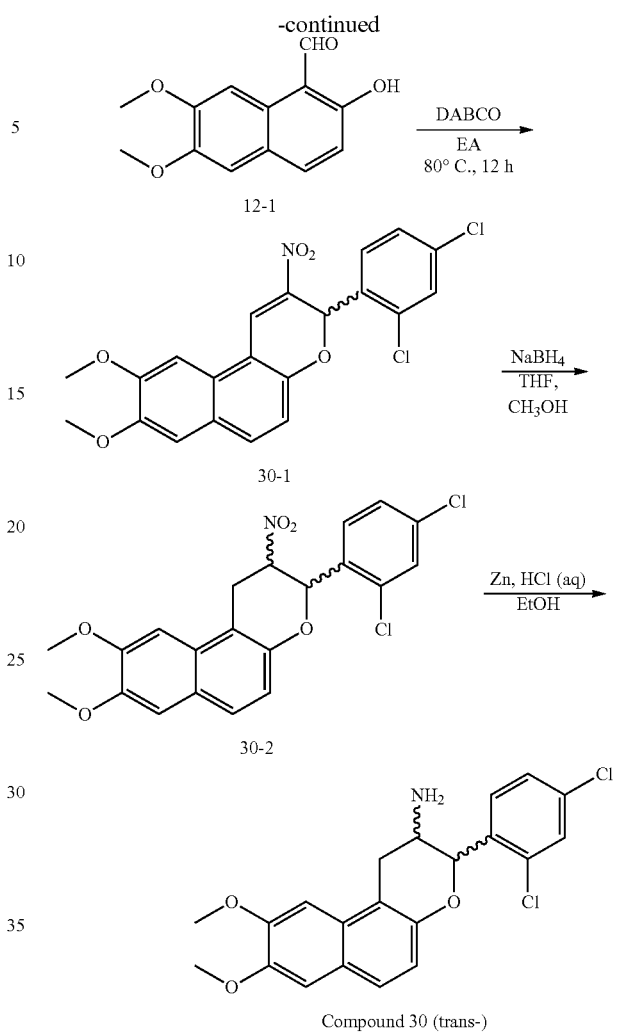

Synthesis of Intermediate 30-1

6,7-dimethoxy-2-hydroxy-1-naphthaldehyde (200 mg, 0.862 mmol), compound 12-1 (374 mg, 1.724 mmol) was weighed into a 50 mL round bottom flask, 20 ml of ethyl acetate was added, and the solids were dissolved by heating. Afterwards, DABCO (97 mg, 0.862 mmol) was added and heated to reflux at 80° C. for 12 h, and the color of the solution turned orange. The reaction mixture was suction-filtered and washed with ethyl acetate to give 150 mg of product in a yield of 44%.

Synthesis of Intermediate 30-2

Compound 30-1 (52 mg, 0.120 mol) was weighed in a 50 mL round bottom flask and THF/CH$_3$OH (10:1, 5 ml) was added to dissolve the solids. Sodium borohydride (9.08 mg, 0.240 mmol) was added into the solution in portions. A drying tube was installed at the mouth of the bottle. The reaction was performed for 20 mins at room temperature and under normal pressure until the reaction solution was a clear solution. After the reaction was completed, water was added into the reaction solution for quenching the reaction, extracted with ethyl acetate, and dried over anhydrous sodium sulfate. The solution was evaporated to dryness in vacuo, and the residue was directly used in the next reaction.

Synthesis of Compound 30

The above obtained compound was dissolved in 50 mL of ethanol, and to the solution was added zinc powder (78 mg, 1.2 mmol) and 2 mL of 6 N HCl. The reaction was performed at 50° C. for 2 hrs. The reaction solution was neutralized with saturated aqueous sodium bicarbonate, extracted with ethyl acetate, and dried over anhydrous sodium sulfate. The solution was evaporated to dryness and separated by column chromatography (PE:EA=4:1) to give 16 mg of white product. LC-MS: 404.05 (M+1)$^+$.

$^1$HNMR (400 MHz, DMSO-d$_6$): δ 7.69 (s, 1H), 7.59 (d, J=8.4 Hz, 1H), 7.57 (d, J=9.2 Hz, 1H), 7.50 (d, J=8.4 Hz, 1H), 7.28 (s, 1H), 7.10 (s, 1H), 6.90 (d, J=8.8 Hz, 1H), 5.09 (d, J=8.8 Hz, 1H), 3.91 (s, 3H), 3.86 (s, 3H), 3.47 (q, J=7.6 Hz, 1H), 3.27 (q, J=7.2 Hz, 1H), 2.87 (q, J=9.2 Hz, 1H).

Example 31. DPP4 Inhibitory Activity of the Compounds of the Invention

The inventors tested the inhibitory activity of the compounds of the present invention on DPP4 by the following experiment at enzyme level:

Activity Evaluation at Enzyme Level:

Name: DPP4 (Dipeptidyl peptidase4); Alias: CD26; ADABP; ADCP2; DPPIV; TP103; Fill name: dipeptidyl-peptidase 4 (CD26, adenosine deaminase complexing protein.

Screening Method:

Name of method: Activity Evaluation of DPP4, Fluorescence.

Instrument: Microplate reader, Envision (PerkinElmer, USA).

Material: human DPP4, which was, in this experiment, obtained by using baculovirus expression system in insect cells. Substrate was Gly-Pro-AMC.

Process:

DPP4 can specifically hydrolyze the substrate, Gly-Pro-AMC to produce a product, AMC, which, excited by UV light at 355 nm, can produce emission light at 460 nm. Linear change of fluorescence values were dynamically measured at 460 nm wavelengths per unit time, thereby calculating DPP4 activity. MERK-0431 was used as a control compound in the experiment.

Sample Processing:

A sample is dissolved in DMSO and stored at low temperature, and the concentration of DMSO in the final system shall be controlled within a range that won't affect the detection of activity.

Data Processing and Result Description:

For preliminary screening, a single concentration, for example 20 μg/ml is selected for testing activities of a sample. For a sample exhibiting activities under a certain condition, such as inhibition rates greater than 50%, activity dose-dependency, i.e, IC$_{50}$/EC$_{50}$ is tested which is obtained by non-linear fitting of the activity of the sample vs the concentration of the sample was. The software used for calculation is Graphpad Prism 4, and the model used for fitting is sigmoidal dose-response (variable slope). For most screening models of inhibitor, the bottom and top of the fitting curve are set as 0 and 100. Generally, replicate wells (n≥2) are set for each sample, and results are shown as standard deviation (SD) or standard error (SE).

The activity data showed that inhibitory IC$_{50}$ values of the compounds of the present invention on DPP-4 are at about nM level which is about 50 nM and comparable to those of the control compounds, and some of them could even reach a level less than 10 nM (see following table).

Activity data: inhibitory IC$_{50}$ values for Compounds on DPP-4

| Compound | Structural formula (Including resolved structures and mixture of two trans configuration) | DPP 4 IC$_{50}$ (nM) |
|---|---|---|
| 1 | | 3320 |
| 2 | | 207 |

-continued

| | Activity data: inhibitory IC$_{50}$ values for Compounds on DPP-4 | |
|---|---|---|
| Compound | Structural formula (Including resolved structures and mixture of two trans configuration) | DPP 4 IC$_{50}$ (nM) |
| 3 | | 154 |
| 4 | | 282.89 |
| 5 | | 15 |
| 6 | | 20 |
| 7 | | 39 |

-continued

| | Activity data: inhibitory IC$_{50}$ values for Compounds on DPP-4 | |
|---|---|---|
| Compound | Structural formula (Including resolved structures and mixture of two trans configuration) | DPP 4 IC$_{50}$ (nM) |
| 8 | | 216 |
| 9 | | 9.17 |
| 10 | | 18 |
| 11 | | 205 |
| 12 | | 4 |

-continued

Activity data: inhibitory IC$_{50}$ values for Compounds on DPP-4

| Compound | Structural formula (Including resolved structures and mixture of two trans configuration) | DPP 4 IC$_{50}$ (nM) |
| --- | --- | --- |
| 13 | | 169 |
| 14 | | 74 |
| 15 | | 110 |
| MK0431 | sitagliptin (I) | 14 |
| MK3102 | | 2 |

-continued

| | Activity data: inhibitory IC$_{50}$ values for Compounds on DPP-4 | |
|---|---|---|
| Compound | Structural formula (Including resolved structures and mixture of two trans configuration) | DPP 4 IC$_{50}$ (nM) |
| 16 | | 11 |
| 17 | | 6 |
| 18 | | 70 |
| 19 | | 2 |

-continued

Activity data: inhibitory $IC_{50}$ values for Compounds on DPP-4

| Compound | Structural formula (Including resolved structures and mixture of two trans configuration) | DPP 4 $IC_{50}$ (nM) |
|---|---|---|
| 20 | | 30 |
| 21 | | 2 |
| 22 | | 564 |
| 23 | | 800 |
| 24 | | 78 |

-continued

Activity data: inhibitory IC$_{50}$ values for Compounds on DPP-4

| Compound | Structural formula (Including resolved structures and mixture of two trans configuration) | DPP 4 IC$_{50}$ (nM) |
|---|---|---|
| 25 | | 33 |
| 26 | | 338 |
| 27 | | 678 |
| 28 | | 56 |
| 29 | | 254 |
| 30 | | 55 |

Therefore, the activity evaluation at enzyme level shows that the activities of the compounds of the present invention are comparable to or even superior to those of existing drugs.

All documents mentioned in the present invention are incorporated herein by reference, as if each document were individually recited for reference. Additionally, it is to be understood that a skilled person can make various changes or modifications to the present invention after reading the teachings of the present invention, and such equivalents also fall within the scope of the claims as appended hereto.

The invention claimed is:

1. A compound having formula I, or a pharmaceutically acceptable salt or prodrug thereof, or an optically active isomer or solvate thereof:

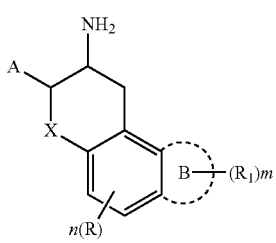

wherein:

X is O

A is a benzene ring with 1 to 5 substituents, wherein each substituent is independently a halogen, a cyano, a hydroxy, a $C_{1-6}$ alkyl, a $C_{1-6}$ alkyl substituted by halogen, a $C_{1-6}$ alkoxy, or a $C_{1-6}$ alkoxy substituted by halogen;

A is a nitrogen-containing, or sulfur-containing five-membered or six-membered saturated or unsaturated heterocycle with 1 to 4 substituents, wherein each substituent is independently a halogen, a cyano, or a boronic acid group; or A is a heterocycle selected from the following structures:

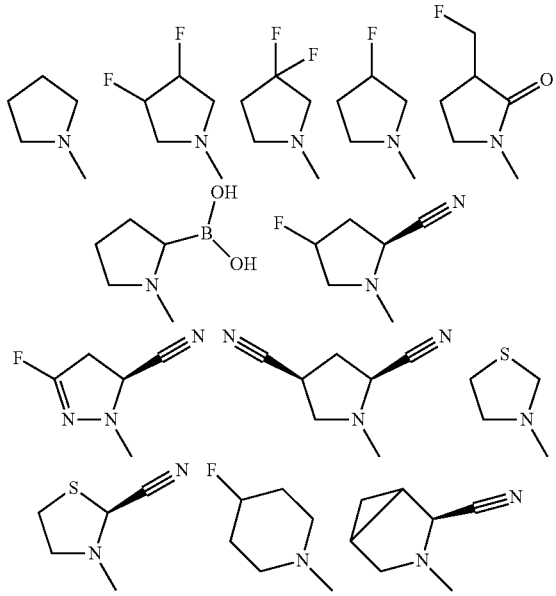

R is H, a halogen, a cyano, a hydroxy, a $C_{1-6}$ alkyl, $C_{1-6}$ alkyl with 1 to 5 F atoms, $C_{1-6}$ alkoxy, or $C_{1-6}$ alkoxy with 1 to 5 F atoms;

n is an integer of 1-2;

Ring B is an aromatic benzene ring, an aromatic heterocycle, a saturated or unsaturated 5-membered or 6-membered ring, a nitrogen-, oxygen-, or sulfur-containing five- or six-membered saturated or unsaturated heterocycle;

$R_1$ is independently selected from the group consisting of a halogen, a cyano, a hydroxy, a $C_{1-6}$ alkyl, a $C_{1-6}$ alkyl group containing 1 to 5 F atoms, a $C_{1-6}$ alkoxy, a $C_{1-10}$ alkylcarbonyloxy, a $C_{1-3}$ alkoxymethoxy, a disubstituted $OCH_2CH_2O$ and $OCH_2O$, COOH, a $C_{1-6}$ alkoxycarbonyl, a carbamoyl, a methylcarbamido, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, an amino, a $NR^2R^3$, a $C_{1-5}$alkylcarboxamido, a $C_{3-5}$ alkyllactam group, a $C_{1-6}$ alkylsulfonamido, a $C_{3-5}$ alkylsultam group, a mercapto, a $C_{1-6}$ alkylthio, a $C_{1-6}$ alkylthio containing 1 to 5 F atoms, a $C_{1-6}$ alkylsulfinyl, a $C_{1-6}$ alkylsulfonyl, a $C_{3-5}$ cycloalkylsulfonyl, and a $C_{1-5}$alkylsulfinyl, a N-propanesulfonyllactam group, a N-butanesulfonyllactam group, and a 3-pyrazolylamino;

m is an integer of 1 to 4; and $R^2$, $R^3$ are independently selected from a $C_{1-6}$ alkyl, or $R^2$ and $R^3$ together form a substituted or unsubstituted 5- or 6-membered heterocycloalkyl, or a substituted or unsubstituted 5-or 6-membered heterocycle group additionally containing N or O.

2. The compound of claim 1, or a pharmaceutically acceptable salt or prodrug thereof, or an optically active isomer or solvate thereof, wherein the compound is shown in general formula (II):

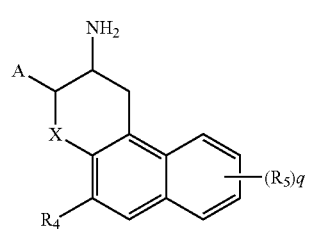

wherein,

X is O

A is a benzene ring with 1 to 5 substituents, wherein each substituent is independently a halogen, a cyano, a hydroxy, a $C_{1-6}$ alkyl, a $C_{1-6}$ alkyl substituted by halogen, a $C_{1-6}$ alkoxy, or a $C_{1-6}$ alkoxy substituted by halogen;

$R^4$ is H, a hydroxyl, F, or a cyano;

$R^5$ is a halogen, a cyano, a hydroxyl, a mercapto, a $C_{1-6}$ alkyl group, a $C_{1-6}$ alkyl group containing 1 to 5 F atoms, a $C_{1-6}$ alkoxy, a $C_{1-10}$ alkylcarbonyloxy, a $C_{1-3}$ alkoxymethyloxy, COOH, a $C_{1-6}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a $C_{1-6}$ alkylthio, a $C_{1-6}$ alkylthio containing 1 to 5 F atoms, a $C_{1-6}$ alkylsulfinyl, a $C_{1-6}$ alkylsulfonyl, an amino, an acetylamino, a methanesulfonamido, a methylcarbamido, a N-propanesulfonyllactam group, a N-butanesulfonyllactam group, a 4-morpholinyl, a N-methylpiperazin-4-yl, a piperazinyl, a 3-methanesulfonylpiperazinyl, a 3,3-difluorotetrahydropyrrolyl, a 2-aminoformylpiperidyl, or a 3-pyrazolylamino; and q is an integer of 1-4.

3. The compound of claim 1, or a pharmaceutically acceptable salt or prodrug thereof, or an optically active isomer or solvate thereof, wherein the compound is shown in general formula (II):

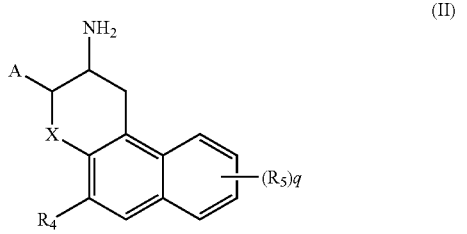

(II)

wherein,

X is O

A is a benzene ring with 1 to 5 substituents, wherein each substituent is independently a halogen, a cyano, a hydroxy, a $C_{1-6}$ alkyl, a $C_{1-6}$ alkyl substituted by halogen, a $C_{1-6}$ alkoxy, or a $C_{1-6}$ alkoxy substituted by halogen;

$R^4$ is H, a hydroxyl, F, or a cyano;

$R^5$ is a halogen, a cyano, a hydroxyl, a mercapto, a $C_{1-6}$ alkyl group, a $C_{1-6}$ alkyl group containing 1 to 5 F atoms, a $C_{1-6}$ alkoxy, a $C_{1-3}$ alkoxymethyloxy, COOH, a $C_{1-6}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a $C_{1-6}$ alkylthio,-a $C_{1-6}$ alkylthio containing 1 to 5 F atoms, a $C_{1-6}$ alkylsulfinyl, a $C_{1-6}$ alkylsulfonyl, an amino, an acetylamino, a methanesulfonamido, a methylcarbamido, a N-propanesulfonyllactam group, a N-butanesulfonyllactam group, a 4-morpholinyl, a N-methylpiperazin-4-yl, a piperazinyl, a 3-methanesulfonylpiperazinyl, a 3,3-difluorotetrahydropyrrolyl, a 2-aminoformylpiperidyl, or a 3-pyrazolylamino; and q is an integer of 1-4.

4. The compound of claim 1, or a pharmaceutically acceptable salt or prodrug thereof, or an optically active isomer or solvate thereof, wherein the compound is shown in general formula (III):

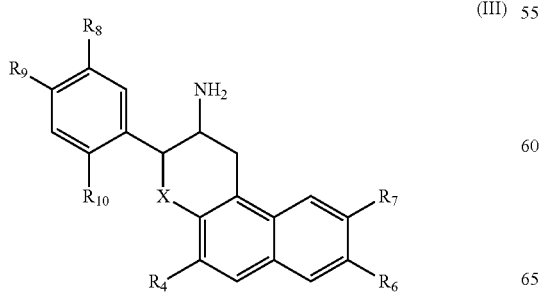

(III)

wherein

X is O $R^4$ is H or a hydroxyl;

$R^6$, $R^7$ are independently a hydrogen, a halogen, a cyano, a hydroxy, a mercapto, a $C_{1-2}$ alkoxy, a $C_{1-2}$ alkylcarbonyloxy, a $C_{1-3}$ alkoxymethoxy, COOH, a $C_{1-2}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a methylthio, a methylsulfinyl, a methanesulfonyl, an amino, acetamido, methanesulfonamido, a methylcarbamido, N-propanesulfonyllactam group, N-butanesulfonyllactam group, a 4-morphinyl, a N-methylpiperazin-4-yl, a piperazinyl, a 3-methanesulfonylpiperazinyl, a 3,3-difluorotetrahydropyrrolyl, a 2-aminoformylpiperidyl, or a 3-pyrazolylamino; and $R^8$, $R^9$ and $R^{10}$ are independently H, Cl, F, or a cyano.

5. The compound of claim 1, or a pharmaceutically acceptable salt or prodrug thereof, or an optically active isomer or solvate thereof, wherein the compound is shown in general formula (III):

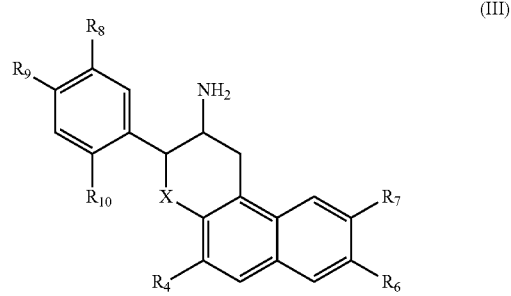

(III)

wherein

X is O;

$R^4$ is H or a hydroxyl;

$R^6$, $R^7$ are independently selected from a hydrogen, a halogen, a cyano, a hydroxy, a mercapto, a $C_{1-2}$ alkoxy, a $C_{1-3}$ alkoxymethoxy, COOH, a $C_{1-2}$ alkoxycarbonyl, a carbamoyl, a cyanomethylcarbonyl, an acetamidomethylcarbonyl, a 2-pyrrocarbonyl, a methoxycarbonylmethyl, a 4-pyranylcarbonyl, a 4-morpholinecarbonyl, a 1-piperazinecarbonyl, a methylthio, a methylsulfinyl, a methanesulfonyl, an amino, acetamido, methanesulfonamido, a methylcarbamido, N-propanesulfonyllactam group, N-butanesulfonyllactam group, a 4-morphinyl, a N-methylpiperazin-4-yl, a piperazinyl, a 3-methanesulfonylpiperazinyl, a 3,3-difluorotetrahydropyrrolyl, a 2-aminoformylpiperidyl, or a 3-pyrazolylamino; and $R^8$, $R^9$ and $R^{10}$ are independently H, Cl, F, or a cyano.

6. The compound of claim 1, or a pharmaceutically acceptable salt or prodrug thereof, or an optically active isomer or solvate thereof, wherein the $C_{1-6}$ alkyl substituted by halogen is $C_{1-6}$ alkyl substituted by F; and the $C_{1-6}$ alkoxy substituted by halogen is $C_{1-6}$ alkoxy substituted by F.

7. The compound of claim 1, or a pharmaceutically acceptable salt or prodrug thereof, or an optically active isomer or solvate thereof, wherein the $C_{1-6}$ alkyl substituted by halogen is $C_{1-6}$ alkyl substituted by 1 to 5 F; and the $C_{1-6}$ alkoxy substituted by halogen is $C_{1-6}$ alkoxy substituted by 1 to 5 F.

8. The compound of claim 2, or a pharmaceutically acceptable salt or prodrug thereof, or an optically active isomer or solvate thereof, wherein the $C_{1-6}$ alkyl substituted by halogen is $C_{1-6}$ alkyl substituted by F; and the $C_{1-6}$ alkoxy substituted by halogen is $C_{1-6}$ alkoxy substituted by F.

9. The compound of claim 2, or a pharmaceutically acceptable salt or prodrug thereof, or an optically active isomer or solvate thereof, wherein the $C_{1-6}$ alkyl substituted by halogen is $C_{1-6}$ alkyl substituted by 1 to 5 F; and the $C_{1-6}$ alkoxy substituted by halogen is $C_{1-6}$ alkoxy substituted by 1 to 5 F.

10. The compound of claim 3, or a pharmaceutically acceptable salt or prodrug thereof, or an optically active isomer or solvate thereof, wherein wherein the $C_{1-6}$ alkyl substituted by halogen is $C_{1-6}$ alkyl substituted by F; and the $C_{1-6}$ alkoxy substituted by halogen is $C_{1-6}$ alkoxy substituted by F.

11. The compound of claim 3, or a pharmaceutically acceptable salt or prodrug thereof, or an optically active isomer or solvate thereof, wherein the $C_{1-6}$ alkyl substituted by halogen is $C_{1-6}$ alkyl substituted by 1 to 5 F; and the $C_{1-6}$ alkoxy substituted by halogen is $C_{1-6}$ alkoxy substituted by 1 to 5 F.

12. A compound selected from the following group, or a pharmaceutically acceptable salt or prodrug thereof:

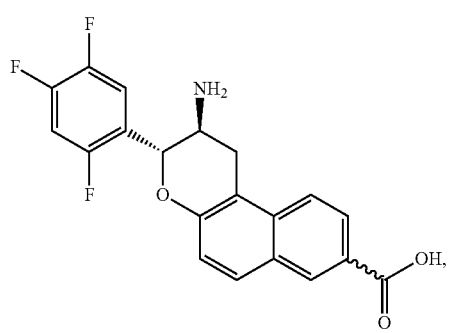

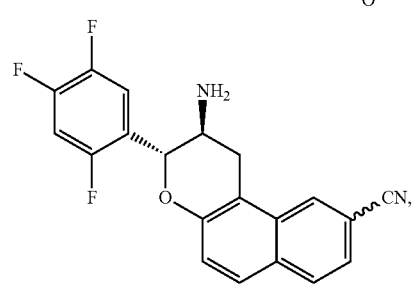

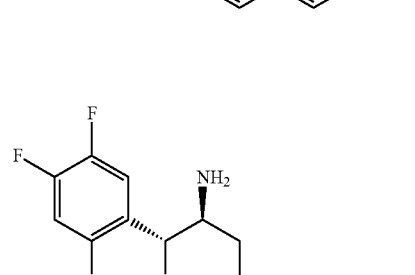

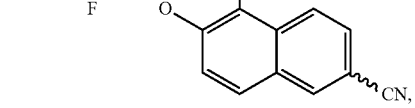

-continued

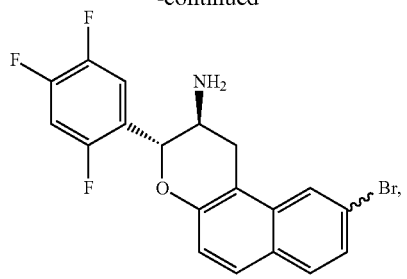

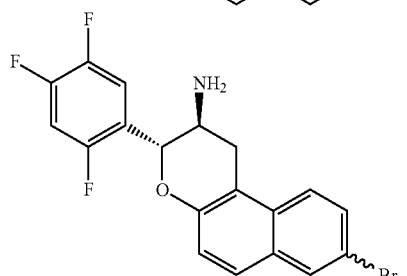

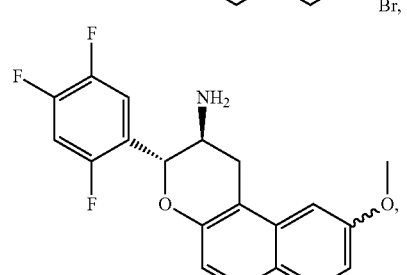

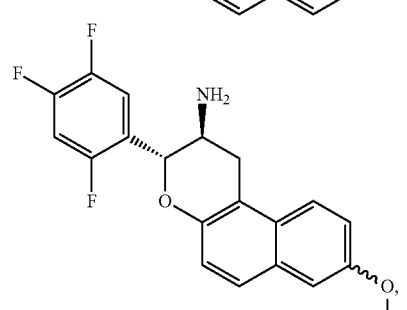

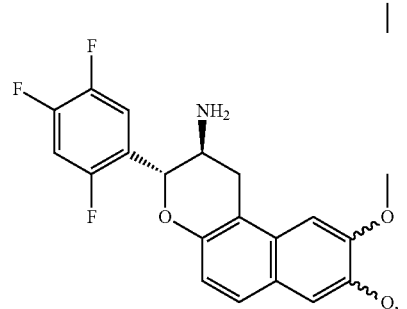

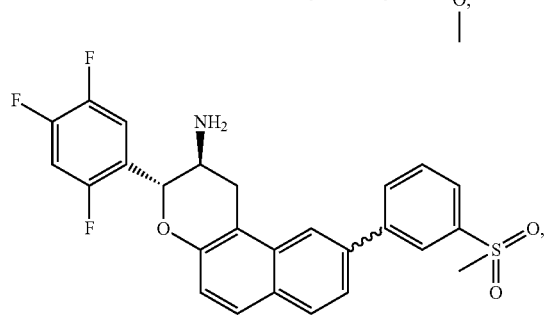

113
-continued
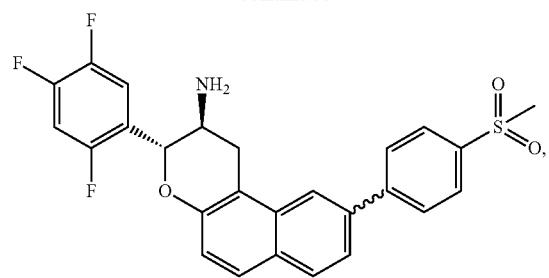
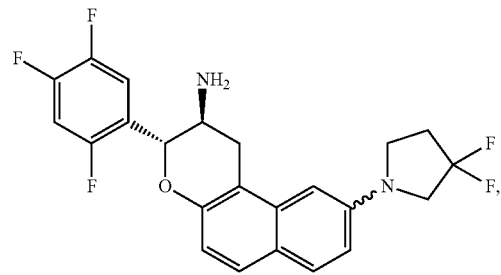
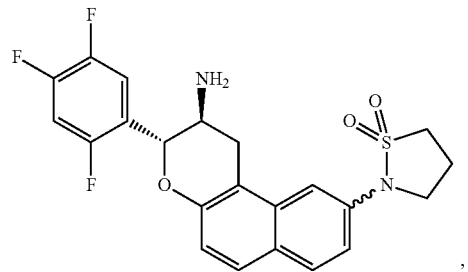
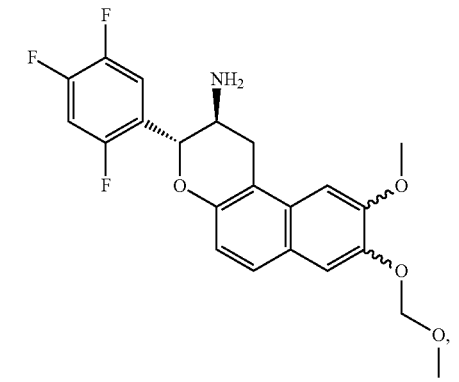
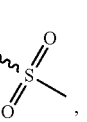
114
-continued
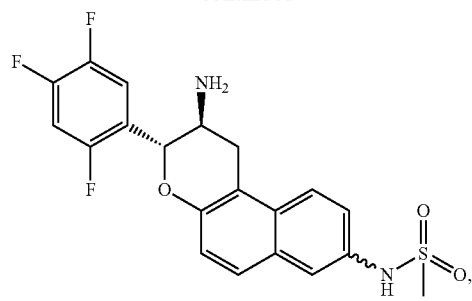
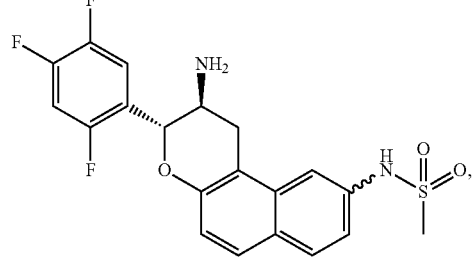
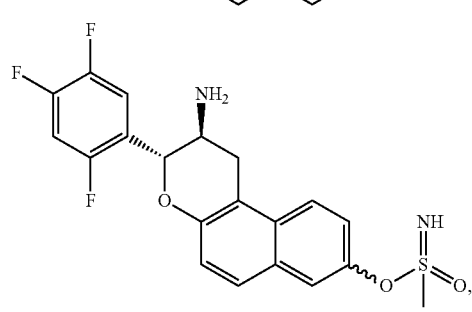
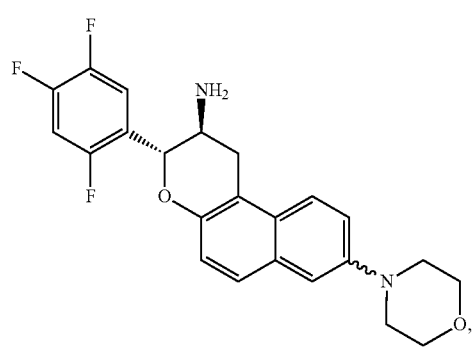
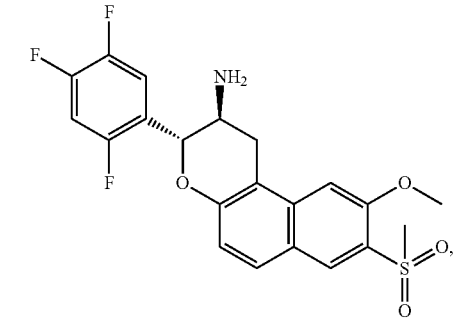

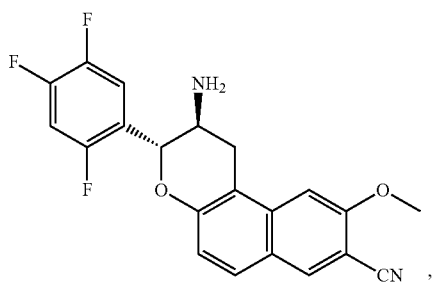
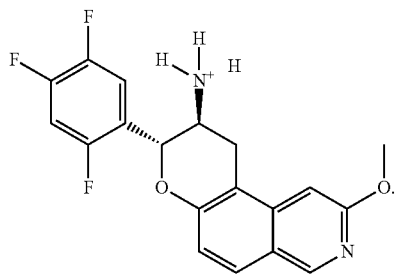
13. A compound selected from the following group, or a pharmaceutically acceptable salt or prodrug thereof:
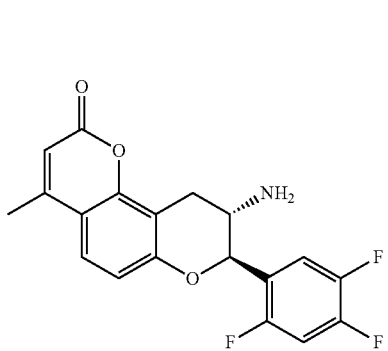 [SMILES: Cc1cc(=O)oc2c3c(ccc12)O[C@H](c1cc(F)c(F)cc1F)[C@@H](N)C3]
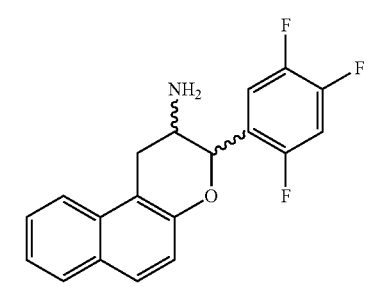 [SMILES: NC1Cc2c(ccc3ccccc23)OC1c1cc(F)c(F)cc1F]
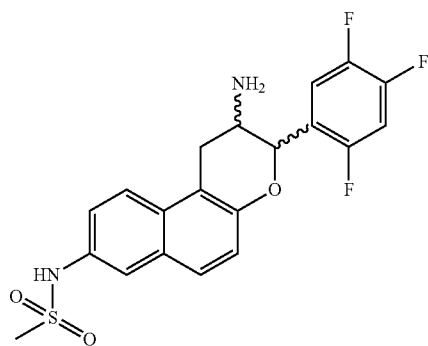 [SMILES: CS(=O)(=O)Nc1ccc2c3c(ccc2c1)OC(c1cc(F)c(F)cc1F)C(N)C3]
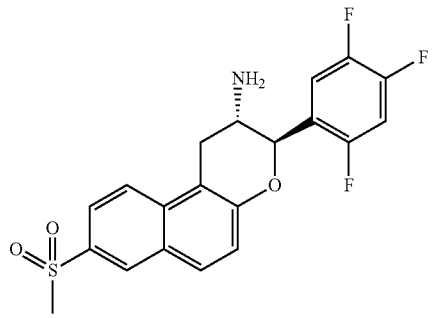 [SMILES: CS(=O)(=O)c1ccc2c3c(ccc2c1)O[C@H](c1cc(F)c(F)cc1F)[C@@H](N)C3]
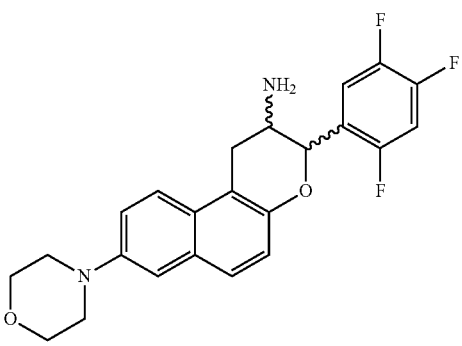 [SMILES: NC1Cc2c(ccc3cc(N4CCOCC4)ccc23)OC1c1cc(F)c(F)cc1F]
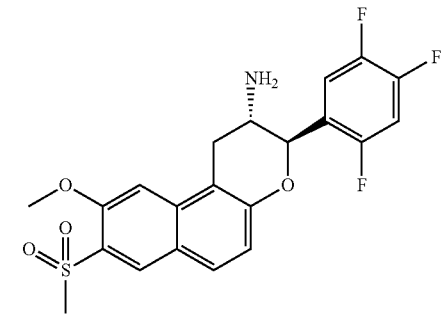 [SMILES: COc1cc2c3c(ccc2cc1S(C)(=O)=O)O[C@H](c1cc(F)c(F)cc1F)[C@@H](N)C3]
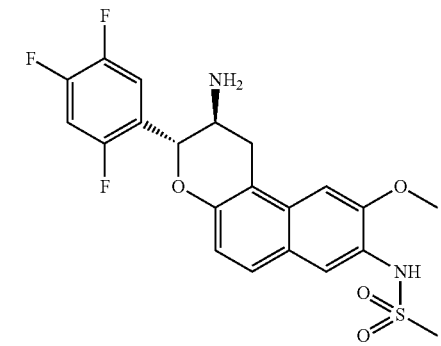 [SMILES: COc1cc2c3c(ccc2cc1NS(C)(=O)=O)O[C@H](c1cc(F)c(F)cc1F)[C@@H](N)C3]

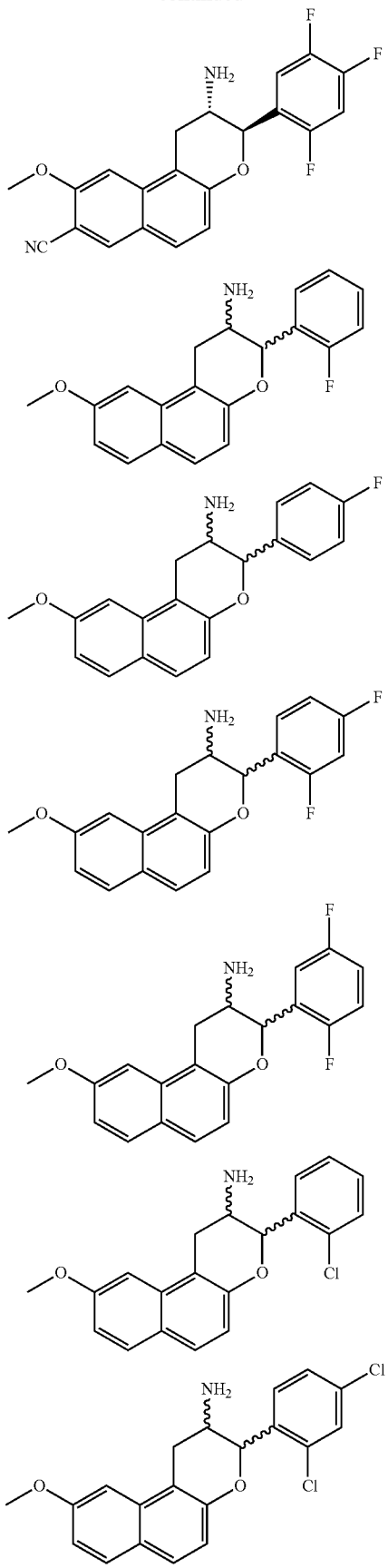

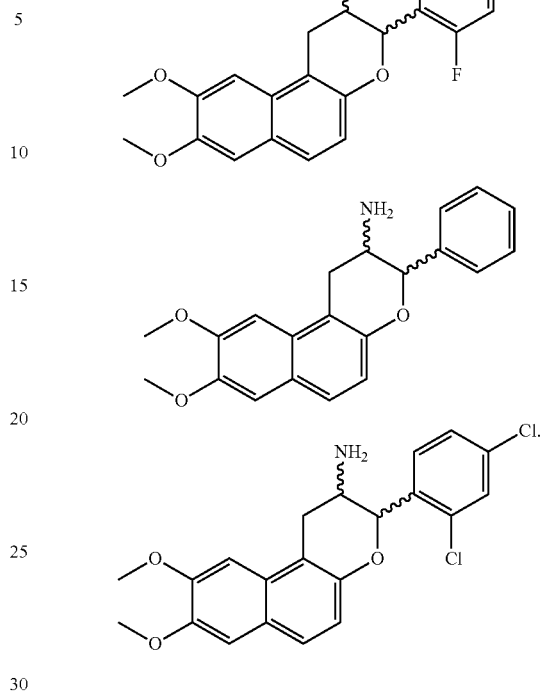

14. A pharmaceutical composition comprising a compound of claim 1 or a pharmaceutically acceptable salt or prodrug thereof, and a pharmaceutically acceptable carrier or excipient.

15. The pharmaceutical composition of claim 14, wherein the pharmaceutical composition is in a dosage form suitable for oral administration.

16. The pharmaceutical composition of claim 15, wherein the dosage form suitable for oral administration is a tablet, a solution, a suspension, a capsules, a granule, or a powder.

17. A preparation method of a compound of claim 1, wherein the method includes following steps:

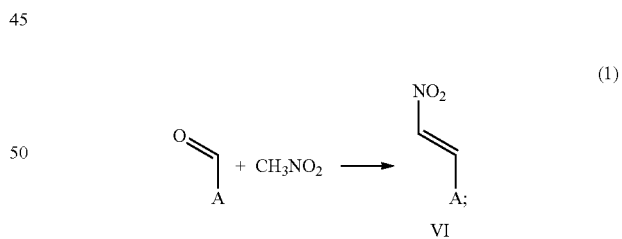

(1)

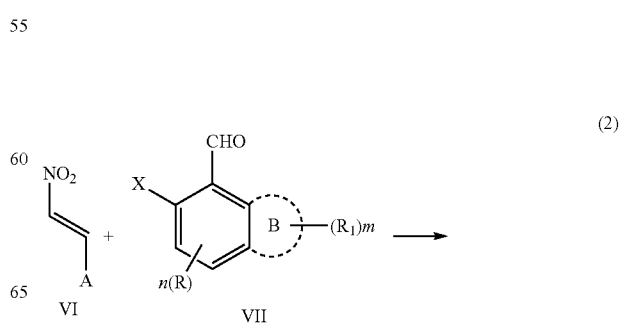

(2)

-continued
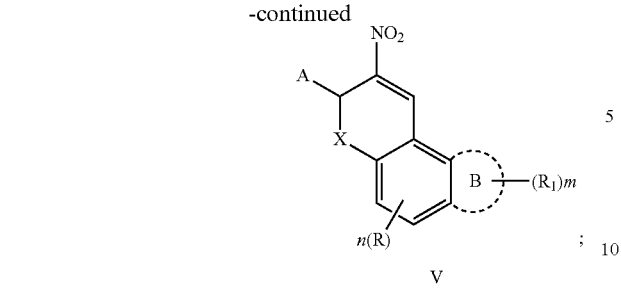
V (3)
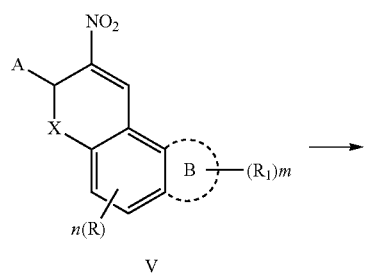
V
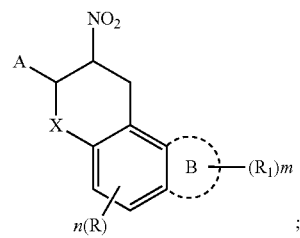
VI ; and
-continued
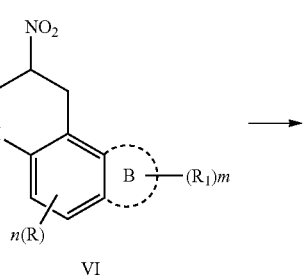
(4)
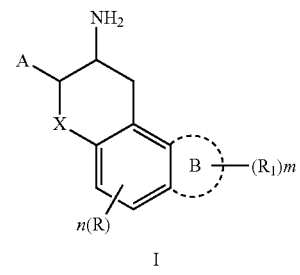
I ;
wherein X, A, R, B, and $R_1$ are defined in claim 1.
* * * * *